(12) United States Patent
Rosen et al.

(10) Patent No.: US 6,855,515 B1
(45) Date of Patent: Feb. 15, 2005

(54) AUTOANTIGENIC FRAGMENTS, METHODS AND ASSAYS

(75) Inventors: Anthony Rosen, Columbia, MD (US); Livia Casciola-Rosen, Columbia, MD (US); Donald W. Nicholson, Montreal (CA); Felipe A. Andrade, Baltimore, MD (US); Sophie Roy, Montreal (CA); Nancy A. Thornberry, Westfield, NJ (US)

(73) Assignees: Merck & Co., Inc., Rahway, NJ (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/296,662

(22) Filed: Apr. 22, 1999

Related U.S. Application Data
(60) Provisional application No. 60/082,643, filed on Apr. 22, 1998.

(51) Int. Cl.$^7$ ................................................. C12P 21/06
(52) U.S. Cl. ..................................................... 435/68.1
(58) Field of Search ........................................ 435/68.1

(56) References Cited

PUBLICATIONS

Casciano, et al., "Selective Cleavage of Nuclear Autoantigens During CD95 (Fas/APO–1)–mediated T Cell Apopsotis", J. Exp. Med., vol. 184, Aug. 1996, pp. 765–770.
Casciano, et al., "Antinuclear autoantibodies: probes for defining proteolytic events associated with apoptosis", Molecular Biology Reports, vol. 23, pp. 211–216, 1996.
Rosen, et al, "Macromolecular Substrates for the ICE–Like Proteases During Apoptosis", Journal of Cellular Biochemistry, vol. 64, pp. 50–54, 1997.
Bach, et al., "New clues to systemic lupus", Lancet, vol. 350, pp. 11, 1997.
Beidler, et al., "The baculovirus p35 protein inhibits Fas– and tumor necrosis factor–induced apoptosis", J. Biol. Chem., vol. 270, pp. 16526–16528, 1995.
Bockenstedt, et al., "Self–peptides in the initiation of lupus autoimmunity", J. Immunol., vol. 154, pp. 3516–3524, 1995.
Bump, et al., "Inhibition of ICE family proteases by baculovirus antiapoptotic protein p35", Science, vol. 269, pp. 1885–1888, 1995.
Burlingame, et al., "Genesis and evolution of antichromatin autoantibodies in muring lupus implicates T–dependent immunization with self–antigen", J. Clin. Invest., vol. 91, pp. 1687–1696, 1993.
Casciola–Rosen, et al, "Autoantigens targeted in systemic lupus erythematosus are clustered in two populations of surface structures on apoptotic kertinocytes", J. Exp. Med., vol. 179, pp. 1317–1330, 1994.

Casciola–Rosen, et al., "Specific cleavage of the 70–kDa protein component of the U1 small nuclear ribonucleoprotein is a characteristic biochemical feature of apoptotic cell death", J. Biol. Chem., vol. 269, pp. 30757–30760, 1994.
Casciola–Rosen, et al., "DNA–dependent protein kinase is one of a subset of autoantigens specifically cleaved early during apoptosis", J. Exp. Med., vol. 182, pp. 1625–1634, 1995.
Casciola–Rosen, et al., "Apopain/CPP32 cleaves proteins that are essential for cellular repair: A fundamental principal of apoptotic death", J. Exp.Med., vol. 183, pp. 1957–1964, 1996.
Casciola–Rosen, et al., "Ultraviolet light–induced keratinocyte apoptosis: A potential mechanism for the induction of skin lesions and autoantibody production in L.E.", Lupus, vol. 6, pp. 175–180, 1997.
Chinnaiyan, et al., "The Cell–Death Machine", Curr. Biol., vol. 6, pp. 555–562, 1996.
Chinnaiyan, et al., "Cytotoxic T–cell–derived granzyme B activates the apoptotic protease ICE–LAP3", Curr. Biol., vol. 6, pp. 897–899, 1996.
Darmon, et al., "Cleavage of CPP32 by granzyme B represents a critical role for granzyme B in the induction of target cell DNA fragmentation", J. Biol. Chem., vol. 271, pp. 21709–21712, 1996.
Darmon, et al., "Activation of the apoptotic protease CPP32 by cytotoxic T–cell–derived granzyme B", Nature, vol. 377, pp. 446–448, 1995.
Deveraux, et al., "X–linked IAP is a direct inhibitor of cell–death proteases", Nature, vol. 38, pp. 300–304, 1997.
Diamond, et al., "The role of somatic mutation int he pathogenic anti–DNA response", Ann. Rev. Immunol., vol. 10, 731–757, 1992.
Duan, et al., "ICE–LAP6, a novel member pf tje ICE/Ced–3 gene family, is activated by the cytotoxic T cell protease granzyme B", J. Biol. Chem., vol. 271, pp. 16720–16724.
Fernandes–Alnemri, et al., In vitro activation of CPP32 and Mch3 by Mch4, a novel human apoptotic cysteine protease containing two FADD–like domains, Proc. Natl. Acad. USA, vol. 93, pp. 7464–7469, 1996.
Froelich, et al., "Granzyme B perforin–mediated apoptosis of jurkat cells results in cleavage of poly(ADP–ribose)polymerase to the 89–kDa apoptotic fragment and less abundant 64–kDa fragment", Biochem. Biophys. Res. Commun., vol. 227, pp. 658–665. 1996.

(List continued on next page.)

*Primary Examiner*—Patrick J. Nolan
(74) *Attorney, Agent, or Firm*—Michael D. Yablonsky; Jack L. Tribble

(57) ABSTRACT

The present invention provides a method of producing autoantigens, compositions comprising autoantigenic fragments and methods of using autoantigenic fragments in the treatment of a condition associated with an autoimmune response. Also provided are assays for the detection or assessment of an autoimmune response.

5 Claims, 17 Drawing Sheets

PUBLICATIONS

Froelich, et al., "New paradigm for lymphocyte granule–mediated cytotoxicity—Target cells bind and internalize granzyme B, but an endosomolytic agent is necessage for cytoxolic delivery and subsequent apoptosis", J. Biol. Chem., vol. 271, pp. 29073–29079, 1996.

Ghayur, et al., "Proteolytic activation of protein kinase C d by an ICE/CED–3–like protease induces features of apoptosis", J. Exp. Med., vol. 184, pp. 2399–2404, 1996.

Greidinger, et al., "Sequential activation of three distinct ICE–like activities in Fas–ligated Jurkat cells.,"FEBS Lett., vol. 390, pp. 299–303, 1996.

Gu, et al., Processing and Activation of CMH–1 by Granzyme B., J. Biol. Chem., vol. 271, pp. 10816–10820, 1996.

Heusel, et al., "Cytocoxic lymphocytes require gramzyme B for the rapid induction of DNA fragmentation and apoptosis in allogeneic target cells", Cell, vol. 76, pp. 997–987, 1994.

Irmler, et al., Inhibition of death receptor signals by cellular FLIP, Nature, vol. 388, pp. 190–195, 1997.

Jacobson et al., "Programmed cell death in animal development", Cell, vol. 88, pp. 347–354, 1997.

Jans, et al., "Nuclear transport of granzyme B (fragmentin 2). Dependence on perforin in vivo and cytosolic factors in vitro", J. Biol. Chem., vol. 271, pp. 30781–30789, 1996.

Krajewska, et al., "Immunohistochemical analysis of in vivo patterns of expression of CPP32 (Caspase–3), a cell death protease", Cancer Res., vol. 57, pp. 1605–1613, 1997.

Krajewski, et al., "Immunolocalizationo f the ICE/Ced–3–family protease, CPP32 (Caspase–3), in non–Hodgkin's lymphomas, chronic lymphocytic leukemias, and reactive lymph nodes", Blood, vol. 89, pp. 3817–3825, 1997.

Lanzavecchia, et al., "How can cryptic epitopes trigger autoimmunity?", J. Exp. Med., vol. 181, pp. 1945–1948, 1995.

Liu, et al., "DFF, a heterodimeric protein that functions downstream of caspase–3 to trigger DNA fragmentation during apoptosis", Cell, vol. 89, pp. 175–184, 1997.

Mamula, et al., "The inability to process a self–peptide allows autoreactive T cells to escape tolerance", J. Exp. Med., vol. 177, pp. 567–571, 1993.

Martin, et al., "The cytotoxic cell protease gramzyme B initiates apoptosis in a cell–free system by proteolytic processing and activation of the ICE/CED–3 family protease, CPP32, via a novel two–step mechanism", EMBO J., vol. 15, pp. 2407–2416, 1996.

Martin, et al., "Protease activation during apoptosis: Death by a thousand cuts?", Cell, vol. 82, pp. 349–352, 1995.

McGahon, et al., Regulation of the Fas apoptotic cell death pathway by Abl. J. Biol. Chem., vol. 270, pp. 22625–22631, 1995.

Muzio, et al., "FLICE, a novel FADD–homologous ICE/CED–3–like protease, is recruited to the CD95 (Fas/APO–1) death–inducing signaling complex", Cell, vol. 85, pp. 817–827, 1996.

Nicholson, et al., Identification and inhibition of the ICE/CED–3 protease necessary for mammalian apoptosis, Nature, vol. 376, pp. 37–43, 1995.

Nicholson, et al., "Caspases: Killer proteases", TIBS, vol. 22, pp. 299–306, 1997.

Odake, et al., "Human and murine cytotoxic T lymphocyte serine proteases: Subsite mapping with peptide thioester substrates and inhibition of enzyme activity and cytolysis by isocoumarins", Biochemistry, vol. 30, pp. 2217–2227, 1991.

Pinkoski, et al., "Binding of granzyme B in the nucleus of target cells. Recognition of an 80 kDa protein", J. Biol. Chem., vol. 271, pp. 10225–10229, 1996.

Podack, et al., "Cytolytic T cell granules. Isolation, structural, biochemical and functional characterization", J. Med. Exp., vol. 160, pp. 695–710, 1984.

Poe, et al., "Human cytotoxic lymphocute gramzyme B: Its purification from granules and the characterization of substrace and inhibitor specificity", J. Biol. Chem., vol. 266, pp. 98–103, 1991.

Quan, et al., Proteolytic activation of the cell death protease Yama/CPP32 by granzyme B., Proc. Natl. Acad. Sci. USA, vol. 93, pp. 1972–1976, 1996.

Radic, et al., "Genetic and structural evidence for antigen selection of anti–DNA antibodies", Ann. Rev. Immunol., vol. 12, pp. 487–520, 1994.

Ramage, et al., "Expresion, refolding, and autocatalytic proteolytic processing of the interleukin–1b–converting enzyme precursor", J. Biol. Chem., vol. 270, pp. 9378–9383, 1995.

Salemi, et al., "HIVgp120 activates autoreactive CD4–specific T cell responses by unveiling of hidden CD4 peptides during processing", J. Exp. Med., vol. 181, pp. 2253–2257, 1995.

Sarin, et al., "Target cell lysis by CTL granule exocytosis is independent of ICE/Ced–3 family proteases", Immunity, vol. 6, pp. 209–215, 1997.

Sercarz, et al., Dominance and crypticity of T cell antigenic determinants, Ann. Rev. Immunol., vol. 11, pp. 729–766, 1993.

Sercarz, et al., "Mechanisms of autoimmunization: perspective from the mid–90s", Curr. Opin. Immunol., vol. 6, pp. 875–881, 1994.

Shi, et al., "Granzyme B(GraB) autonomously crosses the cell membrane and perforin initiates apoptosis and GraB nuclear localization", J. Exp. Med., vol. 185, pp. 855–866, 1997.

Shresta, et al., "Natural killer and lymphokine–activated killer cells require granzyme B for the rapid induction of apoptosis in susceptible target cells", Proc. Natl. Acad. Sci. USA, vol. 92, pp. 5679–5683, 1995.

Simitsek, et al., "Modulation of antigen processing by bound antibodies can boost or suppress class II major histocompatibility complex presentation of different T cell determinants", J. Exp. Med.,vol. 181, pp. 1957–1963, 1995.

Song, et al., "Interleukin–1b converting enzyme–like protease cleaves DNA–dependent protein kinase in cytotoxic T cell killing", J. Exp. Med., vol. 184, pp. 619–626, 1996.

Song, et al., DNA–dependent protein kinase catalytic subunit: A target for an ICE–like protease in apoptosis, EMBO J., vol. 15, pp. 3238–3246, 1996.

Srinivasula, et al., The Ced–3–interleukin 1b converting enzyme–like homolog Mch6 and the lamin–cleaving enzyme Mch2a are substrates for the apoptotic mediator CPP32, J. Biol. Chem., vol. 271, pp. 27099–27106, 1996.

Srinivasula, et al., FLAME–1, a novel FADD–like apoptotic molecule that regulates Fas/TNFR–1–induced apoptosis, J. Biol. Chem., vol. 272, pp. 18542–18545, 1997.

Talanian, et al., "Granule–mediated killing: Pathways for granzyme B–initiated apoptosis", J. Exp. Med., vol. 186, pp. 1323–1331, 1997.

Thome, et al., "Viral FLICE–inhibitory proteins (FLIPs) prevent apoptosis induced by death receptors", Nature, vol. 386, pp. 517–521, 1997.

Thompson, et al., "Apoptosis in the pathogenesis and treatment of disease", Science, vol. 267, pp. 1456–1562, 1995.

Thornberry, et al., "Interleukin–1 β converting enzyme: a novel cysteine protease required for IL–1β production and implicated in programmed cell death", Protein Science, vol. 4, pp. 3–12, 1995.

Thornberry, et al., "A combinatorial approach defines specificities of members of the caspase family and granzyme B–Functional, relationships established for key mediators of apoptosis", J. Biol. Chem., vol. 272, pp. 17907–17911, 1997.

Topalian, et al., "Tumor–specific cytolysis by lymphocytes infiltrating human melanomas", J. Immunol., vol. 142, pp. 3714–3725, 1989.

Trapani, et al, "Localization of granzyme B in the nucleus—A putative role in the mechanism of cytotoxic lymphocyte–mediated apoptosis", J. Biol. Chem., vol. 271, pp. 4127–4133, 1996.

Pietsch, et al., "Granzyme B", Methods Enzymol., vol. 244, pp. 80–87, 1994.

Wang, et al., "Identification and characterization of ICH–3, a member of the interleukin–1b converting enzyme (ICE)/Ced–3 family and an upstream regulator of ICE", J. Biol. Chem., vol. 271, pp. 20580–20587, 1996.

Watts, et al., "Suppressive effect of an antibody on processing of T cell epitopes", J. Exp. Med., vol. 178, pp. 1459–1463, 1993.

White, et al., "Life, death, and the pursuit of apoptosis", Genes Dev., vol. 10, pp. 1–15, 1996.

Xue, et al., "Inhibition of the *Caenorhavditis elegans* cell–death proteaseCED–3 by a CED–3 cleavage site in baculovirus p35 protein", Nature, vol. 377, pp. 248–251, 1995.

Yamin, et al., "Activation of the native 45–kDa precursor form of interleukin–1 β–converting enzyme", J. Biol. Chem., vol. 271, pp. 13273–13282, 1996.

Young, et al., Purification and characterization of a cytolytic pore–forming protein from granules of cloned lymphocutes with natural killer activity, Cell, vol. 44, pp. 849–859, 1986.

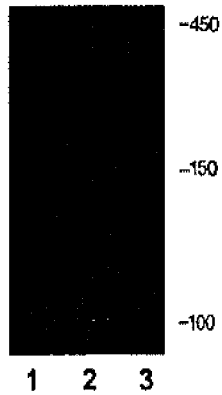
FIG.2A DNA-PKcs (anti-C-terminal Ab)
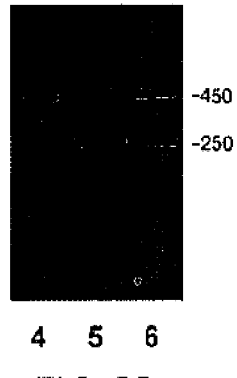
FIG.2B DNA-PKcs (anti-N-terminal Ab)
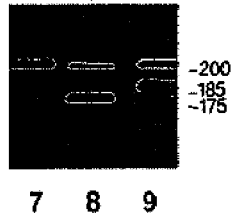
FIG.2C NuMA
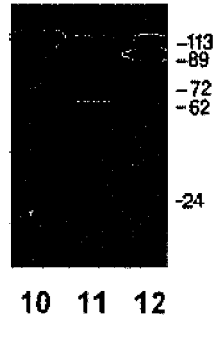
FIG.2D PARP

```
LOCUS       284337     2101 aa                    12-APR-1996
DEFINITION  NuMA protein - human.
ACCESSION   284337
PID         g284337
DBSOURCE    PIR:locus A42184
            summary: #length 2101 #molecular-weight 236296 #checksum 8715.
            PIR dates: 31-Dec-1993 #sequence_revision 31-Dec-1993#text_change
            12-Apr-1996.
KEYWORDS    .
SOURCE      human.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE   1  (residues 1 to2101)
  AUTHORS   Compton,D.A., Szilak,I. and Cleveland,D.W.
  TITLE     Primary structure of NuMA, an intranuclear protein that defines a
            novel pathway for segregation of proteins at mitosis
  JOURNAL   J. Cell Biol. 116 (6), 1395-1408 (1992)
  MEDLINE   92176238
REFERENCE   2  (residues 1 to 2101)
  AUTHORS   Tang,T.K., Tang,CJ., Chen,Y.L. and Wu,C.W.
  TITLE     Nuclear proteins of the bovine esophageal epithelium.II. The NuMA
            gene gives rise to multiple mRNAs and gene products reactive with
            monoclonal antibody WI
  JOURNAL   J. Cell. Sci. 104 (Pt 2), 249-260 (1993)
  MEDLINE   93280231
REFERENCE   3  (residues 1 to 2101)
  AUTHORS   Harborth,J., Weber,K. and Osborn,M.
  TITLE     Epitope mapping and direct visualization of the parallel,
            in-register arrangement of the double-stranded coiled-coil in the
            NuMA protein
  JOURNAL   EMBO J. 14 (11), 2447-2460 (1995)
  MEDLINE   95300777
FEATURES             Location/Qualifiers
     source          1..2101
                     /organism="Homo sapiens"
                     /db_xtef="taxon:9606"
     Protein         1..2101
                     /product="NuMA protein"
```

FIG.9A

```
   1 mtlhatrgaa llswvnslhv adpveavlql qdcsifikii drihgteegq qilkqpvser
  61 ldfvcsflqk nrkhpsspec lvsaqkvleg selelakmtm lllyhstmss ksprdweqfe
 121 ykiqaelavi lkfvldhedg lnlnedlenf lqkapvpstc sstfpeelsp pshqakreir
 181 flelqkvass ssgnnflsgs paspmgdilq tpqfqmrrlk kqladersnr delelelaen
 241 rklltekdaq iammqqridr lallnekqaa splepkelee lrdknesltm rlhetlkqcq
 301 dlkteksqmd rkinqlseen gdlsfklref ashlqqlqda lnelteehsk atqewlekqa
 361 qlekelsaal qdkkcleekn eilqgklsql eehlsqlqdn ppqekgevlg dvlqletlkq
 421 eaatlaannt qlgarvemle tergqqeakl laerghfeee kqqlsslitd lqssisnlsq
 481 akeeleqasq ahgarltaqv asltseltti natiqqqdqe laglkqqake kqaqlaqtlq
 541 qqeqasqglr hqveqlsssl kqkeqqlkev aekqeatrqd haqqlatsae ereaslrerd
 601 aalkqleale kekaakleil qqqlqvanea rdsaqtsvtq aqrekaelsr kveelqacve
 661 tarqegheaq aqvaelelql rseqqkatek ervaqekdql qeqlqalkes lkvtkgslee
 721 ekrraadale eqqrciselk aetrslvegh krerkeleee ragrkglear llqlgeahqa
 781 etevlrrela eamaaqhtae seceqlvkev aawrdgyeds qqeeaqygam fqeqlmtlke
 841 ecekarqelq eakekvagie shselqisrq qnklaelhan laralqqvqe kevraqklad
 901 dlstlqekma atskevarle tlvrkageqq etasrelvke paragdrqpe wleeqqgrqf
 961 cstqaalqam ereaegmgne lerlraalme sqgqqqeerg qqerevarlt qergraqadl
1021 alekaarael emrlqnalne qrvefatlqe alahalteke gkdqelaklr glesaqikel
1081 eelrqtvkql keglakkeke hasgsgaqse aagrteptgp klealraevs kleqqcqkqq
1141 eqadslersl eaerasraer dsaletlqgq leekaqelgh sqsalasaqr elaafrtkvq
1201 dhskaedewk aqvargrqea erknslissl eeevsilnrq vlekegeske lkrlvmaese
1261 ksqkleesca ccrqrqpatv pelqnaallc grrcrasgre aekgrvasen lrgeltsqae
1321 raeelgqelk awqekffqke qalstlqleh tstqalvsel lpakhlcqql qaeqaaekr
1381 hreeleqskq aagglraell raqrelgeli plrqkvaeqe rtaqqlraek asyaeqlsml
1441 kkahgllaee nrglgeranl grqflevelq qarekyvqel aavradaetr laevqreaqs
1501 tarelevmta kyegakvkvl eerqrfqeer qkltaqveel skkladsdqa skvqqqklka
1561 vqagggesqq eagrfqaqln elqaqlsqke qaashyklqm ekakthydak kqqnqelqeq
1621 lrsleqlqke nkelraeaer lghelqqagl ktkeaeqtcr hltaqvrsle aqvahadqql
1681 rdlgkfqvat dalksrepqa kpqldlsids ldlsceegtp lsitsklprt qpdgtsvpge
1741 paspisqrlp pkveslesly ftpiparsqa plessldslg dvfldsgrkt rsarrrttqi
1801 initmtkkld veepdsanss fystrsapas qaslratsst qslarlgspd ygnsallslp
1861 gyrpttrssa rrsqagvssg appgrnsfym gtcqdepegl ddwnriaelq qrnrvcpphl
1921 ktcyplesrp slslgtitde emktgdpqet lrrasmqpiq iaegtgittr qqrkrvslep
1981 hqgpgtpesk katscfprpm tprdrhegrk qstteaqkka apastkqadr rqsmefslln
2041 tpkklgnsll rrgaskkals kaspntrsgt rrspriattt asaataaaig atprakgkak
2101 h
```

FIG.9B

```
LOCUS 107227 2115 aa 10-NOV-1995
    DEFINITION   NuMA protein - human.
    ACCESSION 107227
    PID g107227
    DBSOURCE PIR: locus S23647
    summary: #length 2115 #molecular-weight 238273 #checksum 4391.
    PIR dates: 19-Feb-1994 #sequence_revision 10-Nov-1995 #text_change
    10-Nov-1995.
    KEYWORDS
    SOURCE human.
      ORGANISM Homo sapiens
    Eukaryotae; mitochondrial eukaryotes; Metazoa; Chordata;
    Vertebrata; Mammalia; Eutheria; Primates; Catarrhini; Hominidae;
    Homo.
    REFERENCE 1 (residues 1 to 2115)
      AUTHORS Yang,C.H., Lambie,E.J. and Snyder,M.
      TITLE  NuMA: an unusually long coiled-coil related protein in the
    mammalian nucleus
      JOURNAL J. Cell Biol. 116 (6), 1303-1317 (1992)
      MEDLINE 92176231
    FEATURES Location/Qualifiers
       source 1..2115
       /organism="Homo sapiens"
       /db_xref="taxon:9606"
        Protein 1..2115
       /product="NuMA protein"
```

FIG.10A

```
   1 mtlhatrgaa llswvnslhv adpveavlql qdcsifikii drihgteegq qilkqpvser
  61 ldfvcsflqk nrkhpsspec lvsaqkvleg selelakmtm lllyhstmss ksprdweqfe
 121 ykiqaelavi lkfvldhedg lnlnedlenf lqkapvpstc sstfpeelsp pshqakreir
 181 flelqkvass sagnnflsgs paspmgdilq tpqfqmrrlk kqladersnr delelelaen
 241 rklltekdaq iammqqridr lallnekqaa splepkelee lrdkneslm rlhetlkqcq
 301 dlkteksqmd rkinqlseen gdlsfklref ashlqqlqda lnelteehsk aCqewlekqa
 361 qlekelsaal qdkkcleekn eilqgklsql eehlsqlqdn ppqekgevlg dvlqletlkq
 421 eaatlaannt qlqarvemle tergqqeakl laerghfeee kqqlssliid lqssisnlsq
 481 akeeleqasq ahgarltaqv asltseittl natiqqqdqe laglkqqake kqaqlaqtlq
 541 qqeqasqglr hqveqlsssl kqkeqqlkev aekqeatrqd haqqlataae ereaslrerd
 601 aalkqleale kskaakleil qqqlqvanea rdsaqtsvtq aqrekaelsr kveelqacve
 661 tarqeqheaq aqvaelelql rseqqkatek ervaqekdql qeqlqalkes lkvtkgslee
 721 ekrraadale eqqrciselk aetrslveqh krerkeleee ragrkglear lqqlgeahqa
 781 etevlrrela eamsaqhtae seceqlvkev aawreryeds qqeeaqygam fqeqlmtlke
 841 ecekarqelq eakekvagie shselgisrq qnelaelhan laralqqvqe kevraqklad
 901 dlstlqekma atskevarle tlvrkageqq etasrelvke paragdrqpe wleeqqgrqf
 961 cstgaalgam ereaeqmgne lerlraalme sqgqqqeerg qqerevarlt qergraqadl
1021 alekaarael emrlqnalne qrvefatlqe alahalteke gkdqelaklr gleaaqikel
1081 eelrqtvkql keqlakkoke hasgsgaqse aagrteptgp klealraevs kleqqcqkqq
1141 eqadslersl eaerasraer dsaletlqgq leekaqelgh sqsalasaqr elaafrtkvq
1201 dhskaedewk aqvargrqea erknslissl eeevsilnrq vlekegeske lkrlvmaese
1261 ksqkleerlr llqaetasns araaerssal reevqslree aekqrvasen lrqeltsqae
1321 raeelgqelk awqekffqke qalstlqleh tstqalvsel lpakhlcqql qaeqaaaekr
1381 hreelegskq aagglraell raqrelgeli plrqkvaeqe rtaqqlraek asyaeqlsml
1441 kkahgllaee nrglgeranl grqfleveld qarekyvqel aavradaetr laevqreaqs
1501 tarelevmta kyegakvkvl eerqrfqeer qkltaqveql evfqreqtkq veelskklad
1561 sdqaskvqqq klkavqaqgg esqqeaqrlq aqlnelqaql sqkeqasehy klqmekakth
1621 ydakkqqnqe lqeqlrsloq lqkenkelra eaerlghelq qaglktkeae qtcrhltaqv
1681 rsleaqvaha dqqlrdlgkf qvatdalksr epqakpqldl sidsldlsce egtplsitsk
1741 lprtqpdgts vpgepaspis qrlppkvesl eslyftpipa rsqaplessl dslgdvfqds
1801 grktrsarrr ttqilnitmt kkldveepds anssfystrs apasqaslra tsstqslarl
1861 gspdygnsal lslpgyrptt rssarrsqag vssgappgrn sfymgtcqde peqlddwnri
1921 aelqqrnrvc pphlktcypl esrpslslgt itdeemktgd pqetlrrasm qpiqiaegtg
1981 ittrqqrkrv slephqgpgt peskkatscf prpmtprdrh egrkqstteq qkkaapastk
2041 qadrrgsmaf silntpkklg nsllrrgask kalskaspnt rsgtrrspri atttasaata
2101 aaigatprak gkakh
```

FIG.10B

```
LOCUS       1362789       4096 aa                    06-SEP-1996
DEFINITION  DNA-activated protein kinase, catalytic subunit - human.
ACCESSION   1362789
PID         g1362789
DBSOURCE    PIR: locus A57099
    summary: #length 4096 #molecular-weight 465420 #checksum 1795.
    genetic: #gene GDB:PRKDC ##cross-references GDB:234702
    #map_position 8q11.
    PIR dates: 27-Oct-1995 #sequence_revision 27-Oct-1995 text_change
      06-Sep-1996.
KEYWORDS    DNA binding; DNA recombination; DNA repair; nucleus;
    phosphotransferase.
SOURCE      human.
  ORGANISM  Homo sapiens
    Eukaryotae; mitochondrial eukaryotes; Metazoa; Chordata;
    Vertebrata; Mammalia; Eutheria; Prunates; Catarrhini; Hominidae;
    Homo.
REFERENCE   1 (residues 1 to 4096)
  AUTHORS   Sipley,J.D., Menninger,J.C.,Hartley,K.O.,Ward,D.C.,Jackson,S.P.
    and Anderson,C.W.
  TITLE     Gene for the catalytic subunit of the human DNA-activated protein
      kinase maps to the site of the XRCC7 gene on chromosome 8
  JOURNAL   Proc. Natl. Acad. Sci. U.S.A. 92 (16), 7515-7519 (1995)
  MEDLINE   95365397
REFERENCE   2 (residues 1 to 4096)
  AUTHORS   Hartley,K.O., Gell,D., Smith,G.C., Zhang,H., Divecha,N.,
    Connelly,M.A., Admon,A., Lees-Miller,S.P., Anderson,C.W. and
    Jackson,S.P.
  TITLE     DNA-dependent protein kinase catalytic subunit: a relative of
      phosphatidylinositol 3-kinase and the ataxia telangiectasia gene
      product
  JOURNAL   Cell 82 (5), 849-856 (1995)
  MEDLINE   95401275
FEATURES          Location/Qualifiers
    source    1..4096
      /organism="Homo sapiens"
      /db_ref="taxon:9606"
    Protein   1..4096
      /note="DNA-PK-cs"
      /product="DNA-activated protein kinase, catalytic subunit"
```

FIG.11A

```
   1 magsgagvrc sllrlqetls aadrcgaala ghqlirglgq ecvlssspav lalqtslvfs
  61 rdfgllvfvr kslnsiefre creeilkflc ifleRmgqki apysveiknt ctsvytkdra
 121 akckipaldl likllqtfrs srlmdefkig elfskfygel alkkkipdtv lekvyelIgl
 181 lgevhpsemi nnaenlfraf lgelktqmts avrepklpvl agclkglssl lcnftksmee
 241 dpgtsreifn fvlkairpqi dlkryavpsa glrlfalhas qfstclldny vslfevlikw
 301 cahtnvelkk aalsalesfl kqvsnmvakn aemhknklqy emeqfygiir nvdsnnkels
 361 iairgyglfa gpokvinakd vdfmyveliq rckqmfltqt dtgdyrvyqm psflqsvasv
 421 llyldtvpev ytpvlehlvv mqidsfpqys pkmqlvccra ivkvflalaa kgpvlrncis
 481 tvvhqgliri cakpvvlpkg pesesedhra sgevrtgkwk vptykdyvdl frhllssdqm
 541 mdsiladeaf fsvnsssesl nhllydefvk svlkivekld ltleiqtvgeq engdeapgv
 601 wmiptedpaa nlhpakpkdf safinlvefc reilpekqae ffepwvysfs yelilqstrl
 661 plisgfykll sitvrnakki kyfegvspks lkhspedpek yscfalfvkf gkevavkmkq
 721 ykdellascl tfllslphni ieldvrayvp alqmafklgl sytplaevgl naleewsiyi
 781 drhvmqpyyk dilpcldgyl ktsalsdetk nnwevsalsr aaqkgfnkvv lkhlkktknl
 841 ssneaislee irirvvqmlg slggqinknl ltvtssdemm ksyvawdrek rlsfavpfre
 901 mkpvifldvf lprvtelalt asdrqtkvaa cellhsmvmf mlgkatqmpe ggqgappmyq
 961 lykrtfpvll rlacdvdqvt rqlyeplvmq lihwftnnhk fesqdtvsll eaildgivdp
1021 vdstlrdfcg rcireflkws ikqitpqqqe kspvntkslf krlyslalhp nafkrlgasl
1081 afnniyrefr eeeslveqfv fealviymes lalahadeks lgtiqqccda idhlcriiek
1141 khvslnkakk rrlprgfpps aslclldlvk wllahcgrpq tecrhksiel fykfvpllpg
1201 nrspnlwlkd vlkeegvsfl intfegggcg qpsgilagpt llylrgpfsl qatlcwldll
1261 laalecyntf igertvgalq vlgteaqssl lkavaffles iamhdiiaae kcfgtgaagn
1321 rtspqegery nyskctvvvr imeftttlln tspegwkllk kdlcnthlmr vlvqtlcepa
1381 sigfnigdvq vmahlpdvcv nlmkalkmsp ykdilethlr ekitaqsiee lcavnlygpd
1441 aqvdrsrlaa vvsackqlhr agllhnilps qstdlhhsvg tellslvykg iapgderqcl
1501 psldlsckql asgllelafa fgglcerlvs lllnpavlst aslgssqgsv ihfshgeyfy
1561 slfsetinte llknldlavl elmqssvdnt kmvsavlngm ldqsfreran qkhqglklat
1621 tilqhwkkcd swwakdsple tkmavlalla kilgidssvs fntshgsfpe vfttyislla
1681 dtkldlhlkg qavtllpfft sltggsleel rrvleqliva hfpmqsrefp pgtprfnnyv
1741 dcmkkfldal elsqspmlle lmtevlcreq qhvmeelfqs sfrriarrgs cvtqvglles
1801 vyemfrkddp rlsftrqsfv drslltllwh csldalreff stivvdaidv lksrftklne
1861 stfdtqitkk mgyykildvm ysrlpkddvh akeskinqvf hgscitegne ltktliklcy
1921 daftenmage nqllerrrly hcaayncais viccvfnelk fyqgflfsek peknllifen
1981 lidlkrrynf pvevevpmer kkkyieirke areaangdsd gpsymssIsy ladstlseem
2041 sqfdfstgvq sysyssqdpr patgrfrrre qrdptvhddv lelemdelnr hecmopltal
2101 vkhmbrslgp pqgeedsvpr dlpswmkflh gklgnpivpl nirlflaklv inteevfrpy
2161 akhwlspllq laasenngge gihymvveiv atilswtgla tptgvpkdev lanrllnflm
2221 khvfhpkrav frhnleiikt lvecwkdcls ipyrlifekf sgkdpnskdn svgiqllgiv
2281 mandlppydp qcgiqsseyf qalvnnmefv rykevyaaaa evlglilryv merknilees
2341 lcelvakqlk qhqntmedkf ivclnkvtks fppladrfmn avfflIpkfh gvlktlclev
2401 vlcrvegmte lyfqlskskdf vqvmrhrder qkvcldiiyk mmpklkpvel rellnpvvef
2461 vshpsttcre qmynilmwih dnyrdpeset dndsqeifkl akdvliqgli denpglqlii
2521 rnfwshetrl pentldrlla lnslyspkie vhflslatnf llemtsmspd ypnpmfehpl
2581 secefqeyti dsdwrfrstv ltpmfvetqa sqgtlqtrtq egslsarwpv agqiratqqq
2641 hdftltqtad grssfdwltg sstdplvdht spssdsllfa hkrserlqra plksvgpdfg
2701 kkrlglpgde vdnkvkgaag rtdllrlrrr fmrdqeklsl myarkgvaeq krekeiksel
```

FIG.11B

```
2761 kmkqdagvvl yrsyrhgdlp diqikhssli tplqavaqrd piiakqlfss lfsgilkemd
2821 kfktlseknn itqkllqdfn rflnttfsff ppfvsciqdi scqhaallsl dpaavsagcl
2881 aslqqpvgir lleeallrll paelpakrvr gkarlppdvl rwvelaklyr sigeydvlrg
2941 iftseigtkq itqsallaea rsdysesakq ydealnkqdw vdgepteaek dfwelasldc
3001 ynhlaewksl eycstasids enppdlnkiw sepfyqetyl pymirsklkl llqgeadqsl
3061 ltfidkamhg elqkailelh ysqelsllyl lqddvdraky yigngiqsfm qnyssidvll
3121 hqsrltklqs vqalteiqef isfiskqgnl seqvplkrll ntwtnrypda kmdpmniwdd
3181 iitnrcffls kieekltplp ednsmnvdqd gdpsdrmevq eqeedissli rsckfsmkmk
3241 midsarkqnn fslamkllke lhkesktrdd wlvswvqsyc rlshcrsrsq gcseqvltvl
3301 ktvslldenn vssylxknil afrdqnillg ttyriianal ssepaclaei eedkarrile
3361 lsgsssedse kviaglyqra fqhlseavqa aseeagppsw scgpaagvid aymtladfcd
3421 qqlrkeeena svtdsaelqa ypalw ekml kalklnsnea rlkfprllgi ierypeetls
3481 lmtkeissvp cwqfiswish mvalldkdqa vavqhsveei tdnypqaivy pfiissesys
3541 fkdtstghkn kefvariksk ldqggviqdf inaldqlsnp ellfkdwsnd vraelaktpv
3601 nkkniekmye rmyaalgdpk apglgafrrk fiqtfgkefd khfgkggskl lrmklsdfnd
3661 itnmlllkmn kdskppgnlk ecspwmsdfk veflrnelei pggydgrgkp lpeyhvriag
3721 fdervtvmas lrrpkriiir ghderehpfl vkggedlrqd qrveqlfqvm ngilaqdsac
3781 sqralqlrty svvpmtssdp rappceykdw ltkmsgkhdv gaymlmykga nrtetvtser
3841 kreskvpadl lkrafvrmst speaflalrs hfasshalic ishwilgigd rhlnnfmvam
3901 etggvigidf ghafgsatqf lpvpelmpfr ltrqfinlml pmketglmys imvhalrafr
3961 sdpglltntm dvfvkepsfd wknfeqkmlk kggswiqein vaeknwyprq kicyakrkla
4021 ganpavitcd elllghekap afrdyvavar gskdhniraq epesqlseet qvkcimdgat
4081 dpnilgrtwe gwepwm
```

FIG.11C

```
LOCUS      130781    1014aa           01-NOV-1997
DEFINITION POLY (ADP-RIBOSE) POLYMERASE (PARP) (ADPRT) (NAD(+)
           ADP-RIBOSYLTRANSFERASE) (POLY(ADP-RIBOSE) SYNTEHTASE).
ACCESSION  130781
PID        g130781
DBSOURCE SWISS-PROT: locus PPOL_HUMAN, accession P09874
     class: standard.
     created: Mar 1, 1989.
     sequence updated: Dec 1, 1992.
     annotation updated: Nov 1, 1997.
     xrefs: gi: 510112, gi: 1017423, gi: 190166, gi: 190167, gi: 337423,
     gi: 337424, gi: 178151, gi: 178152, gi: 190266, gi: 190267, gi:
     178188, gi: 178190, gi: 189533, gi: 189534, gi: 35286, gi: 825702,
     gi: 35288, gi: 189535, gi: 189536, gi: 88229, gi: 88227, gi:
     627553, gi: 107162, gi: 107160, gi: 482956, gi: 420073, gi: 107158
     xrefs (non-sequence databases): AAR;EIUS/GHENT-2DPAGE 1620,
MIM
     173870, MIM 173871, PROSITE PS00347, PROSITE PS50064
KEYWORDS TRANSFERASE; GLYCOSYLTRANSFERASE; NAD; DNA-BINDING; NUCLEAR
     PROTEIN; ADP-RIBOSYLATION; ZINC-FINGER; ZINC.
SOURCE    human.
  ORGANISM  Homo sapiens
     Eukaryotae; Metazoa; Chordata; Vertebrata; Mammalia; Eutheria;
     Primates; Catarrhini; Hominidae; Homo.
REFERENCE 1 (residues 1 to 1014)
  AUTHORS Auer,B., Nagl,U., Herzog,H., Schneider,R. and Schweiger,M.
  TITLE   Human nuclear NAD+ ADP-ribosyltransferase(polymerizing):
          organization of the gene
  JOURNAL DNA 8 (8), 575-580 (1989)
  MEDLINE 90091744
  REMARK SEQUENCE FROM N.A.
REFERENCE 2 (residues 1 to 1014)
  AUTHORS Uchida,K, Morita,T., Sato,T., Ogura,T., Yamashita,R.,
Noguchi,S.,
          Suzuki,H., Nyunoya,H., Miwa,M. and Sugimura,T.
  TITLE Nucleotide sequence of a full-length cDNA for human fibroblast
        poly(ADP-nbose) polymerase
  JOURNAL Biochem. Biophys. Res. Commun. 148 (2), 617~22 (1987)
  MEDLINE 88076933
  REMARK SEQUENCE FROM N.A.
     TISSUE=FIBROBLAST
```

FIG.12A

```
  1 maessdklyr veyaksgras ckkcsesipk dslrmalmvq spmfdgkvph wyhfscfwkv
 61 ghsirhpdve vdgfselrwd dqqkvkktae aggvlgkgqd gigskaektl gdfaaeyaks
121 nrstckgcme kiekgqvrls kkmvdpekpq lgmidrwyhp gcfvknreel gfrpeysasq
181 lkgfsllate dkealkkqlp gvksegkrkg devdgvdeva kkkskkekdk dsklekalka
241 qndliwnikd elkkvcstnd lkellifnkq qvpegesail drvadgmvfg allpceecag
301 qlvfkedayy ctgdvtawtk cmvktqtpnr kewvtpkefr eisylkklkv kkqdrifppe
361 tsasvaatpp pstasapaav nssasadkpl snmkiltlgk lsrnkdevka mieklggklt
421 gtankaslci stkkevekmn kkmeevkean irvvsedflq dvsastkslq elflahilsp
481 wgaevkaepv evvaprgksg aalskkskgq vkeeginkse krmkltlkgg aavdpdagle
541 hsahvlekgg kvfeatlplv divkgtnsyy klqlleddke nrywifrawg rvgtvigsnk
601 legmpskeda iehfmklyee ktgnawhakn ftkypkkfyp leidygqdee avkkltvnpg
661 tksklpkpvq dlikmifdve smkkamveye idlqkmplgk lskrqiqaay silsevqqav
721 sqgssdsqil dlsnrfytli phdfgmkkpp llnnadsvqa kvemldnlld ievaysllrg
781 gsddsskdpi dvnyeklktd ikvvdrdsee aeiirkyvkn thatthnayd levidifkie
841 regecqrykp fkqlhnrrll whgerttnfa gilaqglria ppeapvtgym fgkgiyfadm
901 vsksanycht sqgdpiglil lgevalgnmy elkhashisk lpkgkhsvkg lgkttpdpsa
961 nisldgvdvp lgtgissqvn dtsllyneyi vydiaqvnlk yllklkfnfk tslw
```

FIG.12B

AUTOANTIGENIC FRAGMENTS, METHODS AND ASSAYS

CROSS-REFERENCE TO RELATED APPLICATIONS

This applications claims the benefit of U.S. Provisional Application Ser. No. 60/082,643, filed Apr. 22, 1998.

STATEMENT REGARDING FEDERALLY-SPONSORED R&D

This invention was made in part under Federally Sponsored Research. The U.S. Government may have certain rights in this invention.

FIELD OF THE INVENTION

This invention relates to the production of autoantigenic fragments from autoantigens and the uses of the autoantigenic fragments.

BACKGROUND OF THE INVENTION

The mature immune system of animals differentiates between self-molecules and non-self-molecules and mounts an immune response only against the latter. The immune system learns which molecules are self through constant exposure to those molecules that are normally a part of the animal. Thus, the mature immune system is tolerized to the presence of molecules that are self. However, the immune system is not tolerized to molecules that are newly presented in the animal. These molecules can be antigens and thereby stimulate an immune response against them. Commonly, newly presented antigens are from an extracorporeal source, such as an infection. In this case, the immune response helps to destroy the source of the antigens and thereby clear the infection from the body.

Newly presented antigens are produced in vivo through the degradation of cellular components. When the immune system recognizes these degradation products of self molecules as "non-self" antigens, an immune response can be mounted against them and an autoimmune disease can develop. Thus, these antigens are members of the class of molecules generally referred to as autoantigens and the antibodies produced against them are referred to as autoantibodies. For clarity herein, autoantigen is used to refer to the complete self molecule as found in the body. Autoantigenic fragment is used to refer to the degradation product of the autoantigen. Thus it is when an epitope is presented to the immune system as autoantigenic fragment that an immune response is elicited. Once elicited, the immune response can target the autoantigenic fragment, the autoantigen, or both.

Autoimmune diseases are diseases in which a specific immune response to self-molecules occurs, often leading to tissue and organ damage and dysfunction. The diseases can be organ-specific (e.g. Type I diabetes mellitus, thyroiditis, myasthenia gravis, primary biliary cirrhosis) or systemic in nature (e.g. systemic lupus erythematosus, rheumatoid arthritis, polymyositis, dermatomyositis, Sjogren's syndrome, scleroderma, and graft-vs.-host disease).

One source of autoantigenic fragments is cleavage of an autoantigen during apoptosis. Apoptosis is a morphologically and biochemically distinct form of cell death that occurs in many different cell types during a wide range of physiologic and pathologic circumstances (reviewed in (Jacobson et al., 1997; Thompson, 1995; White, 1996)). Studies report that specific proteolysis catalyzed by a novel family of cysteine proteases is of critical importance in mediating apoptosis (Chinnaiyan and Dixit, 1996a; Martin and Green, 1995; Thornberry and Molineaux, 1995). These proteases (termed caspases), cleave downstream substrates after a consensus tetrapeptide sequence ending with aspartic acid ($P_1$). The caspases are synthesized as inactive precursors that require specific proteolytic cleavage after an aspartic acid residue for activation (reviewed in (Nicholson and Thornberry, 1997)).

Granzyme B, a serine protease found in the cytoplasmic granules of cytotoxic T lymphocytes (CTL) and natural killer (NK) cells, has a similar requirement to caspases, for aspartic acid in the substrate $P_1$ position (Odake et al., 1991; Poe et al., 1991). Studies have reported that granzyme B plays an important role in inducing apoptotic nuclear changes in target cells during granule exocytosis induced cytotoxicity (Darmon et al., 1996; Heusel et al., 1994; Sarin et al., 1997; Shresta et al., 1995; Talanian et al., 1997).

Granzyme B is described as catalyzing the cleavage and activation of several caspases (Chinnaiyan et al., 1996b; Darmon et al., 1995; Duan et al., 1996; Fernandes-Alnemri et al., 1996; Gu et al., 1996; Martin et al., 1996; Muzio et al., 1996; Quan et al., 1996; Sarin et al., 1997; Song et al., 1996a; Srinivasula et al., 1996; Talanian et al., 1997; Wang et al., 1996). Granzyme B also initiates caspase-independent pathways which contribute to target cell death. However, while several candidates for these additional pathways exist, they remain largely undefined (Sarin et al., 1997; Talanian et al., 1997).

One candidate pathway is the direct proteolysis of death substrates by granzyme B, although efficient non-caspase cellular substrates for this protease have not yet been identified. Initial studies have indicated that the cleavage of PARP, U1-70 kDa and lamin B observed during granzyme B-induced cell death is catalyzed by caspases, rather than directly by granzyme B (Darmon et al., 1995; Martin et al., 1996; Talanian et al., 1997), but the effects of granzyme B on other caspase substrates in vitro and during granule-induced cytotoxicity have not been extensively studied.

BRIEF DESCRIPTION OF THE DRAWINGS

FIG. 2. Cleavage of autoantigens in vitro with purified granzyme B or caspase-3 yields different fragments. Reactions containing 30 nM purified DNA-$PK_{cs}$ (lanes 1–3), endogenous DNA-$PK_{cs}$ and NuMA in HeLa lysate (lanes 4–9) or [$^{35}S$]methionine-labeled PARP (lanes 10–12) were incubated with the following amounts of granzyme B: 1.25 nM (lane 2); 12.5 nM (lanes 5 & 8) or 50 nM (lane 11). Similar experiments were performed with these substrates using the following amounts of caspase-3: 42 pM (lanes 3 & 12) or 100 pM (lanes 6 & 9). Reaction mixtures were incubated at 37° C. for 15 min. (granzyme B reactions) or 60 min. (caspase-3 reactions). Note that 100 nM Ac-DEVD-CHO was added when granzyme B was used to cleave DNA-$PK_{cs}$ and NuMA in HeLa cell lysates, to prevent activation of HeLa cell caspases. Intact and cleaved NuMA and DNA-$PK_{cs}$ were visualized by immunoblotting, and PARP was visualized by autoradiography. In the case of DNA-PK$_{cs}$, blots obtained using monoclonal antibodies 25-4 (directed against the C-terminus) and 18-2 (directed against the N-terminus) are shown in lanes (1–3) and (4–6), respectively.

FIGS. 9A–9B shows a 2101 amino acid sequence of NuMA as found on Entrez at ACCESSION 284337; PID g284337; DBSOURCE PIR: locus A42184 SEQ ID NO:32.

FIGS. 10A–10B shows a 2115 amino acid sequence of NuMA as found on Entrez at ACCESSION 107227, PID g107227; DBSOURCE PIR: locus S23647 SEQ ID NO:33.

FIGS. 11A–11C shows the amino acid sequence of DNA PK$_{cs}$ as found on Entrez at ACCESSION 1362789; PID g1362789; DBSOURCE PIR: locus A57099 SEQ ID NO:34.

FIGS. 12A–12B shows the amino acid sequence of PARP as found on Entrez at ACCESSION 130781; PID g130781; DBSOURCE SWISS-PROT: locus PPOL_HUMAN, accession P09874 (listing only references 1 & 2 of 12) SEQ ID NO:35.

SUMMARY OF THE INVENTION

Figure 1A:
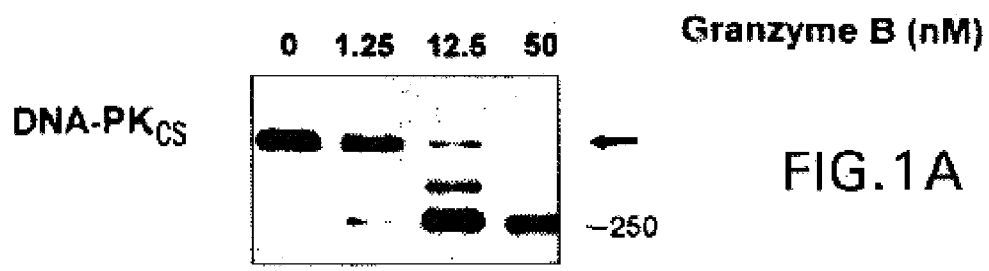
FIG. 1. Granzyme B cleaves purified DNA-$PK_{cs}$, NuMA, PARP and caspases 3 and 7 in vitro with different efficiencies. Reactions containing 0–12.5 nM granzyme B (for DNA-$PK_{cs}$ and NuMA)or 0–50 nM granzyme B (for caspases 3 and 7 and PARP) were performed as described in Example 1. Cleavage fragments were detected by fluorography or immunoblotting (monoclonal antibody 18-2 was used to detect DNA-$PK_{cs}$). On the right side of each panel, the SDS-PAGE migration positions of the intact molecules are denoted by arrows, and the fragment sizes are indicated.
Figure 1B:
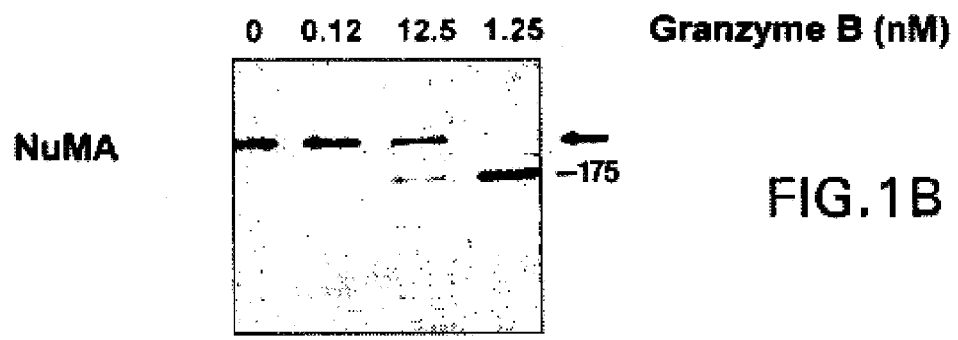
Figure 1C:
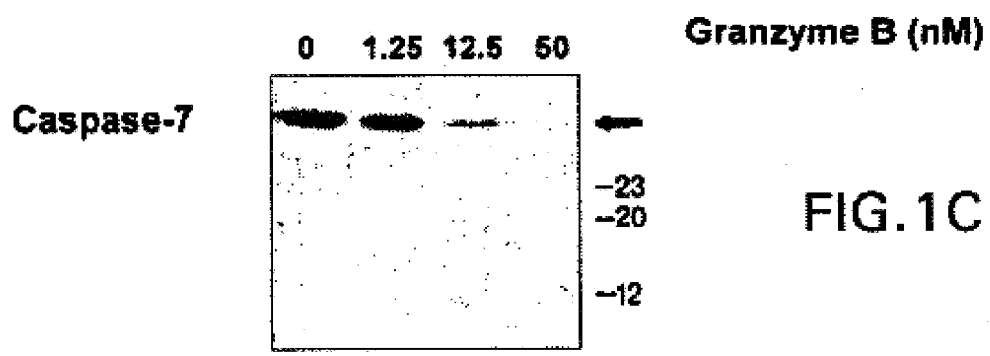
Figure 1D:
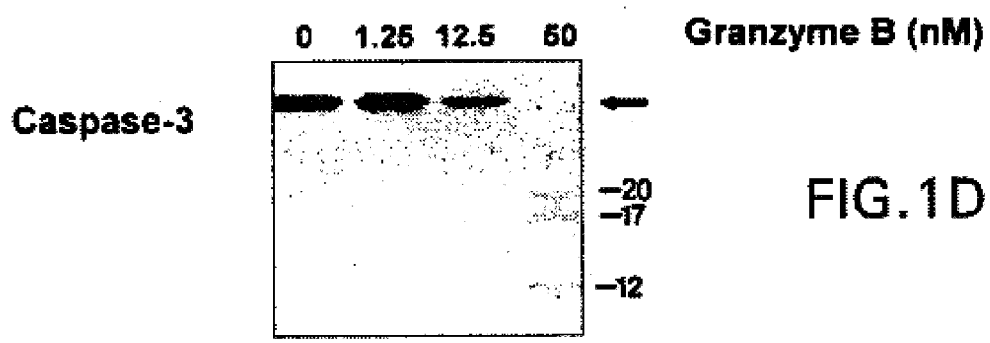
Figure 1E:
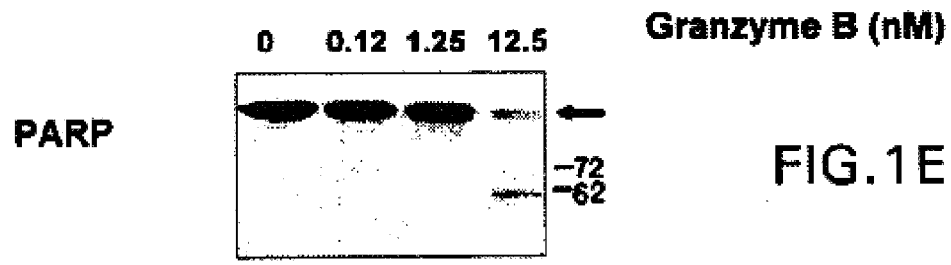

The present invention provides autoantigenic fragments and methods for their use in the treatment of autoimmune disease. Also provided are assays for detecting an autoimmune condition in an animal, including the presence of an autoimmune disease.

Caspase-mediated proteolysis of downstream substrates is a critical element of the central execution pathway common to all forms of apoptosis studied to date. While cytolytic lymphocyte granule-induced cell death activates this caspase-dependent pathway, recent studies have also provided evidence for caspase-independent pathways in this form of cell death. However, non-caspase substrates for granzyme B (and potentially other granule proteases) during granule-induced cell death have not previously been defined. The present invention makes use of the observation that cellular components are directly and efficiently cleaved by granule contents, including in particular granzyme B, in vitro and in vivo, and that this cleavage leads to the generation of unique autoantigenic fragments not observed during other forms of apoptosis. This direct, caspase-independent ability of granzyme B to cleave downstream death substrates to autoantigenic fragments is an apoptotic effector mechanism which is insensitive to inhibitors of the signaling or execution components of the endogenous apoptotic cascade.

An aspect of this invention is a composition that includes at least one autoantigenic fragment. The autoantigenic fragment is produced by the action of a granule enzyme on an autoantigen. In a preferred embodiment, the enzyme is a granule enzyme of CTL, NK or LAK cell granules. In a most preferred embodiment, the enzyme is granzyme B and the antigenic fragment is produced by the cleavage of the autoantigen by granzyme B at a site that is not cleaved by a caspase. In a preferred embodiment the autoantigen is DNA $PK_{cs}$, PARP or NuMA. In a most preferred embodiment, the autoantigenic fragment is one or more of DNA-$PK_{cs}$ from amino acid 2699 to 4096 SEQ ID NO:34; DNA-$PK_{cs}$ from amino acid 3211 to 4096 SEQ ID NO:34; PARP from amino acid 1 to 537 SEQ ID NO:35; PARP from amino acid 538 to 1004 SEQ ID NO:35; NuMA from amino acid 412 to 2111 SEQ ID NO:33 and NuMA from amino acid 1 to 1799 SEQ ID NO:33.

An aspect of this invention is a pharmaceutical composition made with one or more purified and isolated autoantigenic fragments. In a preferred embodiment, the autoantigenic fragment has at least one end derived from granzyme B cleavage at a site in the autoantigen that is not cleaved by a caspase. A pharmaceutically acceptable carrier is also included. In a preferred embodiment the composition includes one of more of the following autoantigenic fragments: DNA-$PK_{cs}$ from amino acids 2699 to 4096 SEQ ID NO:34; DNA-$PK_{cs}$ from amino acids 3211 to 4096 SEQ ID NO:34; PARP from amino acid 1 to 537 SEQ ID NO:35; PARP from amino acids 538 to 1004 SEQ ID NO:35; NuMA from amino acids 412 to 2111 SEQ ID NO:33 and NuMA from amino acids 1 to 1799 SEQ ID NO:33. In another preferred embodiment the pharmaceutical composition includes one or more autoantigenic fragments derived from a malignant cell.

An aspect of this invention is a method of treating a patient in need of treatment for an autoimmune disease by administering to the patient an autoantigenic fragment of this invention. The autoimmune disease can be organ specific, e.g., Type I diabetes mellitus, thyroiditis, myasthenia gravis, primary biliary cirrhosis, or systemic in nature e.g. systemic lupus erythematosus, rheumatoid arthritis, polymyositis, dermatomyositis, Sjogrenís syndrome, scleroderma, and graft-vs.-host disease. In one preferred embodiment, the treatment is therapeutic. For example, a patient suffering from an immune disease can be administered an autoantigenic fragment by contacting the sera of the patient with the fragment under conditions that allow the binding of autoantibodies in the sera to bind to the fragment. In this embodiment, the level of autoantibodies circulating in the patient can be reduced. In another embodiment the treatment is prophylactic. In this embodiment, a patient who is at risk of developing an autoimmune disease is tolerized to at least one autoantigenic fragment. Thereafter, the risk of, or severity of an autoimmune disease arising upon the later production of the autoantigenic fragment in vivo, is reduced or eliminated. In a preferred embodiment, a patient is tolerized by identifying a target tissue to which an autoimmune disease can arise, providing at least one granule enzyme, contacting the granule enzyme with cells from the target tissue to produce autoantigenic fragments of autoantigens present in the cells. The autoantigenic fragments are then administered to the patient to tolerize the patient to the presence of the fragments. In preferred embodiments, the autoantigens can be partly or wholly purified from the cells of the target tissue. The granule enzyme can also be partly or wholly purified before contacting with the autoantigens. The enzyme can also be made by recombinant methods. In a preferred embodiment, the autoantigenic fragments are partly or wholly purified before they are administered to the patient. In prophylactic methods of tolerizing, the autoantigenic fragments are administered in pharmaceutically acceptable compositions that are designed not to raise an immune response to the fragments, i.e., no immunostimmulatory adjuvants are administered with the fragments. In a preferred embodiment, the treatment uses one or more of the following autoantigenic fragments: DNA-$PK_{cs}$ from amino acids 2699 to 4096 SEQ ID NO:34; DNA-$PK_{cs}$ from amino acids 3211 to 4096 SEQ ID NO:34; PARP from amino acid 1 to 537 SEQ ID NO:35; PARP from amino acids 538 to 1004 SEQ ID NO:35; NuMA from amino acids 412 to 2111 SEQ ID NO:32 and NuMA from amino acids 1 to 1799 SEQ ID NO:32.

An aspect of this invention is a method of treating a patient in need of treatment for a malignancy. In a preferred embodiment, at least one enzyme of a lymphocyte granule is contacted with the malignant cells from the patient. This can produce a mixture containing autoantigenic fragments derived from the malignant cells. The fragments are administered to the patient, preferably with an adjuvant, to stimulate an immune response against the malignant cells.

An aspect of this invention is an assay for the detection of an autoantigenic fragment in a patient. In one embodiment, the presence or absence of the fragment in a patient sample is an indication of the presence or absence of an autoimmune condition in the patient. In a preferred embodiment, a sample from the patient is contacted with an antibody that specifically binds to a cryptic epitope of an autoantigenic fragment. Preferably, the fragment has at least one terminus derived from the cleavage of an autoantigen by granzyme B at a site that is not cleaved by a caspase. The presence or absence of the binding of the antibody to the autoantigenic fragment is then assessed as an indication of the presence or absence of an autoimmune condition in a patient. In an alternative embodiment, the detection of an antibody that binds an autoantigenic fragment is an indication of the presence or absence of an autoimmune condition in the patient. In this embodiment a sample from the patient is contacted with an autoantigenic fragment having at least one terminus derived from cleavage by a granule enzyme. Detection of the presence or absence of the binding of an antibody in the sample to the autoantigenic fragment is an indication of the presence or absence of an autoimmune condition in the patient.

An aspect of this invention is a method of making an autoantigenic fragment from an autoantigen. In a preferred embodiment, one isolates cells containing at least one autoantigen and contacts the cells with a lymphocyte granule enzyme to produce a mixture containing at least one autoantigenic fragment. In a further embodiment one isolates at least one autoantigenic fragment from the mixture. In a preferred embodiment one purifies at least one autoantigen and contacts the purified autoantigen with granzyme B. In a further preferred embodiment, one purifies one or more of the following autoantigens for contacting with granzyme B: DNA-$PK_{cs}$, PARP and NuMA. In each embodiment the granule enzyme can isolated from the granules of a lymphocyte, e.g., a cytotoxic T lymphocyte (CTL), a natural killer cell (NK), a lymphokine activated killer cell (LAK) or cells of the YT cell line.

In all aspects of this invention, granzyme B can be used in particular embodiments. the enzyme can be purified from the granules of granule containing lymphocytes or can be prepared by recombinant techniques.

Definitions

As used herein, "treatment" includes the therapeutic or prophylactic application of a composition to a patient. A treatment can prevent, moderate or cure a disease in the patient. A disease is moderated in a patient when the treatment lessens the severity or frequency of at least one symptom associated with the disease. A treatment can moderate a disease by: (1) prophylactic administration of a composition to a patient free of a disease to lessen the impact of at least one symptom of the disease when it does occur or (2) therapeutic administration to a patient having a disease to lessen at least one symptom of the disease.

As used herein, a "patient" is an animal, particularly including a human.

As used herein, an "autoimmune condition" is the presence of, or the predisposition for the development of, an autoimmune disease or an autoimmune response in a patient.

As used herein, an "autoantigen" is a cellular molecule and usually is a protein. An autoantigen is typically not antigenic because the immune system is tolerized to its presence in the body under normal conditions. An autoantigen will typically include at least one cryptic epitope. An autoantigen can be produced by natural cells, using recombinant methods, or through chemical synthesis, as appropriate.

As used herein, an "autoantigenic fragment" is a degradation product of an autoantigen. An autoantigenic fragment is antigenic because the immune system is not tolerized to its presence in the body. Autoantigenic fragments usually display cryptic epitopes to the immune system. An autoantigenic fragment can be produced by natural cells, through the action of at least one granule enzyme in a cellular or cell free system, using recombinant methods, or through chemical synthesis, as appropriate.

As used herein, an "autoantibody" is an antibody produced by the immune system of an animal in response to the present of an autoantigenic fragment. An autoantibody can bind to the autoantigenic fragment, the autoantigen from which the fragment is derived, or both.

As used herein, a "granule containing lymphocyte" is meant to include all lymphocytes that contain granules. In particular, the term is used to include the family of cell types sometimes referred to as cytotoxic lymphocytes, to include cell lines derived from these cells and to include cytotoxic lymphocyte-like cell lines, preferably the YT cell line. Preferred cells are the granule containing lymphocytes known in the art as cytotoxic T lymphocytes (CTL), natural killer cells (NK) and lymphokine activated killer cells (LAK).

As used herein, a "lymphocyte granule enzyme" or "granule enzyme" is an enzyme that is found in the granules of a granule containing lymphocyte. A granule enzyme can be purified from a lymphocyte granule by methods commonly employed in the art of protein purification. Additionally, a granule enzyme can be prepared by cloning the gene for the enzyme and the enzyme then is prepared using methods commonly used in the production of recombinant enzymes.

As used herein, "purified" and/or "isolated" are used interchangeably to stand for the proposition that the protein(s) and polypeptide(s), or respective fragment(s) thereof in question has been removed from its in vivo environment. A protein or fragment thereof is considered "purified" and/or "isolated" when it is obtained at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. A protein is sometimes referred to as partly purified if it is at least purified or isolated but it is not essentially pure. A chemically synthesized protein is considered to be substantially purified when purified from its chemical precursors. A purified or isolated protein can be manipulated by the skilled artisan, such as but not limited to obtaining the protein or protein fragment in quantities that afford the opportunity to generate polyclonal antibodies, monoclonal antibodies, amino acid sequencing, and peptide digestion. Therefore, the autoantigenic fragments claimed herein can be present in cell lysates or in a substantially or essentially pure form.

Abbreviations

Ac-DEVD-CHO, N-(N-Ac-Asp-Glu-Val)-3-amino-4-oxobutanoic acid SEQ ID NO:1; Ac-YVAD-CHO, N-(N-Ac-Tyr-Val-Ala)-3-amino-4-oxobutanoic acid SEQ ID NO:26; CTL, cytotoxic T lymphocytes; DNA-PK$_{cs}$, DNA-dependent protein kinase catalytic subunit; LAK cells, lymphokine-activated killer cells; NK cells, natural killer cells; NuMA, nuclear mitotic apparatus protein; PARP, poly(ADP-ribose)polymerase; PI, propidium iodide

DETAILED DESCRIPTION OF THE INVENTION

The present invention provides autoantigenic fragments and methods for their use in the treatment of autoimmune disease. Also provided are assays for detecting an autoimmune condition in an animal, including the presence of an autoimmune disease.

The present invention makes use of the discovery that a class of previously unrecognized autoantigenic fragments is generated during the form of apoptosis triggered by the action of the contents of lymphocyte granules on cells. In particular, enzymes found in lymphocyte granules are discovered to cleave proteinaceous cellular autoantigens to yield previously unrecognized autoantigenic fragments. Granzyme B is found to be an important granule enzyme in this generation of autoantigenic fragments. This enzyme was previously known to cleave some of the pro-caspase enzymes to yield active caspases. Granzyme B is now found to directly cleave certain of the substrates of the caspases at different sites to produce novel autoantigenic fragments.

The present invention provides a method of producing granzyme generated autoantigenic fragments in vitro in several ways. In a preferred embodiment, purified granzyme B can be contacted with purified substrates to produce the autoantigenic fragments. Partly or wholly purified enzyme can also be used on partially or wholly purified substrates or cellular lysates containing the substrates. In this case, the autoantigenic fragments can be purified after cleavage of the substrates. Additionally, the contents of granules can be used to produce autoantigenic fragments of cellular components, including the autoantigenic fragments of caspase substrates created by the action of granzyme B, by application of granule contents, or purified substrates or tissue samples isolated from a patient. In some embodiments, the cells of the tissue can be disrupted by lysis or mechanical breakage to release the contents of the cells before contacting the cells with the contents of the granules.

The autoantigenic fragments provided herein can be used in a treatment to tolerize a patient to the presence of the autoantigenic fragments. Once tolerized, the patient would not develop an autoimmune disease associated with the later appearance of the fragments in the patient. Tolerizing strategies involve purification of relevant autoantigenic fragments in a non-aggregated form. Low doses of the fragments are injected in pharmaceutically acceptable carriers, preferably without an adjuvant to induce low-zone tolerance.

The present invention also provides a method of generating an autoimmune response against certain cells in a patient. For example, if it is desirable to generate an autoimmune response against malignant cells in a patient, one can isolate a sample of the cells from the patient and contact the cells with the contents of granules isolated from granule containing lymphocytes. The action of the granule contents on the cells can produce autoantigenic fragments therefrom. In some embodiments, the malignant cells can be disrupted by lysis or mechanical breakage to release the contents of the cells before contacting the cells with the contents of the granules. In any case, the resulting mixture or purified components therefrom can be administered to the patient. Because the autoantigenic fragments produced in this way are the same as those produced in vivo by the action of granule containing lymphocytes, including e.g., CTLs, NK and LAK cells, on the malignant cells, the immune system is thereby stimulated to generate a response against the malignant cells. Therefore, the present invention provides a method to heighten or stimulate the natural immune system processes to act against particular types of cells such as malignant cells.

The autoantigenic fragments useful in the invention described herein display cryptic epitopes. These epitopes are revealed to the immune system after cleavage of the precursor protein by the enzymes contained in granules to yield the autoantigenic fragments. There is a persuasive body of literature that reports that the highly specific humoral immune response to autoantigens in autoimmune disease is T cell-dependent, and that flares in autoimmune disease result when this primed immune system is rechallenged with a self-antigen (reviewed in Burlingame, R. W., et al., 1993; Diamond, B., et al., 1992; Radic, M. Z. and M. Weigert. 1994). However, the mechanisms responsible for initiation of the primary immune response to these molecules, and for subsequently stimulating the secondary response to targeted antigens, have not been completely elucidated (Bach, J. F. and S. Koutouzov. 1997; Sercarz, E. E. and S. K. Datta. 1994). Several studies report that a potential for T cell autoreactivity resides in the immunological non-equivalency of different areas of self-molecules, since tolerance is only induced to dominant determinants which are generated and presented at suprathreshold concentrations during natural processing of whole protein antigens (reviewed in (Sercarz, E. E., et al., 1993; Lanzavecchia, A. 1995). Those determinants which are not generated at all, or are generated at subthreshold levels during antigen processing (termed cryptic), do not tolerize T cells. Thus, potentially autoreactive T cells recognizing this cryptic self epitope are allowed to persist.

The mechanisms through which autoimmunity can arise when normally cryptic determinants become visible to the immune system has received increased attention. Several experimental systems have now provided evidence that the balance of dominant versus cryptic epitopes in a self molecule can be profoundly influenced by forces which alter the 'immunological' structure of molecules (Lanzavecchia, A. 1995). Examples include the revelation of cryptic epitopes through novel cleavage (Bockenstedt, L. K., et al., 1995; Mamula, M. J. 1993), or through altered conformation induced by high affinity ligand binding (e.g. to an antibody or receptor molecule (Salemi, S., et al., 1995; Simitsek, P. D., et al., 1995; Watts, C. and A. Lanzavecchia. 1993). The unique, high-titer autoantibody responses that characterize different autoimmune diseases can therefore be viewed as the immunologic impression of the initiating events that revealed suprathreshold concentrations of non-tolerized structure in a pro-immune context, thus satisfying the stringent criteria for initiation of a primary immune response (Casciola-Rosen, L. and A. Rosen. 1997).

The alteration of the structure of autoantigens during apoptosis is an important feature which underlies targeting of specific molecules by the immune system. Understanding whether and how the structure of those autoantigens are cleaved during apoptosis, provides insights into the role of apoptosis in initiation of the autoimmune response. One such mechanism involves the action of the enzymes in contents of granules found in granule containing lymphocytes and is described herein. The contents of these granules are shown to act to reveal cryptic epitopes by cleaving autoantigens to autoantigenic fragments. In a preferred method, granzyme B cleaves autoantigenic proteins to create preferred autoantigenic fragments that display cryptic epitopes to the immune system.

Recent reports using caspase inhibitors have emphasized the contribution of caspase-independent pathway(s) when target cell death is induced by cytotoxic lymphocyte granule exocytosis (Sarin et al., 1997; Talanian et al., 1997). The results presented here demonstrate that several of the downstream substrates cleaved by the caspase family of proteases during apoptosis are also directly and efficiently cleaved by granzyme B both in vitro and in target cells undergoing lymphocyte granule-induced cytotoxicity. This confirms the existence of efficient caspase-independent proteolytic pathways during this form of cell death.

Not all downstream substrates of caspase-3 are cleaved by granzyme B with similar efficiency. In the case of PARP and U1-70 kDa, cleavage efficiency by caspase-3 exceeds that by granzyme B by more than 200 fold, while NuMA and DNA-PK$_{cs}$ are cleaved with similar efficiencies by granzyme B and caspase-3 (Table I). The relative cleavage efficiency of a given substrate by the two proteases appears to account for the results observed when caspase-3 activity is inhibited in intact cells. Thus, while PARP cleavage during granule-mediated cytotoxicity is inhibited by Ac-DEVD-CHO, cleavage of DNA-PK$_{cs}$ and NuMA are only minimally affected. It is therefore believed that caspase-independent components of granule-mediated death are generated through altering the function of those downstream substrates that are efficiently cleaved by granzyme B (and potentially other granule proteases).

The results presented herein are consistent with recent studies in which granzyme B-induced proteolysis of PARP and U1-70 kDa (both inefficient direct substrates for granzyme B) in an intact cell model was well inhibited by caspase inhibitors (Talanian et al., 1997). The results differ from a previous study which failed to demonstrate unique DNA-PK$_{cs}$ fragments during CTL-induced target cell death, or by granzyme B in vitro (Song et al., 1996a). Different antibodies to DNA-PK$_{cs}$ used in the two studies may account for the failure of the previous study to find that a unique 100 kDa C-terminal fragment is generated by granzyme B.

Figure 3:
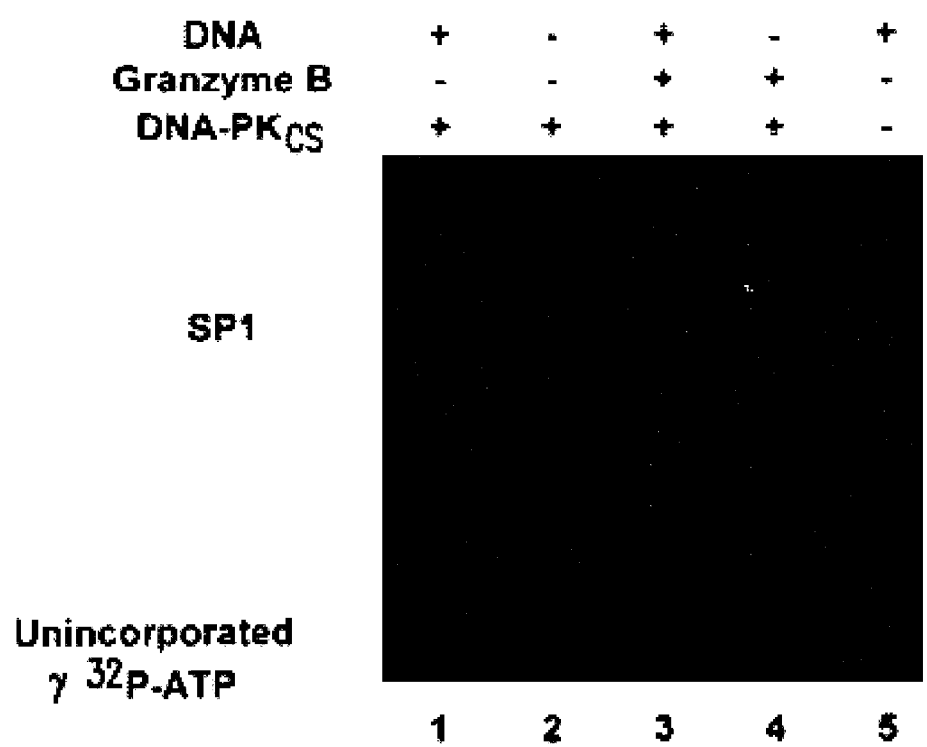
FIG. 3. Kinase activity of DNA-PK$_{cs}$ is abolished after cleavage with granzyme B. Kinase assays were performed using intact DNA-PK$_{cs}$ (lanes 1 & 2) or granzyme B-cleaved DNA-PK$_{cs}$ (lanes 3 & 4) in the absence (lanes 2 & 4) or presence (lanes 1 & 3) of 10 µg/ml of DNA. DNA-PK$_{cs}$ itself was omitted from the otherwise complete kinase reaction mix as a control in lane 5. Phosphorylation of SP1 substrate was detected by autoradiography.

The results indicate that direct and efficient cleavage of NuMA and DNA-PK$_{cs}$ by granzyme B achieves functional effects similar to those caused by caspase cleavage during other forms of apoptosis. This is supported by the demonstration that the cleavage of DNA-PK$_{cs}$ by granzyme B completely abrogates its kinase activity (FIG. 3). This granzyme B-mediated cleavage of DNA-PK$_{cs}$ differs from caspase-3-mediated cleavage of this substrate in several ways: (i) The presence of DNA ends renders the granzyme B-mediated cleavage significantly less efficient, while DNA ends are required for efficient cleavage of DNA-PK$_{cs}$ by caspase-3 (Casciola-Rosen et al., 1996; Song et al., 1996b) (ii) While caspase-3 cleavage of DNA-PK$_{cs}$ decreases its kinase activity to approximately 60% of control levels (Casciola-Rosen et al., 1996), cleavage by granzyme B completely abrogates kinase activity. These data indicate that granzyme B cleaves and fully inactivates DNA-PK$_{cs}$ very early during granule-mediated cytotoxicity, before significant internucleosomal DNA cleavage has occurred, and thus before caspase-3 can efficiently cleave DNA-PK$_{cs}$. Once abundant DNA ends have been generated, cleavage by caspase-3 should predominate (with the resulting fragments possessing residual kinase activity).

Although the functional consequences of substrate cleavage by caspases during apoptosis in vivo is not known for most substrates, recent reports demonstrate that cleavage can activate critical pro-apoptotic activities (e.g. activation of DNA fragmentation factor by caspase-3 (Liu et al., 1997)). In other cases, reports suggest that substrate cleavage might disable important structural and homeostatic functions (Casciola-Rosen et al., 1996; Ghayur et al., 1996). It is therefore reported that the ability of cytolytic lymphocyte granule proteases to directly cleave some caspase substrates underlies the caspase-independent component of the death pathway induced by these cells (Sarin et al., 1997). The ability of the lymphocyte granule-induced cytotoxicity pathway to generate a novel form of nuclear condensation even in the absence of caspase activity, is consistent with this theory.

Studies on macromolecular and tetrapeptide substrates provide insights into the substrate specificity of granzyme B. For example, the direct cleavage of PARP by granzyme B occurs at VGPD$^{537}$-S$^{538}$ SEQ ID NO:35 (Froelich et al., 1996a), while processing of several caspase precursors occurs at IETD sites (Fernandes-Alnemri et al., 1996; Ramage et al., 1995; Srinivasula et al., 1996; Yamin et al., 1996). The studies presented here demonstrate that granzyme B cleaves a macromolecular substrate (DNA-PK$_{cs}$) at VGPD-F$^{2699}$ SEQ ID NO:34, a site consistent with the tetrapeptide substrate specificity of granzyme B defined using a combinatorial tetrapeptide library (Thornberry et al., 1997). Interestingly, granzyme B also directly cleaves this substrate at a nearby DEVD-N$^{2713}$ SEQ ID NO:34, suggesting that the determinants of macromolecular substrate specificity are more complex than those contained in the tetrapeptides tested.

Using the fragment sizes of NuMA and DNA-PK$_{cs}$ generated by granzyme B, the known epitope specificity of several of the antibodies used, and the known substrate specificity of granzyme B, these studies indicate that the most likely granzyme B cleavage site generating the 100 kDa C-terminal fragment of DNA-PK$_{cs}$ is VDQD$^{3210}$-G$^{3211}$ SEQ ID NO:34. Similarly, the most likely granzyme B cleavage site in NuMA occurs at VLGD$^{411}$-V$^{492}$ SEQ ID NO:32. Several studies have addressed the cell biology of granzyme B during perforin/granzyme B-induced apoptosis (Froelich et al., 1996b; Shi et al., 1997; Trapani et al., 1996). These studies reported that granzyme B autonomously enters the cytoplasm of target cells. That event alone does not induce target cell apoptosis. In the presence of perforin, however, apoptosis is induced in target cells. That event is accompanied by the rapid enrichment of granzyme B in nuclei and nucleoli of target cells (Jans et al., 1996; Pinkoski et al., 1996; Trapani et al., 1996). It is therefore of importance that the granzyme B substrates described here are nuclear proteins. These substrates function in both structural and homeostatic pathways which are impacted by the caspases during apoptosis. The observation that a component of granule-induced cell death is caspase-independent, taken together with the ability of caspases and granzyme B to efficiently cleave a common subset of downstream substrates at different sites during granule-induced cytotoxicity, highlights the importance of proteolysis of those common substrates in generating the apoptotic phenotype. Table II).

In the light of several descriptions of viral or endogenous caspase inhibitors (Beidler et al., 1995; Bump et al., 1995; Irmler et al., 1997; Thome et al., 1997; Xue and Horvitz, 1995), as well as long-lived cells or tumor cells which express low levels of specific caspase family members (Krajewska et al., 1997; Krajewski et al., 1997), the caspase-independent activity of granzyme B provides the host with apoptotic effector mechanisms that are insensitive to inhibitors of the signaling or execution components of the apoptotic cascade.

Many of the downstream caspase substrates described to date are autoantigens targeted in human systemic autoimmune diseases (Casciola-Rosen et al., 1995; Casciola-Rosen et al., 1994; Casciola-Rosen et al., 1996; Casiano et al., 1996; Greidinger et al., 1996). The present demonstration that several of these substrates are also directly cleaved by granzyme B, generating unique fragments not generated during any other form of apoptosis studied to date, demonstrates how non-tolerized determinants of autoantigens can be revealed during certain forms of CTL-mediated apoptotic death.

In the experimental results presented herein, it is demonstrated that DNA-PK$_{cs}$ and NuMA are directly cleaved by granzyme B, both in vitro and in cells undergoing granule-induced cytotoxicity. Although the efficiency of cleavage of these substrates is similar to those observed for caspase 3-mediated cleavage, the fragments generated by the 2 proteases are distinct. Since caspases appear to initiate apoptosis by altering the function of downstream substrates (either by decreasing the function of the intact substrate, or by generating fragment(s) with pro-apoptotic activity), it is believed that direct cleavage of caspase substrates by granzyme B during cytotoxic lymphocyte granule-induced apoptosis plays an important role in caspase-independent target cell death. The ability of the contents of cytotoxic lymphocyte granules to bypass the requirement for caspases in the death pathway may guarantee the demise of target cells whose caspase pathway is incomplete or under strict endogenous or exogenous regulatory control.

The action of granzyme B in producing particular autoantigenic fragments from particular autoantigens is exemplified herein. However, the general understanding of the role of granule proteases as described and exemplified in the granzyme B model system allows one to generate these and other autoantigenic fragments. The autoantigenic fragments produced can be used in the preparation of pharmaceutical compositions, for treating patients at risk for or suffering from autoimmune diseases and cancer, and in assays for assessing the presence or absence of an autoimmune condition in a patient.

The following examples are presented by the way of illustration and, because various other embodiments will be apparent to those in the art, the following examples are not to be construed as a limitation on the scope of the invention.

EXAMPLE 1

General Materials and Methods

Materials.

Purified DNA-dependent protein kinase (DNA-PK) and SP1 were purchased from Promega (Madison, Wis.). ATP was purchased from Fluka (Ronkonkoma, N.Y.), and $^{32}$P-ATP was from Du Pont/NEN (Wilmington, Del.). Ac-DEVD-CHO and Ac-YVAD-CHO were manufactured by Merck (Rahway, N.J.). Caspase-3 was purified as described (Nicholson et al., 1995). Patient sera were used to immunoblot the nuclear mitotic apparatus protein (NuMA), poly(ADP-ribose) polymerase (PARP) and DNA-PK$_{cs}$ (Casciola-Rosen et al., 1995; Greidinger et al., 1996). Monoclonal antibodies can be made by methods known in the art. Two different monoclonal antibodies, designated 18-2 and 25-4 (kind gifts from Dr. Tim Carter, St. Johns University, Jamaica, N.Y.) were also used to detect DNA-PK$_{cs}$ by immunoblotting (see Table II for a summary of the antibodies used to detect DNA-PK$_{cs}$ and its cleaved fragments). Rabbit polyclonal antibodies to caspases were raised against the large subunits of caspase-3 and caspase-7, using methods commonly known in the art. Immunoblotted proteins were detected using the SUPERSIGNAL™ substrate system (Pierce, Rockford, Ill.), according to the manufacturer's instructions.

In vitro cleavage of purified DNA-PK$_{cs}$ and [$^{35}$S] methionine-labeled caspase-3 precursor, caspase-7 precursor, PARP, and NuMA.

cDNAs for caspase-3, caspase-7, NuMA and PARP were used to drive the synthesis of [$^{35}$S]methionine-labeled proteins by coupled transcription/translation in rabbit reticulocyte lysates. For all purified substrates, cleavage reactions were performed in buffer consisting of 50 mM Hepes pH 7.4, 10% sucrose and 5 mM DTT in the presence of the granzyme B concentrations indicated in FIG. 1. After incubation at 37° C. for 15 min, reactions were terminated and samples were electrophoresed on 10% (DNA-PK$_{cs}$, NuMA), 12% (PARP) or 15% (caspases 3 and 7) SDS-polyacrylamide gels. Radiolabeled proteins and their fragments were visualized by fluorography. Intact and cleaved DNA-PK$_{cs}$ were visualized by immunoblotting with monoclonal antibody 18-2 (Casciola-Rosen et al., 1995).

Calculation of catalytic constant values.

Catalytic constant ($k_{cat}/k_m$) values were calculated essentially as described (Casciola-Rosen et al., 1996). Briefly, subsaturating substrate concentrations were used in each in vitro reaction, and product appearance was assumed to be a first order process. Substrate and product bands on autoradiograms were scanned by densitometry. Several appropriate densitometry systems are available, e.g. PDI Discovery System, with Quantity One Software, Protein Databases, Inc., (Huntington Station, N.Y.). kcat/Km values were calculated by fitting the dose-response data to the first order rate equation: percent substrate cleavage=100*$((1-e^{-((kcat*[E]/Km)*time)})$.

In vitro cleavage of endogenous DNA-PK$_{cs}$, NuMA, and PARP in HeLa lysates.

Control HeLa lysates were prepared using methods commonly applied in the art, as described in Casciola-Rosen et al., 1994. 12.5 nM purified granzyme B or 105 pM purified caspase-3 were then added to the lysates, in the absence or presence of 100 nM Ac-DEVD-CHO or Ac-YVAD-CHO. The mixtures were incubated for 15 mn on ice to facilitate binding of the inhibitors to proteases prior to performing cleavage reactions at 37° C. for 60 min. After electrophoresing the samples on 10% SDS-polyacrylamide gels containing 0.087% bisacrylamide, the intact proteins and their cleaved fragments were visualized by immunoblotting.

Determination of granzyme B cleavage sites in DNA-PK$_{cs}$ by P1 Asp mutagenesis.

A partial cDNA clone for DNA-PK$_{cs}$, encoding Met$^{2566}$ through Leu$^{2928}$ (the region containing the caspase-3 cleavage site as well as the putative granzyme B site), was amplified by reverse-transcriptase PCR from HeLa cell poly(A)+ RNA using primers containing 5' EcoRI and 3' XbaI restriction enzyme-adapters. After ligation into the corresponding restriction sites of pBluescript II SK+ (Stratagene), this clone was used as template for mutagenesis by overlap-extension PCR to generate clones containing D$^{2698}$A (P1 of the putative granzyme B site) and D$^{2712}$A (P1 of the known caspase-3 site) modifications. [35S]-Radiolabeled polypeptides were generated by coupled in vitro transcription/translation, and then incubated with either recombinant caspase-3 (8 nM) or purified YT cell-derived granzyme B (8 nM) for 60 min at 37° C. in a buffer composed of 50 mM Hepes/KOH (pH 7.0), 10% (w/v) sucrose, 2 mM EDTA, 0.1% (w/v) CHAPS, 5 mM dithiothreitol. The resulting cleavage products were resolved on SDS-polyacrylamide gels (10–20% gradient gels) and visualized by fluorography.

In vivo cleavage of endogenous DNA-PK$_{cs}$, NuMA and PARP during YT cell granule content-induced cytotoxicity of intact K562 cells.

Intact cytoplasmic granules were purified from YT cells, and the granule contents were isolated using known methods (Tschopp, 1994). Some of these preparations were used for the further purification of granzyme B (Tschopp, 1994). Purity of the protease was confirmed by silver staining of overloaded SDS-polyacrylamide gels. The cytotoxic effects of YT granule contents were determined as follows: Jurkat T cells or K562 cells were radiolabeled with 100 μCi/ml [$^{51}$Cr] sodium chromate, washed, resuspended in Ca$^{2+}$-free HBSS, and then incubated with granule contents (0–5 μl) and 1 mM CaCl$_2$ for increasing times. The percentage specific [$^{51}$Cr] was calculated using the following formula: % specific lysis=[(sample cpm−spontaneous cpm)/ (maximum cpm−spontaneous cpm)]×100. In vivo experiments to assay the effect of YT cell granule contents on DNA-PK$_{cs}$, NuMA and PARP in intact K562 cells were performed as follows: K562 cells were washed twice with PD (2.7 mM KCl, 1.5 mM KH$_2$PO$_4$, 137 mM NaCl, 8 mM Na$_2$HPO$_4$), then resuspended at 1.7×10$^7$ cells/ml in PD in the absence or presence of 100 μM Ac-DEVD-CHO, and incubated at 37° C. for 30 min. Aliquots containing 3.4×10$^5$ cells were incubated for a further 90 min at 37° C. with 1 mM EDTA or 1 mM Ca$^{2+}$ and 2 μl of YT granule contents (which induces 20–40% specific chromium release in 60 min, and characteristic internucleosomal DNA degradation. The total reaction volume of each sample was 30 μl. The reactions were terminated by boiling in SDS gel buffer and samples were electrophoresed and immunoblotted as described above. Experiments were performed using 2 different preparations of granule contents and 4 different cell types (K562, Jurkat, HeLa, primary human myoblasts).

Confocal Immunofluorescence microscopy.

Morphologic experiments were performed on HeLa cells grown on No. 1 glass coverslips. Coverslips were washed three times with ice-cold HBSS without Ca$^{2+}$, prior to incubation (4° C., 30 min) with 25 μl of HBSS minus Ca$^{2+}$ containing 0.8 μl of YT cell granule contents (see above), in the presence or absence of 200 μM Ac-DEVD-CHO. 25 μl of HBSS containing 2 mM CaCl$_2$ was then added to each coverslip (mixed well by repeated, gentle aspiration), followed by incubation in a humidified chamber at 37° C. for 60 min. The cells were then fixed in 4% paraformaldehyde (4° C., 5 min), permeabilized with acetone (4° C., 15 sec), and stained sequentially with antibodies to PARP or NuMA, propidium iodide and DAPI as described (Casciola-Rosen et al., 1994a). Coverslips were mounted on glass slides with Permafluor (Lipshaw, Pittsburgh, Pa.), and confocal microscopy was performed on a scanning confocal microscopy system (LSM 410, Carl Zeiss, Inc., Thornwood, N.J.).

LAK cell-mediated cytotoxicity.

LAK cells were obtained by culturing human PBMCs for 4 days in LAK medium (RPMI supplemented with 10 mM Hepes pH 7.4, L-glutamine, 2% autologous plasma), and 1000 Cetus units/ml of hrIL-2 (Chiron Therapeutics, Emeryville, Calif.) (Topalian et al., 1989). Fas-negative target cells (K562 erythroleukemia cells) were resuspended at $1.3 \times 10^6$ cells/ml in LAK medium in the presence or absence of 100 μM Ac-DEVD-CHO, and incubated at 37° C. for 60 min, prior to co-incubation with LAK effector cells (effector:target ratio of 5:1) for 4 h. After 2 washes with PD, cells were lysed and boiled in SDS sample buffer, and PARP, DNA-PK$_{cs}$ and NuMA were assayed by immunoblotting as described above.

Kinase assay.

Kinase assays were performed on intact DNA-PK$_{cs}$ or DNA-PK$_{cs}$ that had first been cleaved by granzyme B as follows. Reaction mixtures containing 10 mM Hepes pH 7.4, 2 mM MgCl$_2$, 10 mM KCl, 2.7 mM DTT, and 50 ng DNA-PK$_{cs}$ in the absence or presence of 12.5 nM purified granzyme B, were incubated for 13.5 min at 37° C. Kinase reactions were subsequently initiated by adding 100 ng SP1 and 150 μM ATP containing 1.5 μCi [$^{32}$P]-ATP (3000 Ci/mmol), in the absence or presence of 10 μg/ml sheared herring sperm DNA (Promega). Samples were incubated at 37° C. for 10 min (well within the linear range of the assay, data not shown), before terminating the reactions by adding SDS gel buffer and boiling. After electrophoresing the samples on 8% SDS-PAGE, SP1 phosphorylation was detected by autoradiography, and quantitated by densitometry. Cleaved status of the kinase was confirmed in parallel by immunoblotting.

EXAMPLE 2

DNA-PK$_{cs}$ and NuMA are Very Efficient Substrates for Purified Granzyme B

Granzyme B has previously been reported to cleave the precursors of several caspases (including caspases 3, 7 and 10), resulting in activation of their proteolytic activity. The catalytic efficiency of cleavage of these substrates by granzyme B serves as a useful standard against which granzyme B-mediated cleavages of other substrates can be compared. Purified [$^{35}$S]methionine-labeled precursors of caspase-3 and caspase-7, or THP.1 cytosols (containing these precursor proteases) were incubated in vitro with increasing concentrations of purified granzyme B. The dose-response data obtained (FIG. 1) was used to calculate catalytic constant ($k_{cat}/K_m$) values of $1.8 \pm 0.6 \times 10^5$ M$^{-1}$s$^{-1}$ (radiolabeled substrate) and $1.9 \pm 0.1 \times 10^5$ M$^{-1}$s$^{-1}$ (immunoblotting) for caspase-7, and $3.6 \pm 1.0 \times 10^4$ M$^{-1}$s$^{-1}$ (radiolabeled substrate) and $2.3 \pm 0.4 \times 10^4$ M$^{-1}$s$^{-1}$ (immunoblotting) for caspase-3 (Table I). Thus, granzyme B cleaves caspase-7 approximately 6 fold more efficiently than caspase-3, consistent with previous reports (Talanian et al., 1997).

It was then determined whether any of the downstream substrates known to be cleaved by caspases during apoptosis were also directly cleaved by granzyme B, and the efficiency of cleavage of each substrate by the two proteases was compared. Purified DNA-PK$_{cs}$ was very efficiently cleaved by granzyme B in the absence of added DNA ($k_{cat}/K_m = 2.5 \pm 0.8 \times 10^6$ M$^{-1}$s$^{-1}$, see FIG. 1 and Table I), making it the best substrate for granzyme B described to date, with a cleavage efficiency two orders of magnitude better than that described for granzyme B-mediated cleavage of the caspase-3 precursor. When similar experiments were performed in the presence of 10 μg/ml DNA, DNA-PK$_{cs}$ cleavage was decreased by approximately 90%.

Caspase-3-mediated cleavage of DNA-PK$_{cs}$ was also extremely efficient ($k_{cat}/K_m$ value = $7.5 \pm 0.8 \times 10^6$ M$^{-1}$s$^{-1}$). In this case, efficient cleavage was only obtained in the presence of DNA ((Casciola-Rosen et al., 1995), and Table I). NuMA, a nuclear matrix protein that is cleaved in apoptotic cells by an unidentified protease with features of the caspase family, was also very efficiently cleaved by granzyme B ($k_{cat}/K_m$ value = $5.4 \pm 1.4 \times 10^5$ M$^{-1}$s$^{-1}$, see Table I). The efficiency of this cleavage was one order of magnitude greater than that observed for granzyme B-mediated processing of the caspase-3 precursor. NuMA was also efficiently cleaved by purified caspase-3, with a $k_{cat}/K_m$ value of $= 5.0 \pm 1.0 \times 10^5$ M$^{-1}$s$^{-1}$. (Table I). In contrast to DNA-PK$_{cs}$ and NuMA (where granzyme B- and caspase-3-mediated cleavages are similarly efficient), PARP was a relatively poor substrate for granzyme B, with a $k_{cat}/K_m$ value ($2.3 \pm 1.8 \times 10^4$ M$^{-1}$s$^{-1}$) that is approximately 200 fold lower than that for caspase-3 (see Table I). Granzyme B was also a poor catalyst for cleaving U1-70 kDa, with $k_{cat}/K_m$ values $< 10^3$ M$^{-1}$s$^{-1}$. The efficiency of substrate cleavage by granzyme B is therefore similar to caspase-3 for some substrates (e.g. DNA-PK$_{cs}$ and NuMA), while it is more than 2 orders of magnitude less efficient for others (e.g. PARP and U1-70 kDa).

EXAMPLE 3

Different Substrate Fragments Are Detected After Cleaving Autoantigens in vitro with Granzyme B or Caspase-3

To directly compare the fragments generated by granzyme B and caspase-3, purified DNA-PK$_{cs}$, in vitro translated [$^{35}$S]methionine-labeled PARP, and endogenous substrates (NuMA and DNA-PK$_{cs}$ in HeLa cell lysates) were incubated with protease and electrophoresed in adjacent lanes. When granzyme B was used to cleave DNA-PK$_{cs}$, fragments of 100 kDa and 250 kDa were generated, (detected by immunoblotting using antibodies recognizing the C-terminus or N-terminus of DNA-PKcs, respectively) (FIG. 2, lanes 2 & 5; and Table II). In contrast, caspase-3 cleavage yielded a 150 kDa C-terminal fragment (FIG. 2, lane 3) and a 250 kDa N-terminal fragment (FIG. 2, lane 6).

Granzyme B-mediated cleavage of NuMA generated a novel fragment migrating at 175 kDa on SDS-PAGE, which was distinct from the 185 kDa fragment detected after cleavage with caspase-3 (FIG. 2, lanes 7–9). Similarly, novel fragments of PARP migrating at 72, 62 and 42 kDa were detected after incubation with granzyme B; these differed from the 89 and 24 kDa fragments generated by caspase-3-mediated cleavage of PARP (FIG. 2, lanes 10–12 and Table II). Granzyme B therefore directly cleaves several of the downstream substrates of caspase-3 in vitro. In all cases, the fragments generated by granzyme B differ from those generated by caspase-3.

EXAMPLE 4

Kinase Activity of DNA-PK$_{cs}$ is Abolished by Granzyme B Cleavage

To determine the effect of granzyme B-mediated cleavage on the kinase activity of DNA-PK$_{cs}$, the ability of intact and cleaved DNA-PK$_{cs}$ to phosphorylate the SP1 transcription factor was quantitated. The kinase activity of DNA-PK$_{cs}$ was entirely DNA-dependent (FIG. 3, lanes 1 and 2). When DNA-PK$_{cs}$ was pretreated with 12.5 nM granzyme B for 13.5 min at 37° C. (which cleaves DNA-PK$_{cs}$ (FIG. 1)), followed by the addition of DNA, [$^{32}$P]ATP and SP1 (which initiate the phosphorylation reaction), kinase activity was entirely abolished (FIG. 3, lane 3). Whether any of the fragments generated by granzyme B-mediated cleavage of DNA-PK$_{cs}$ have novel activity(ies) in addition to the autoantigenic reactions demonstrated herein remains to be determined.

EXAMPLE 5
Granzyme B Induces Novel Fragments of DNA-PK$_{cs}$ and NuMA in Cell Lysates Previous studies reported that the cleavage of PARP that occurs in lysates of COS cells expressing granzyme B can be almost completely inhibited by the caspase inhibitor, Ac-DEVD-CHO (Darmon et al., 1995). Because this compound is not an inhibitor of granzyme B, this observation suggests that this cleavage is mediated solely by caspases which have been activated by granzyme B in these extracts. The observation that PARP itself is cleaved by granzyme B approximately 200 fold less efficiently than by caspase-3 further supports this conclusion (see Table I). Since NuMA and DNA-PK$_{cs}$ are cleaved with similar efficiencies by caspase-3 and granzyme B, it was of interest to determine whether these substrates are cleaved directly by granzyme B in cell lysates that contain caspase precursors. Therefore, an in vitro assay system was established in which cleavage of endogenous DNA-PK$_{cs}$, NuMA or PARP was monitored after addition of purified caspase-3 or granzyme B. The assay was conducted in the presence or absence of the caspase inhibitor, Ac-DEVD-CHO.

Figure 4:
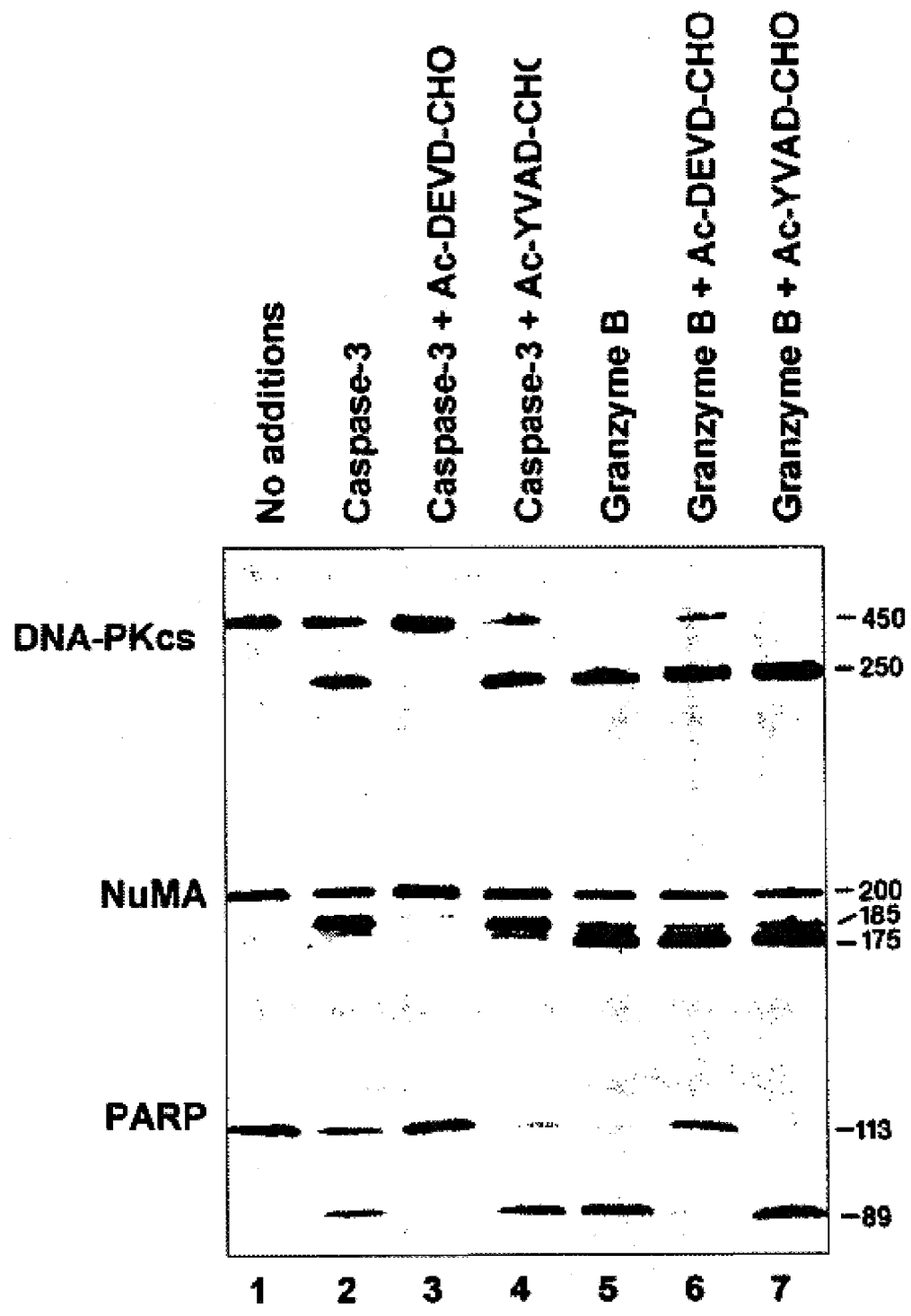
FIG. 4. Endogenous DNA-PK$_{cs}$ and NuMA in HeLa cell lysates are cleaved in a caspase-independent manner after adding purified granzyme B and incubating in vitro. 12.5 nM purified granzyme B (lanes 5–7) or 105 pM purified caspase-3 (lanes 2–4) were added to lysates of control HeLa cells, in the presence of 100 nM Ac-DEVD-CHO (lanes 3 & 6) or 100 nM Ac-YVAD-CHO (lanes 4 & 7). After incubating at 37° C. for 60 min, the reactions were terminated. DNA-PK$_{cs}$, NuMA and PARP were detected by immunoblotting as described in Example 1 (monoclonal antibody 18-2 was used to detect DNA-PK$_{cs}$). Equal amounts of protein were electrophoresed in each lane.

Incubation of control extracts at 37° C. for 60 minutes resulted in no significant cleavage of DNA-PK$_{cs}$ or PARP, but was associated with minimal cleavage of NuMA, leading to the production of minor fragments of 185 and 187 kDa (FIG. 4, lane 1). When purified caspase-3 was added to control extracts, caspase-3-specific fragments of PARP (89 kDa), NuMA (185 kDa) and DNA-PK$_{cs}$ (250 kDa N-terminal fragment, 150 kDa C-terminal fragment) were generated (FIG. 4, lane 2). As demonstrated above, substrate fragments generated by the activity of caspase-3 are entirely abolished by 100 nM Ac-DEVD-CHO (K$_i$ caspase-1=17 nM; K$_i$ caspase-3=0.2 nM; K$_i$ caspase-6=31 nM; K$_i$ caspase-7=1 nM; K$_i$ caspase-8=0.92 nM; K$_i$ caspase-9=60 nM; K$_i$ caspase-10=12 nM) (FIG. 4, lane 3), but were unaffected by 100 nM Ac-YVAD-CHO (K$_i$ caspase-1=0.6 nM; K$_i$ caspase-3 and caspase-7>10 µM; K$_i$ caspase-10=408 nM) (FIG. 4, lane 4).

In the presence of 12.5 nM granzyme B, all three substrates were efficiently cleaved (FIG. 4, lane 5). The predominant PARP fragment induced by granzyme B co-migrated with the fragment induced by caspase-3 (FIG. 4, lane 5). There was also a minor (<5%) fragment of 62 kDa which corresponded with the fragment induced by granzyme B on purified substrate. In contrast, only a minor proportion of the NuMA fragments induced by granzyme B co-migrated with the fragment generated by caspase-3 (185 kDa). The major, novel fragment of 175 kDa (FIG. 4, lane 5) corresponded with the fragment induced by granzyme B on purified in vitro-translated substrate. Granzyme B-mediated cleavage of DNA-PK$_{cs}$ generated a 260 kDa N-terminal fragment co-migrating with that generated by caspase-3 (FIG. 4, lanes 2 & 5), as well as a unique 100 kDa C-terminal fragment which corresponded with that induced by granzyme B on purified substrate (FIG.2, lane 2).

When Ac-DEVD-CHO or 2 mM iodoacetamide were added to the extracts 15 minutes prior to the addition of granzyme B, cleavage of PARP was almost entirely abolished (FIG. 4, lane 6). In contrast, the cleavage of NuMA and DNA-PK$_{cs}$ was only partially inhibited (FIG. 4, lane 6) (20–40% inhibition in 5 separate experiments). Generation of caspase-3-specific fragments of both NuMA (185 kDa) and DNA-PKcs (150 kDa C-terminal fragment was abolished under these circumstances, while formation of the 250 kDa N-terminal fragment of DNA-PK$_{cs}$ was inhibited by 20–40% (FIG. 4, lane 6).

Generation of granzyme B-specific fragments (175 kDa NuMA fragment and 100 kDa C-terminal DNA-PK$_{cs}$ fragment) was not affected by the inhibitors of caspase (FIG. 4, lane 6). The failure of Ac-DEVD-CHO to markedly inhibit generation of the 250 kDa DNA-PK$_{cs}$ fragment indicates that the majority of DNA-PK$_{cs}$ cleavage detected after addition of granzyme B to lysates results from direct cleavage by this protease (rather than indirectly through activation of caspase-3). Taken together, the results demonstrate that granzyme B competes with caspase-3 for cleavage of endogenous substrates in cell lysates. The outcome of this competition can be accurately predicted by comparing $k_{cat}/K_m$ values: for those substrates where $k_{cat}/K_m$ for cleavage by caspase-3 is greater than that of granzyme B (e.g. PARP), caspase-3 fragments are detected almost exclusively. For those substrates where the $k_{cat}/K_m$ values are similar for the proteases, addition of granzyme B results in the formation of novel, granzyme B-specific fragments (e.g. DNA-PK$_{cs}$ and NuMA).

EXAMPLE 6
Granzyme B Cleavage Sites in DNA-PK$_{cs}$

Figure 5:
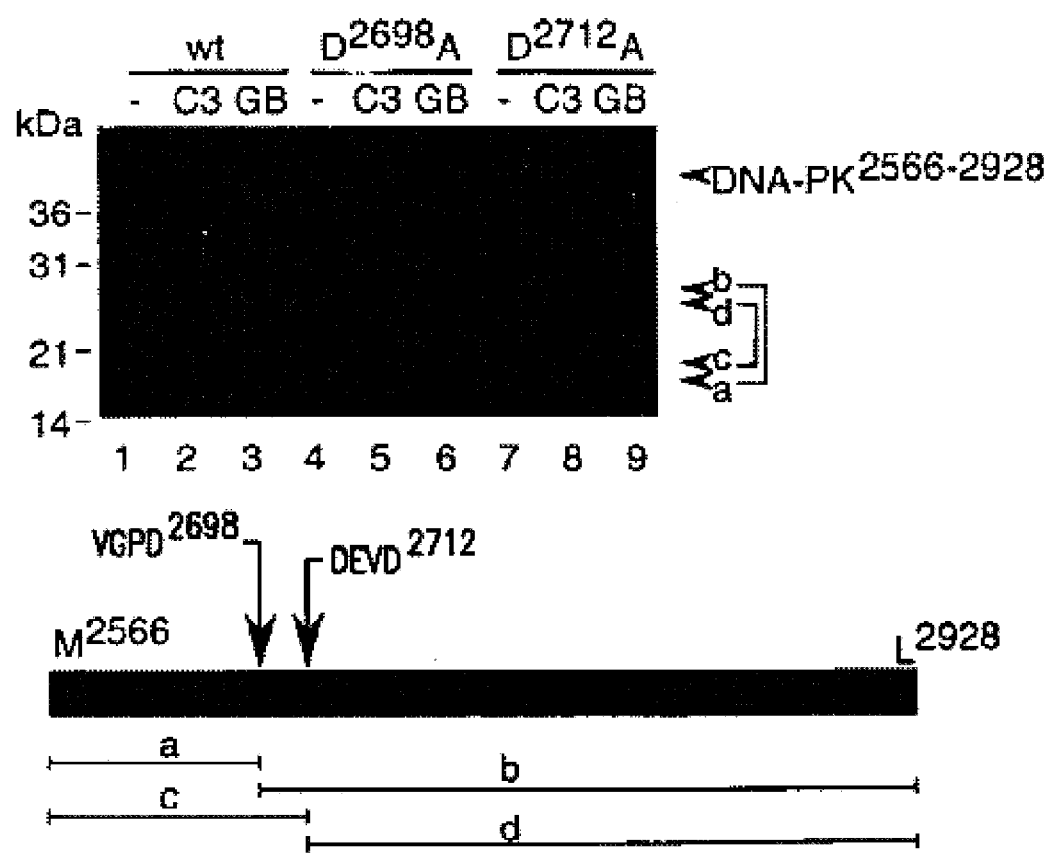
FIG. 5. Granzyme B cleaves DNA-PK$_{cs}$ at VGPD$^{2698}$-F$^{2699}$ SEQ ID NO:24 and DEVD$^{2712}$-N$^{2113}$ SEQ ID NO:1. A [$^{35}$S]methionine-labeled wild-type (wt) DNA-PK$_{cs}$ polypeptide (DNA-PK$_{cs}^{2566-2928}$) and two radiolabeled polypeptides containing mutations in the P$_1$ positions of the predicted granzyme B cleavage site (D$^{2698}$A) and the known caspase-3 cleavage site (D$^{2712}$A), were generated as described in Example 1. These polypeptides were incubated in the absence of added proteases (lanes 1, 4 & 7), or in the presence of 8 nM recombinant caspase-3 (lanes 2, 5 & 8) or 8 nM purified granzyme B (lanes 3, 6 & 9) for 60 min at 37° C. After terminating the reactions, samples were electrophoresed, and the intact polypeptide and the cleavage products were detected by fluorography. Fragment sizes of 18 kDa (a), 28 kDa (b), 20 kDa (c) and 26 kDa (d) were generated (see lower panel for schematic representation).

To address whether the 250 kDa DNA-PK$_{cs}$ fragment generated by caspase-3 and granzyme B result from cleavage at the same and/or different, but closely-spaced sites, not distinguishable by SDS-PAGE, we generated a fragment of DNA-PK$_{cs}$ (Met$^{2566}$-Leu2928 SEQ ID NO:34) encompassing both the known caspase-3 cleavage site at DEVD$^{2712}$-N$^{2713}$ SEQ ID NO:54 (Casciola-Rosen et al., 1996; Song et al., 1996b), as well as the potential granzyme B cleavage site at VGPD$^{2698}$-F$^{2699}$ SEQ ID NO:34. The relevant P$_1$ aspartic acids (D$^{2698}$ and D$^{2712}$) in this fragment were mutated to alanines (D$^{2698}$A; D$^{2712}$A), and susceptibility of wild type and mutated forms to cleavage by caspase-3 or granzyme B was assessed (FIG. 5). Cleavage of the wild type protein by caspase-3 resulted in two fragments of 26 kDa and 20 kDa (FIG. 5, lanes 1,2); this cleavage was entirely abolished by the D$^{2712}$A mutation (FIG. 5, lanes 7,8), confirming that caspase-3 cleaves at DEVD$^{2712}$-N$^{2713}$. In addition to 20 kDa and 26 kDa fragments identical to those generated by caspase-3, granzyme B cleavage also resulted in fragments of 28 kDa and 18 kDa (FIG. 5, lane 3); these unique fragments were enhanced by the D$^{2712}$A mutation (FIG. 5, lane 9), but were abolished by the D$^{2698}$A mutation (FIG. 5, lane 6), placing a granzyme B cleavage site at VGPD$^{2698}$-F$^{2699}$SEQ ID NO:34. These data demonstrate that granzyme B can cleave at VGPD$^{2698}$-F$^{2699}$ SEQ ID NO:39, a site predicted by previous studies using a combinatorial tetrapeptide substrate library (Thornberry et al., 1997). Furthermore, granzyme B also cleaves at the caspase-3 cleavage site, DEVD$^{2712}$-N$^{2713}$ SEQ ID NO:34. The C-terminal granzyme B-unique cleavage site is believed to be VDQD$^{3210}$-G$^{3211}$ SEQ ID NO:34. This cleavage yields the approximately 100 kDa fragment from amino acids 3212 to 4096.

Figure 6:
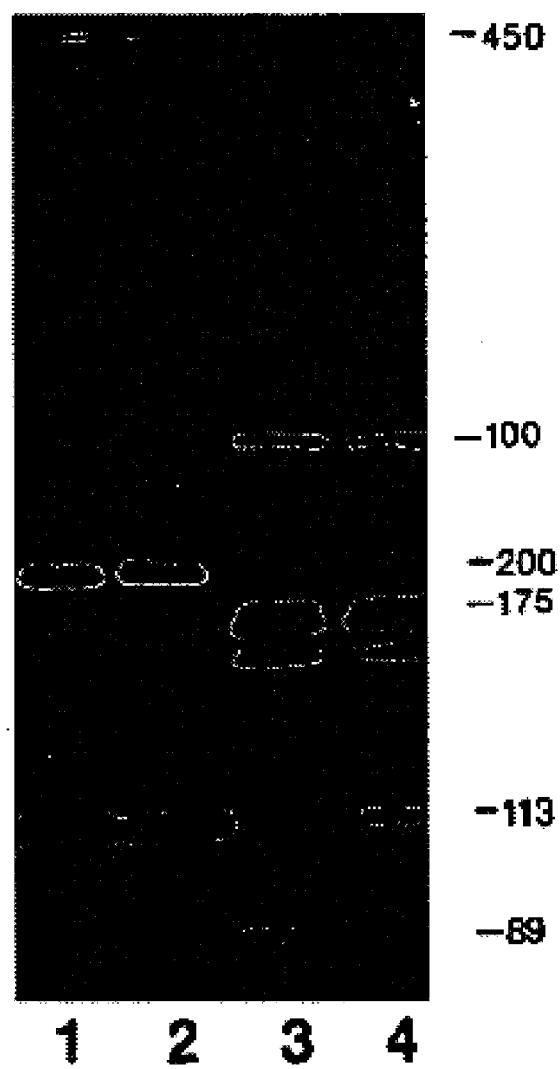
FIG. 6. Endogenous DNA-PK$_{cs}$, NuMA and PARP are cleaved after in vivo incubation of intact K562 cells with YT cell granule contents. K562 cells were incubated for 30 min at 37° C. in the absence (lanes 1–3) or presence (lane 4) of 100 µM Ac-DEVD-CHO. Aliquots of these cell suspensions (each containing 3×10$^5$ K562 cells) were then further incubated for 90 min at 37° C. in the presence of 1 mM Ca$^{2+}$ (lane 1), 1 mM EDTA+YT cell granule contents (lane 2) or 1 mM Ca$^{2+}$+YT cell granule contents (lanes 3 & 4). After terminating the reactions, DNA-PK$_{cs}$, NuMA and PARP were detected by immunoblotting as described in the Example 1 (Patient serum G.A. was used to blot DNA-PK$_{cs}$).

EXAMPLE 7
Granzyme B-specific Fragments of DNA-PK$_{cs}$ and NuMA are Generated During Cytotoxic Lymphocyte Granule-induced Target Cell Death To determine whether the granzyme B-specific fragments demonstrated in cell lysates also occur when target cell death is induced by the contents of cytolytic lymphocyte granules, The consequences of granule-induced target cell death on substrate cleavage were examined. Granules containing perforin and granzymes were purified from the human NK cell line, YT. The granule contents were harvested and used to induce target cell cytotoxicity as described in Example 1. Several different target cells (Jurkat T cells, K562 erythroleukemia cells, human myoblasts or HeLa cells) were incubated with granule contents (~1.5×10⁷ YT cell equivalents/ml) in the presence of $Ca^{2+}$. Rapid target cell lysis was induced (achieving ~20–40% specific $^{51}Cr$ release in 60 min). Target cell lysis by granule contents did not occur in the absence of $Ca^{2+}$ (Podack and Konigsberg, 1984; Young et al., 1986). $DNA-PK_{cs}$, NuMA and PARP were all cleaved rapidly after addition of granules, in a $Ca^{2+}$-dependent manner (FIG. 6, lanes 2 & 3). As observed in the lysate system described above, cleavage of PARP resulted almost completely in the generation of the 89 kDa caspase-3-specific fragment (FIG. 6, lane 3). Only small amounts of the 62 kDa granzyme B-specific fragment were generated. Generation of the 89 kDa fragment was completely inhibited by Ac-DEVD-CHO (FIG. 6, lane 4). In contrast, granule contents induced the formation of granzyme B-specific cleavage fragments of $DNA-PK_{cs}$ and NuMA (FIG. 6, lane 3). The production of these fragments was not inhibited by Ac-DEVD-CHO (FIG. 6, lane 4).

Note that in the case of $DNA-PK_{cs}$, addition of granule contents also resulted in the formation of small amounts of 150 kDa and 120 kDa fragments, which were only well visualized after longer exposures of the X-ray film. Generation of these fragments was also entirely inhibited by Ac-DEVD-CHO.

EXAMPLE 8

Figure 7:
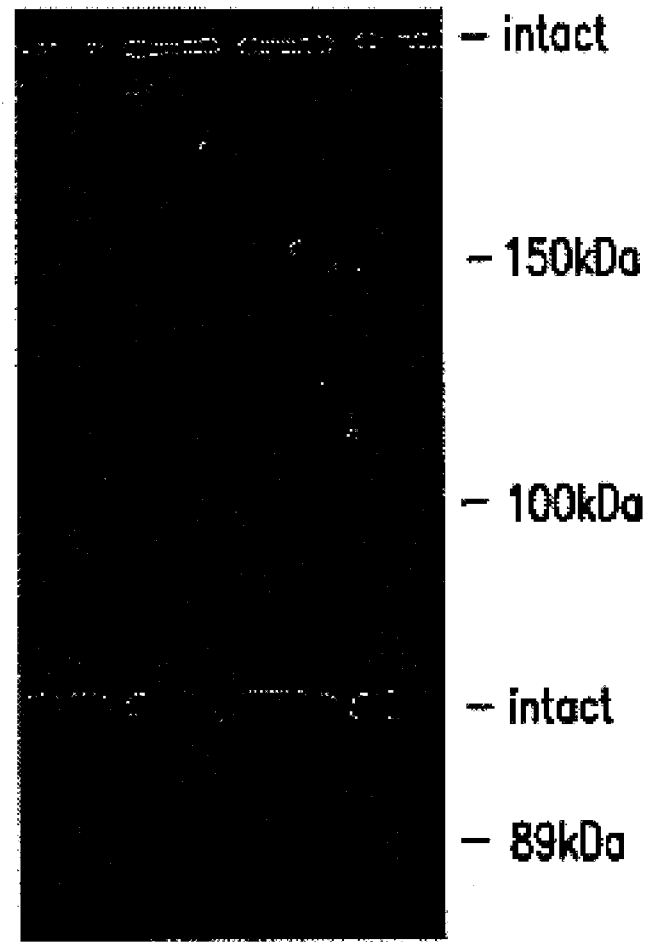
FIG. 7. Granzyme B-specific fragment of DNA-PK$_{cs}$ is generated in K562 cells attacked by LAK cells. Fas-negative K562 target cells were preincubated in the absence (lanes 1–3) or presence (lane 4) of 100 µM Ac-DEVD-CHO for 1 hr, followed by co-incubation for a further 4 hr at 37° C. (effector:target ratio 5:1). After terminating the reactions, the following numbers of cells were electrophoresed in each gel lane: 1.7×10$^6$ LAK cells (lane 1); 0.34×10$^6$ K562 cells (lane 2); 1.7×10$^6$ LAK cells plus 0.34×10$^6$ K562 cells (lanes 3 & 4). DNA-PK$_{cs}$ and PARP were detected by immunoblotting; patient serum GA. was used to detect DNA-PK$_{cs}$.

Granzyme B-specific Fragments of $DNA-PK_{cs}$ and NuMA Are Generated in Fas-negative Target Cells Attacked by Lymphokine-activated Killer (LAK) Cells To determine whether granzyme B-specific fragments were generated during lymphocyte-induced cytotoxicity, we used the Fas-negative cell line K562 as targets for LAK cells (McGahon et al. 1995; Topalian et al., 1989). To permit biochemical analysis of cleaved proteins in target cells, effector:target cell ratios of 5:1 were used. The signature 89 kDa caspase-3 fragment of PARP was generated during LAK-induced target cell death (FIG. 7, lane 3). PARP cleavage was entirely abolished by 100 μM Ac-DEVD-CHO (FIG. 7, lane 4). This was consistent with results observed when target cell death was initiated with YT cell granule contents (FIG. 6, lane 4). Using anti-C-terminal antibodies, generation of both the 100 kDa granzyme B-specific fragment of $DNA-PK_{cs}$ and the 150-kDa caspase-3-specific fragment were detected during LAK-induced target cell death (FIG. 7, lane 3). In addition, a 120 kDa fragment was observed in these cells, consistent with the caspase-3-mediated cleavage of $DNA-PK_{cs}$ at DWVD-G previously observed both in vitro and in intact cells (Casciola-Rosen et al., 1996; Song et al., 1996b). While 100 μM Ac-DEVD-CHO inhibited the generation of caspase-3-specific fragments of $DNA-PK_{cs}$ by >90%, the 100 kDa granzyme B-specific fragment was insensitive to this inhibitor (FIG. 7, lane 4). This data is consistent with that obtained after initiating target cell death with YT cell granule contents (FIG. 6, lane 4 and data not shown). Similar observations were made for the granzyme B-specific NuMA fragment. Together, these data confirm that the novel fragments of $DNA-PK_{cs}$ and NuMA defined in these studies are indeed generated when intact lymphocytes induce target cell cytotoxicity using the granule pathway.

EXAMPLE 9

Figure 8A:
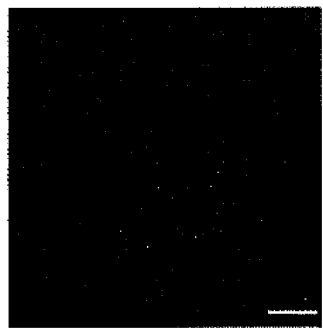
FIG. 8. Ac-DEVD-CHO-insensitive nuclear morphologic changes are induced in intact HeLa cells after in viuo incubation with YT cell granule contents. HeLa cells were incubated with YT cell granule contents for 1 hr at 37° C. in the absence (8A & 8B) or presence (8C) of 100 µM Ac-DEVD-CHO as described in Experimental Procedures. After fixation and permeabilization, cells were stained with antibodies to PARP, as well as propidium iodide (PI) and DAPI. Antibody staining was visualized with FITC-goat anti-human antibodies. Merged images of antibody staining (green), PI staining (red) and DAPI staining (blue) are presented. (8A, 8B): YT cell granule contents induce prominent PI-rich surface blebs, nuclear condensation and fragmentation, with a characteristic redistribution of PARP to the rim of the condensing nucleus (8A) or apoptotic bodies (8B, arrows). (8C): Granule contents induce marked nuclear condensation even in the presence of Ac-DEVD-CHO (arrows); an adjacent, normal HeLa cell nucleus that has not yet undergone morphologic change is shown for comparison (arrowhead). Note that treatment with Ac-DEVD-CHO abolishes the formation of PI-rich surface blebs, nuclear fragmentation, and the redistribution of PARP. Size bar: 8A: 4.4 µm; 8B: 4.0 µm, 8C: 6.6 µm.
Figure 8B:
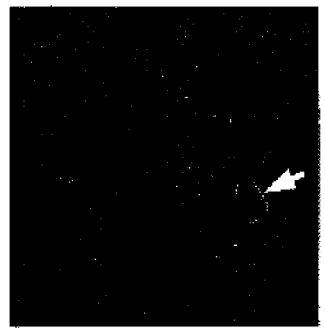
Figure 8C:
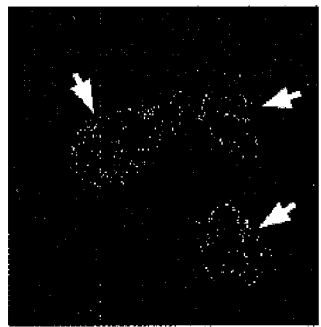

Cytotoxic Lymphocyte Granules Induce Nuclear Morphologic Changes: Effects of Caspase Inhibitors Several of the downstream substrates for the caspases are directly and efficiently cleaved by granzyme B during lymphocyte granule-induced cytotoxicity even in the presence of caspase inhibitors. It was determined whether these granules also induced morphologic changes in the target cell. HeLa cells were pre-incubated with YT cell granule contents in the presence or absence of 100 μM Ac-DEVD-CHO, prior to addition of $Ca^{2+}$, and further incubation. YT cell granule contents induced the rapid onset (<60 min) of prominent surface blebbing (FIG. 8A), followed by nuclear condensation and fragmentation into membrane-bound apoptotic bodies (FIG. 8B). As described for UVB-induced apoptosis (Casciola-Rosen et al. 1994), the autoantigens targeted in systemic autoimmune diseases are rapidly redistributed in target cells exposed to YT cell granule contents, such that they become clustered around the rim of the condensing apoptotic nucleus (FIG. 8A), and then ultimately around apoptotic bodies (FIG. 8B). Granule content-induced surface blebbing, nuclear fragmentation, formation of apoptotic bodies, and characteristic redistribution of nuclear autoantigens was prevented by Ac-DEVD-CHO (Compare FIGS. 8B, 8C). However, a prominent diminution in the size of the nucleus (which was accompanied by condensation of chromatin) was induced by granule contents in Ac-DEVD-CHO-treated cells (FIG. 8C); these nuclear changes were not observed when cells were incubated with Ac-DEVD-CHO alone.

EXAMPLE 10

Antibodies Against Autoantigens and Autoantigenic Fragments

The present invention also relates to polyclonal and monoclonal antibodies raised in response to the autoantigenic fragments disclosed herein. An antibody is specific for an epitope of an autoantigenic fragment if one of skill in the art can use standard techniques to determine conditions under which one can detect an autoantigenic fragment in a Western Blot of a sample from cells of a tissue. The blot can be of a native or denaturing gel as appropriate for the epitope. An antibody is highly specific for an autoantigenic fragment epitope if no nonspecific background binding is visually detectable. An antibody can also be considered highly specific for an autoantigenic fragment if the binding of the antibody can not be competed by random peptides, polypeptides or proteins, but can be competed by the particular autoantigenic fragment, autoantigen, or peptides or polypeptides derived therefrom.

Autoantigenic fragments can be separated from other cellular proteins by use of an immunoaffinity column made with monoclonal or polyclonal antibodies specific for the autoantigen. Additionally, polyclonal or monoclonal antibodies can be raised against a synthetic peptide (usually from about 9 to about 25 amino acids in length) from a portion of an autoantigen or autoantigenic fragment. Monospecific antibodies are purified from mammalian antisera containing antibodies reactive against the autoantigenic fragment or are prepared as monoclonal antibodies using the technique of Kohler and Milstein (1975, Nature 256: 495–497). Monospecific antibody as used herein is defined as a single antibody species or multiple antibody species with homogenous binding characteristics for the autoantigenic fragment. Homogenous binding as used herein refers to the ability of the antibody species to bind to a specific antigen or epitope, such as those associated with the autoantigenic fragment, as described herein. Autoantigenic fragment-specific antibodies are raised by immunizing animals such as mice, rats, guinea pigs, rabbits, goats, horses and the like, with an appropriate concentration of autoantigenic fragment or a synthetic peptide generated from a portion of the autoantigenic fragment with or without an immune adjuvant.

Preimmune serum is collected prior to the first immunization. Each animal receives between about 0.1 mg and about 1000 mg of autoantigenic fragment associated with an acceptable immune adjuvant. Such acceptable adjuvants include, but are not limited to, Freund's complete, Freund's incomplete, alum-precipitate, water in oil emulsion containing Corynebacterium parvum and RNA. The initial immunization consists of injecting autoantigenic fragment or peptide fragment thereof, preferably in Freund's complete adjuvant, at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of autoantigenic fragment in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with the autoantigenic fragment are prepared by immunizing inbred mice, preferably Balb/c, with the autoantigenic fragment. The mice are immunized by the IP or SC route with about 1 mg to about 100 mg, preferably about 10 mg, of the autoantigenic fragment in about 0.5 ml buffer or saline incorporated in an equal volume of an acceptable adjuvant, as discussed herein. Freund's complete adjuvant is preferred. The mice receive an initial immunization on day 0 and are rested for about 3 to about 30 weeks. Immunized mice are given one or more booster immunizations of about 1 to about 100 mg of the autoantigenic fragment in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners can include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using the autoantigenic fragment as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in Tissue Culture Methods and Applications, Kruse and Paterson, Eds., Academic Press.

Monoclonal antibodies are produced in vivo by injection of pristine primed Balb/c mice, approximately 0.5 ml per mouse, with about $2 \times 10^5$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-autoantigenic fragment mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of the autoantigenic fragment in body fluids or tissue and cell extracts.

It is readily apparent to those skilled in the art that the herein described methods for producing monospecific antibodies can be utilized to produce antibodies specific for autoantigenic fragment peptide fragments, or full-length autoantigen.

Antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing the autoantigenic fragment are slowly passed through the column. The column is then washed with phosphate buffered saline until the optical density ($A_{280}$) falls to background, then the protein is eluted with 0.23 M glycine-HCl (pH 2.6). The purified autoantigenic fragment is then dialyzed against phosphate buffered saline.

Levels of an autoantigenic fragment in cells and tissues is quantified by a variety of techniques including, but not limited to, immunoaffinity and/or ligand affinity techniques. Autoantigenic fragment affinity beads or autoantigenic fragment-specific antibodies are used to isolate $^{35}S$-methionine labeled or unlabelled autoantigenic fragment. Labeled autoantigenic fragment is analyzed by SDS-PAGE. Unlabelled autoantigenic fragment is detected by Western blotting, ELISA or RIA assays employing either autoantigenic fragment specific antibodies and/or antiphosphotyrosine antibodies.

Preferred antibodies that bind to an autoantigenic fragment but do not bind to the intact autoantigen or other fragments thereof. Examples of preferred antibodies are those that recognizes a cryptic epitope revealed in the autoantigenic fragment, or an antibody that recognizes a terminal epitope present only in the autoantigenic fragment.

EXAMPLE 11
Assay for the Detection of an Autoimmune Condition

The autoantigenic fragments produced and identified following the teaching of the present invention can be used in a assay to detect the presence of an autoimmune condition. The condition can be the generation of autoantigenic fragments before a disease state evolves, the presence of an autoimmune disease or the lessening of a disease.

The assay is performed on a sample derived from a patient. Most commonly, the sample will be a tissue sample.

The presence of autoantigenic fragments can be detected in situ or can be partially purified before conducting the assay.

To perform an assay within this invention one prepares an autoantigenic fragment. For example, one can prepare an autoantigenic fragment of DNA $PK_{cs}$ by cleaving the protein with granzyme B. The autoantigenic fragment is then used to prepare a monoclonal or polyclonal antibody using any of the methods widely known and used in the art.

The antibody can then be used to qualify or quantify the amount of autoantigenic fragment present in the sample. This can be done by numerous techniques known in the art including using antibody detectably labeled with $^{125}I$, gold, enzyme or other known labels. Alternatively, a detectable label can be carried on a second antibody specific for the first. The amount of autoantigenic fragment found is quantitatively or qualitatively compared to the amount of found on control cells. A change in the former relative to the latter is indicative of whether an autoimmune disease state is present, is progressing or is reduced.

In an alternative form of the assay one can treat cells as described herein and then isolate the autoantigenic fragments present in treated and control cells. The preparations can be made as crude cell extracts, membrane or intracellular fractions of the cells or after purification steps, e.g., chromatography, precipitation or affinity isolation steps. Crude, partially or highly purified preparations can be analyzed for autoantigenic fragment content, e.g., by using antibodies specific for the autoantigenic fragment.

In another form of the assay, an autoantigenic fragment is used to determine the presence or absence of an autoantibody in a patient as an indication of the presence or absence of an autoimmune condition. The use of particular types or autoantigenic fragments can also indicate the type of autoimmune condition. The autoantibody to be assayed for can be present in the serum or a tissue sample of the patient. An autoantibody can be detected in situ or after some purification of immunoglobins from the patient. In one format of the assay, the autoantigenic fragment can be fixed to a support, an autoantibody present in a sample is then contacted with the fragment to permit binding of the autoantibody to the autoantigenic fragment. After appropriate washing, the presence of bound autoantibody can be detected by methods available in the art, including the use of a labeled second antibody against the antibodies from the patient.

In any assay it can be advantageous to devise an internal control so that the results of different runs of assays can be compared to each other. A cellular protein that is unrelated to the autoantigenic fragment and present in relatively constant amounts in the cells used in the assay can serve as an internal control.

The assays described above are exemplary of all of the assays within the scope of the present invention. Those of skill in the art can use the autoantigenic fragments and antibodies of this invention in many assay formats known or developed in the art.

EXAMPLE 12

Tolerizing a Patient to the Presence of an Autoantigenic Fragment

The present invention provides a method of tolerizing a patient to the future in vivo generation of compounds that are normally autoantigenic. This method can be prophylactic.

A patient diagnosed to be at risk of developing an autoimmune response is identified. A sample of the tissue to which the autoimmune response is possible is isolated from the patient. Autoantigenic fragments that can be generated from the tissue are then identified. The autoantigenic fragments are administered to the patient in pharmaceutically acceptable carriers without an adjuvant to induce low-zone tolerance.

Tolerization typically involves purification of relevant autoantigenic fragments in a non-aggregated form. In particular embodiments, autoantigenic fragments of DNA $Pk_{cs}$, NuMA or PARP are generated by the action of granzyme B.

The autoantigenic fragments can also be present in a mixture. One such mixture can be the product of the application of the contents of granules to a sample of tissue to which a potential autoimmune response is diagnosed. In that case, the autoantigenic fragments are produced in the mixture by the action of the granule contents, including granzyme B.

In any case, the autoantigenic fragments are administered at a low dose as chosen by a skilled physician or veterinarian to induce a low-zone tolerance in the patient. Once tolerization of the patient is achieved, if the normally autoantigenic fragments are produced in the tissue in vivo, the immune system will not mount a response against them and the occurrence of an autoimmune disease state can be avoided or the severity reduced.

EXAMPLE 13

Treatment for Malignant Cells

The present invention also provides a method of generating an autoimmune response against certain cells in a patient. For example, one can induce an autoimmune response against malignant cells in a patient that would benefit from such a response.

For example, one can isolate a sample of malignant cells from a patient and contact the cells with the contents of granules or granzyme B. The action of the granule contents or granzyme B on the cells can produce autoantigenic fragments from autoantigens present in the cells. The resulting mixture can then be administered to the patient. In this case, it is preferred that an adjuvant be administered with the autoantigenic fragments.

Those components of the mixture that are not altered to produce a new antigen will be recognized by the immune system as self molecules. However, those components that are altered to produce new autoantigenic fragments will be seen by the immune system as non-self and an immune response will be generated against them.

Because the autoantigenic fragments produced in this way are the same as those produced in vivo by the action of CTLs, NK and LAK cells on the malignant cells, the immune system is stimulated to generate a response against the malignant cells. Therefore, the present invention provides a method to heighten or stimulate the natural immune system processes to act against particular types of cells such as malignant cells. The method is particularly advantageous because the in vivo production of the autoantigenic fragments from, e.g., malignant cells, can occur at rates too low to stimulate the immune system, or at rates that can lead to a tolerization of the immune system.

EXAMPLE 14

Pharmaceutical Compositions

Pharmaceutically useful compositions comprising autoantigenic fragments of the present invention can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the inhibitor.

Therapeutic, prophylactic or diagnostic compositions of the invention are administered to an individual in amounts sufficient to treat or diagnose disorders. The effective amount can vary according to a variety of factors such as the individual's condition, weight, sex and age. Other factors include the mode of administration. The appropriate amount can be determined by a skilled physician The pharmaceutical compositions can be provided to the individual by a variety of routes such as subcutaneous, topical, oral and intramuscular.

The term "chemical derivative" describes a molecule that contains additional chemical moieties which are not normally a part of the base molecule. Such moieties can improve the solubility, half-life, absorption, etc. of the base molecule. Alternatively the moieties can attenuate undesirable side effects of the base molecule or decrease the toxicity of the base molecule. Examples of such moieties are described in a variety of texts, such as Remington's Pharmaceutical Sciences.

Compositions including autoantigenic fragments identified according to the methods disclosed herein can be used alone at appropriate dosages. Alternatively, co-administration or sequential administration of other agents can be desirable.

The present invention also provides a means to obtain suitable topical, oral, systemic and parenteral pharmaceutical formulations for use in the methods of treatment of the present invention. The compositions containing autoantigenic fragments identified according to this invention as the active ingredient can be administered in a wide variety of therapeutic dosage forms in conventional vehicles for administration. For example, the compositions can be administered in such oral dosage forms as tablets, capsules (each including timed release and sustained release formulations), pills, powders, granules, elixirs, tinctures, solutions, suspensions, syrups and emulsions, or by injection, as appropriate. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, autoantigenic fragments of the present invention can be administered in a single daily dose, or the total daily dosage can be administered in divided doses of two, three or four times daily.

Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing compositions of the present invention is selected in accordance with a variety of factors including type, species, age, weight, sex and medical condition of the patient; whether the treatment is prophylactic or therapeutic; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of compounds of this invention, including purified autoantigenic fragments, within the range that yields efficacy without toxicity requires a regimen based on the kinetics of the compound's availability to target sites. This involves a consideration of the distribution, equilibrium, and elimination of a compound.

EXAMPLE 15

Autoantigens Cleaved by Granzyme B

Granzyme B efficiently cleaves three caspase-3 substrates generating unique fragments not generated during any other form of cell death. To determine whether the generation of unique autoantigen fragments by granzyme B was a universal feature of autoantigens, a wide range of autoantigens were tested for cleavage by granzyme B in vitro and in vivo. It was determined that despite their diverse structure, distribution and function, >70% of the autoantigens described in systemic autoimmune diseases are efficiently cleaved by granzyme B and unique fragments are produced. In contrast, granzyme B does not generate unique fragments in all the non-autoantigen molecules tested. A panel of autoantigens discovered to be susceptible to cleavage by granzyme B, are listed in Table 3 along with the sites of cleavage.

The granzyme B cleavage sites in autoantigens were defined. In all cases, the tetrapeptide sequence immediately adjacent to the cleavage site was highly conserved. The susceptibility to granzyme B cleavage is therefore a specific, unifying feature of these otherwise unrelated molecules. Furthermore, the ability of granzyme B to generate unique fragments of these antigens indicates that granzyme B plays a mechanistic role in selectively producing the fragments of these molecules against which autoimmune responses are initiated. These results highlight a potential role for the cytotoxic lymphocyte granule-induced death pathway in initiation and propagation of autoimmunity.

To determine whether susceptibility to direct cleavage by granzyme B was an isolated feature of PARP, NuMA and DNA-PK$_{cs}$ shown above, or whether it was a more general feature of autoantigens, a variety of well-defined autoantigens selected from across the spectrum of systemic autoimmune diseases were tested for susceptibility to cleavage by purified granzyume B. The efficiency of cleavage of the substrates by purified granzyme B was also noted (Table 3). Initially, a series of autoantibodies of well-defined specificity were used to immunoblot lysates of HeLa cells that had been incubated in vitro with or without granzyme B. Lysates were pre-treated with iodoacetamide (IAA) to prevent interference by endogenous caspase activity.

Interestingly, several autoantigens that have previously been shown to be cleaved by caspases during apoptosis were also efficiently cleaved by granzyme B. These substrates included U1-70 kDa, topoisomerase-1, SRP-72, PARP and NOR-90. In each case, unique fragments were generated. Mi-2, PMS2 and Ki-67 were also identified as additional autoantigens that are cleaved into distinct, different sets of fragments both by caspases and by granzyme B in these lysates.

Efficient cleavage and generation of novel fragments was also confirmed using purified granzyme B to cleave in vitro translated substrates in the case of U1-70 kDa, PARP, topoisomerase-1, PMS2, and Mi-2. The cleavage efficiency ($k_{cat}/K_m$) of those substrates by granzyme B was determined using defined amounts of purified protease to cleave either endogenous substrates in cell lysates or radiolabeled substrates expressed by in vitro transcription/translation, or both. Previous studies have demonstrated that equivalent results are obtained using either form of substrate (Andrade et al., 1998). $k_{cat}/K_m$ values varied between $1.39 \times 10^4$ $M^{-1}.s^{-1}$ (PMS2) and $1.6 \times 10^6$ M-1.s$^{-1}$ (topoisomerase-1) (see Table 3).

Previous studies have identified several autoantigens that are not susceptible to cleavage by caspases during apoptosis (Casciola-Rosen et al., 1995 & 1996). Many of these autoantigens were efficiently cleaved by granzyme B. These molecules included fibrillarin, PMS1, CENP-B, Ku-70, La and RNA polymerase II large subunit. The efficiency of cleavage of these substrates by granzyme B varied between $5.9 \times 10^3$ $M^{-1}.s^{-1}$ (CENP-B) and $8 \times 10^4$ $M^{-1}.s^{-1}$ (La) (See Table 3). Interestingly, several ribonucleoprotein autoantigens were not susceptible to cleavage by either granzyme B or caspases. These included Ro52 kDa and 60 kDa, ribosomal protein P, histones and Sm proteins.

Susceptibility to cleavage by granzyme B was a highly specific feature of autoantigens. None of 18 different human non-autoantigens tested was cleaved by granzyme B. The precursors of caspases 3 and 7 are not known to be autoantigens, but are efficiently cleaved by granzyme B. Interestingly, these substrates are cleaved at the same sites by granzyme B and caspase-8, generating identical fragments (see below).

Since some well-defined autoantibodies do not recognize their antigens by immunoblotting, the susceptibility of radiolabeled endogenous substrates to cleavage by granzyme B in vitro was assessed. To perform these studies, HeLa cells were radiolabeled with [$^{35}$S] methionine/cysteine, and proteins were immunoprecipitated using human autoantibodies. Protein A-agarose beads containing washed precipitated proteins were resuspended in buffer supporting the activity of granzyme B, and incubated in the absence or presence of added purified granzyme B. Reaction products were visualized using SDS-PAGE and fluorography. To confirm the validity of this approach, several different autoantigens known to be cleaved by granzyme B, as well as several autoantigens and non-autoantigens that are not cleaved by granzyme B, were tested. Using autoantibodies that both immunoblot and immunprecipitate, the cleavage profiles obtained using granzyme B to cleave molecules in lysates (followed by detection with immunoblotting), and after immunoprecipitation (from [$^{35}$S] methionine-labeled HeLa lysate) were compared. Identical results were obtained using these 2 methods for cleaved autoantigens (topoisomerase-1, Mi-2, RNA polymerase II large subunit, Ku-70, PARP, and NOR-90), uncleaved autoantigens (Ku-80, Ro 60k), and control substrates (β-tubulin, vinculin). Using this immunoprecipitation approach, it was demonstrated that several additional autoantigens (PMScl, RNA polymerase I large subunit, histidyl tRNA synthetase, isoleucyl tRNA synthetase and alanyl tRNA synthetase) were cleaved by granzyme B, generating unique fragments (Table 3). Of note, all these additional autoantigens (with the exception of RNA polymerase I) are targeted in autoimmune myositis. However, two other tRNA synthetases (threonyl tRNA synthetase and glycyl tRNA synthetase) that are also autoantigens in autoimmune myositis, were not cleaved using this approach.

Thus, in addition to the three autoantigens described above to be cleaved by both caspase-3 and granzyme B, these results identify an additional 7 autoantigens have been identified that are cleaved by both proteases but at different sites. Furthermore, another 10 autoantigens are cleaved exclusively by granzyme B, and not by caspases. Therefore, 20 autoantigens targeted across the spectrum of human systemic autoimmune diseases are efficiently cleaved by granzyme B, generating unique fragments not observed during other forms of cell death. (Table 3).

To confirm that similar autoantigen fragments are generated in intact cells during granule-induced cell death, K562 cells were exposed to YT cell granule contents in the presence of $Ca^{2+}$, and the biochemical status of the autoantigens were analyzed by immunoblotting. In those cases where autoantigens are substrates for both caspases and granzyme B, both fragments were generated (U1-70 kDa, PARP, Mi-2, topoisomerase-1, Ki-67). Autoantigens known to be cleaved only by granzyme B were indeed cleaved in the K562/YT granule system and the granzyme B-specific fragments of Ku-70, PMS-1 and RNA polymerase II large subunit were generated.

It was shown that granzyme B-specific fragments of DNA-PKcs are generated during cytotoxic lymphocyte granule-induced target cell death. A similar approach was used to determined whether other autoantigens cleaved by granzyme B in vitro are also cleaved during killing of intact Fas-negative target cells by lymphokine-activated killer (LAK) cells. Granzyme B-specific fragments of Mi-2, U1-70 kDa, topoisomerase-1, PMS-1 and SRP-72 as well as Ku-70, RNA polymerase II and Ki-67, are generated during this form of cell death and were identified by immunoblotting with appropriate antibodies. In the cases of Mi-2, U1-70 kDa, SRP-72 and topoisomerase-1, which are all susceptible to direct cleavage by both caspase-3 and granzyme B, the amounts of granzyme B-specific fragments of these antigens appear to be determined by the relative efficiency of cleavage by the two proteases. Thus, granzyme B-specific fragments of Mi-2 and topoisomerase-1 (which are efficiently cleaved by granzyme B) were clearly observed. In contrast, very low levels of granzyme B-specific fragments of U1-70 kDa, SRP-72 or the less efficiently cleaved sites on toposiomerase-1 (72 and 75 kDa) were observed in the intact cell killing assay unless caspases were inhibited by adding Ac-DEVD-CHO. The cleavage of PMS1, which is a substrate for granzyme B but not for caspases, was unaffected by Ac-DEVD-CHO.

EXAMPLE 16
Specificity of Granzyme B Cleavage of Autoantigens

Granzyme B is a serine protease whose specificity has been defined using a positional scanning combinatorial tetrapeptide library. The protease has a preference for I,V or L in $P_4$, E, G, S in $P_3$, and P, S, N, A, Q, H, T, V, E, D, in $P_2$, with a preference for D in $P_1$. The sizes of the fragments generated by granzyme B cleavage and the cleavage specificity was used to identify likely cleavage sites. Since granzyme B prefers Asp in the $P_1$ position, and does not tolerate Ala at that site, site-directed mutagenesis was employed to make a series of Asp-Ala substitutions in several of the granzyme B substrates. The effects of each mutation on the efficiency of cleavage by the protease was assessed.

The granzyme B cleavage sites in PARP and DNA-PKcs have been defined. Using the above approach, the granzyme B cleavage sites in fibrillarin, Mi-2, topoisomerase 1, PMS1, PMS2, and U1-70 kDa were also defined (Table 3). Interestingly, 10 of 11 of these cleavage sites contain P (7), A (2), or S (1) in the $P_2$ position, which are preferred by granzyme B but are poorly tolerated by group III caspases. Furthermore, 4 cleavage sites also contain G or S in $P_3$. These residues are also not tolerated by group III caspases. Using fragment sizes to predict likely granzyme B cleavage sites in other autoantigens, likely cleavage sites were also identified in these proteins. In every case, these cleavage sites contained residues in $P_2$ and/or $P_3$ which are preferred by granzyme B, but are not tolerated by group III caspases (Table 3).

To confirm that these substrates were not cleaved by group III caspases, the substrates were incubated with 50 nM purified caspase-8. Cleavage assays were performed in HeLa cell lysates in which endogenous caspases had first been irreversibly inactivated by 1 mM iodoacetamide (4° C. for 15 min), prior to addition of 5 mM DTT to facilitate exogenous caspase-8 activity. No cleavage of topoisomerase-1, Mi-2, U1-70 kDa, PARP, Ku-70, RNA polymerase II large subunit, SRP-72, NuMA or Ki-67 occurred. Caspase-8 was indeed active in these lysates, as evidenced by robust caspase-3 cleavage products of PARP and U1-70 kDa seen when the IAA 'poisoning' step was omitted. Radiolabeled PMS1 and PMS2 (generated by IvTT) were also not cleaved by purified caspase-8.

It was demonstrated that 20 of 28 autoantigens tested were susceptible to efficient cleavage by granzyme B, generating unique fragments. Although the cleaved molecules differ markedly in subcellular location, function, and extended primary sequence, they share 2 features: (i) all are autoantigens targeted by a high titer autoantibody response in human autoimmune diseases, including SLE, Sjogren's syndrome, diffuse and limited scleroderma, and autoimmune myositis; and (ii) molecules are unified by containing a granzyme B cleavage site not susceptible to cleavage by caspase-8 (see below). Interestingly, autoantibodies against the precursors of caspases 3 and 7 (which are cleaved by granzyme B and caspase-8 cleave at the same sites generating identical fragments) have not been found in >1000 autoimmune sera screened by immunoblotting.

The status of a molecule as an autoantigen and its unique susceptibility to cleavage by granzyme B but not by caspase-8, are therefore highly related ($P<0.0001$; Chi-square analysis). The positive predictive value of susceptibility to unique cleavage by granzyme B and status as an autoantigen is 100% for these 48 substrates, while the negative-predictive value is 73%, indicating that additional mechanisms play a role in selection of some molecules as autoantigens. It is noteworthy that most of the uncleaved molecules are nucleoprotein complexes (e.g. components of nucleosomes and snRNPs).

The granzyme B cleavage sites in several molecules are highly conserved, even in drosophila and yeast. This striking conservation of sequence at granzyme B cleavage sites in organisms in which cytotoxic lymphocytes had not yet evolved implies that an important, as yet undefined function is served by these regions. This new, extended family of granzyme B substrates therefore provide a powerful tool with which to explore the evolution and biological functions of the aspartic acid-specific apoptotic proteases, and to probe the mechanisms of cytotoxic lymphocyte granule-mediated cell death.

Human systemic autoimmune diseases represent a highly complex disease spectrum, with numerous variables affecting individual susceptibility, initiation, and tissue targets. By demonstrating that the autoantigens targeted across the spectrum of these diseases are unified by their susceptibility to efficient cleavage by granzyme B, with the generation of unique fragments not generated during any other form of cell death, these studies focus attention on the role of the cytotoxic lymphocyte granule pathway in initiation of autoimmunity. Where substrates are cleaved by both caspases and granzyme B, generation of unique granzyme B fragments is dependent on relative inhibition of the caspases. Without wishing to be bound by a particular theory, it is therefore proposed that during pro-immune intracellular infections occurring in a microenvironment in which caspase activity is under relative inhibition, production of unique granzyme B fragments is favored. In susceptible individuals in whom clearance of apoptotic material is impaired, suprathreshold amounts of these fragments accumulate and are effectively captured and presented by dendritic cells. The resulting immune response is directed against products of CTL granule-induced death, generating an autoamplifying injury characteristic of these self-sustaining diseases.

EXAMPLE 17

Screening for Candidate Agents for Treatment

The assays described herein can be adapted for screening for candidate agents for the prophylactic or therapeutic treatment of autoimmune disease, cancer, or the symptoms of such diseases. In an exemplary format, a candidate agent is contacted with both an uncleaved autoantigen and the contents of a lymphocyte granule, a granule enzyme, or granzyme B. The granule enzyme or granzyme B can be prepared in varying degrees of purity. The autoantigen should be a substrate cleavable by the granule contents or, if a purified or partially purified enzyme is used, a substrate for the particular enzyme. Once contacted, one can monitor the cleavage of the autoantigen into autoantigenic fragments. If desired, one can run a control assay with no candidate agent, or a known inhibitor of the enzyme, in parallel. The production of autoantigenic fragments can be monitored by a variety of means known in the art including antibody capture of the epitopes produced through cleavage, the loss of epitopes that span the cleavage site, separation of cleavage products through chromatography or electrophoresis and other techniques known and used in the art or developed subsequently in the art of detection. A screening assay can be quantitative or qualitative.

A candidate agent can be a chemical compound, organic or inorganic, or a biochemical compound including proteins, peptides, glyco-proteins or peptides, polysaccharides or other macromolecules.

A candidate agent that decreases the rate or the amount of cleavage of the autoantigen to autoantigenic fragments is referred to as an inhibitor of the process. Candidate agents can be studied to determine their suitability for application in the treatment of animals and humans by methods and procedure recognized in the art of pharmaceutical sciences. Those candidates which through testing are shown to have appropriate efficacy and an acceptable safety profile are used in the prophylactic or therapeutic treatment of patients.

REFERENCES

Andrade, F., Roy, S., Nicholson, D., Thornberry, N., Rosen, A., and Casciola-Rosen, L. 1998. Granzyme B Directly and Efficiently Cleaves Several Downstream Caspase Substrates: Implications for CTL-Induced Apoptosis Immunity 8:451–460.

Bach, J. F. and S. Koutouzov. (1997). New clues to systemic lupus. *Lancet* 350:11–11.

Beidler, D. R., Tewari, M., Friesen, P. D., Poirier, G., and Dixit, V. M. (1995). The baculovirus p35 protein inhibits Fas- and tumor necrosis factor-induced apoptosis. J.Biol.Chem. 270, 16526–16528.

Bockenstedt, L. K., R. J. Gee, and M. J. Mamula. (1995). Self-peptides in the initiation of lupus autoimmunity. *J.Immunol.* 154:3516–3524.

Bump, N. J., Hackett, M., Hugunin, M., Seshagiri, S., Brady, K., Chen, P., Ferenz, C., Franklin, S., Ghayur, T., Li, P., Licari, P., Mankovich, J., Shi, L. F., Greenberg, A. H., Miller, L. K., and Wong, W. W. (1995). Inhibition of ICE family proteases by baculovirus antiapoptotic protein p35. Science 269, 1885–1888.

Burlingame, R. W., R. L. Rubin, R. S. Balderas, and A. N. Theofilopoulos. (1993). Genesis and evolution of anti-chromatin autoantibodies in murine lupus implicates T-dependent immunization with self-antigen. *J.Clin.Invest.* 91:1687–1696.

Casciola-Rosen, L. A., Anhalt, G. J., and Rosen, A. (1994a). Autoantigens targeted in systemic lupus erythematosus are clustered in two populations of surface structures on apoptotic keratinocytes. J. Exp. Med. 179, 1317–1330.

Casciola-Rosen, L. A., Miller, D. K., Anhalt, G. J., and Rosen, A. (1994b). Specific cleavage of the 70-kDa protein component of the U1 small nuclear ribonucleoprotein is a characteristic biochemical feature of apoptotic cell death. J.Biol.Chem. 269, 30757–30760.

Casciola-Rosen, L. A., Anhalt, G. J., and Rosen, A. (1995). DNA-dependent protein kinase is one of a subset of autoantigens specifically cleaved early during apoptosis. J.Exp.Med. 182, 1625–1634.

Casciola-Rosen, L. A., Nicholson, D. W., Chong, T., Rowan, K. R., Thornberry, N. A., Miller, D. K., and Rosen, A. (1996). Apopain/CPP32 cleaves proteins that are essential for cellular repair: A fundamental principle of apoptotic death. J.Exp.Med. 183, 1957–1964.

Casciola-Rosen, L. and A. Rosen. (1997). Ultraviolet light-induced keratinocyte apoptosis: A potential mechanism for the induction of skin lesions and autoantibody production in LE. *Lupus* 6:175–180.

Casiano, C. A., Martin, S. J., Green, D. R., and Tan, E. M. (1996). Selective cleavage of nuclear autoantigens during CD95 (Fas/APO-1)-mediated T cell apoptosis. J.Exp.Med. 184, 765–770.

Chinnaiyan, A. M. and Dixit, V. M. (1996a). The cell-death machine. Curr.Biol. 6, 555–562.

Chinnaiyan, A. M., Hanna, W. L., Orth, K, Duan, H. J., Poirier, G. G., Froelich, C. J., and Dixit, V. M. (1996b). Cytotoxic T-cell-derived granzyme B activates the apoptotic protease ICE-LAP3. Curr.Biol. 6, 897–899.

Darmon, A. J., Ley, T. J., Nicholson, D. W., and Bleackley, R. C. (1996). Cleavage of CPP32 by granzyme B represents a critical role for granzyme B in the induction of target cell DNA fragmentation. J.Biol.Chem. 271, 21709–21712.

Darmon, A. J., Nicholson, D. W., and Bleackley, R. C. (1995). Activation of the apoptotic protease CPP32 by cytotoxic T-cell-derived granzyme B. Nature 377, 446–448.

Deveraux, Q. L., Takahashi, R., Salvesen, G. S. and Reed, J. C. (1997). X-linked IAP is a direct inhibitor of cell-death proteases. Nature 38, 300–304.

Diamond, B., J. B. Katz, E. Paul, C. Aranow, D. Lustgarten, and M. D. Scharff. (1992). The role of somatic mutation in the pathogenic anti-DNA response. *Ann.Rev.Immunol.* 10:731–757.

Duan, H., Orth, K., Chinnaiyan, A. M., Poirier, G. G., Froelich, C. J., He, W.-W., and Dixit, V. M. (1996). ICE-LAP6, a novel member of the ICE/Ced-3 gene family, is activated by the cytotoxic T cell protease granzyme B. J.Biol.Chem. 271, 16720–16724.

Fernandes-Alnemri, T., Armstrong, R. C., Krebs, J., Srinivasula, S. M., Wang, L., Bullrich, F., Fritz, L. C., Trapani, J. A., Tomaselli, K. J., Litwack, G., and Alnemri, E. S. (1996). In vitro activation of CPP32 and Mch3 by Mch4, a novel human apoptotic cysteine protease containing two FADD-like domains. Proc.Natl.Acad.Sci.USA 93, 7464–7469.

Froelich, C. J., Hanna, W. L., Poirier, G. G., Duriez, P. J., D'Amours, D., Salvesen, G. S., Alnemri, E. S., Earnshaw, W. C., and Shah, G. M. (1996a). Granzyme B perforin-mediated apoptosis of jurkat cells results in cleavage of poly(ADP-ribose) polymerase to the 89-kDa apoptotic fragment and less abundant 64-kDa fragment. Biochem..Biophys.Res.Commun. 227, 658–665.

Froelich, C. J., Orth, K., Turbov, J., Seth, P., Gottlieb, R., Babior, B., Shah, G. M., Bleackley, R. C., Dixit, V. M., and Hanna, W. (1996b). New paradigm for lymphocyte granule-mediated cytotoxicity—Target cells bind and internalize granzyme B, but an endosomolytic agent is necessary for cytosolic delivery and subsequent apoptosis. J.Biol.Chem. 271, 29073–29079.

Ghayur, T., Hugunin, M., Talanian, R. V., Ratnofsky, S., Quinlan, C., Emoto, Y., Pandy, P., Datta, R., Huang, Y., Kharbanda, S., Allen, H., Kamen, R., Wong, W., and Kufe, D. (1996). Proteolytic activation of protein kinase C d by an ICE/CED-3-like protease induces features of apoptosis. J.Exp.Med. 184, 2399–2404.

Greidinger, E. L., Miller, D. K, Yamin, T.-T., Casciola-Rosen, L., and Rosen, A. (1996). Sequential activation of three distinct ICE-like activities in Fas-ligated Jurkat cells. FEBS Lett. 390, 299–303.

Gu, Y., Sarnecki, C., Fleming, M. A., Lippke, J. A., Bleakley, R. C., and Su, M. S. S. (1996). Processing and Activation of CMH-1 by Granzyme B. J.Biol.Chem 271, 10816–10820.

Heusel, J. W., Wesselschmidt, R. L., Shresta, S., Russell, J. H., and Ley, T. J. (1994). Cytotoxic lymphocytes require granzyme B for the rapid induction of DNA fragmentation and apoptosis in allogeneic target cells. Cell 76, 977–987.

Irmler, M., Thome, M., Hahne, M., Schneider, P., Hofmann, B., Steiner, V., Bodmer, J. L., Schröter, M., Burns, K, Mattmann, C., Rimoldi, D., French, L. E., and Tschopp, J. (1997). Inhibition of death receptor signals by cellular FLIP. Nature 388, 190–195.

Jacobson, M. D., Weil, M., and Raff, M. C. (1997). Programmed cell death in animal development. Cell 88, 347–354.

Jans, D. A., Jans, P., Briggs, L. J., Sutton, V., and Trapani, J. A. (1996). Nuclear transport of granzyme B (fragmentin 2). Dependence on perforin in vivo and cytosolic factors in vitro . J.Biol.Chem. 271, 30781–30789.

Krajewska, M., Wang, H. G., Krajewski, S., Zapata, J. M., Shabaik, A., Gascoyne, R., and Reed, J. C. (1997). Immunohistochemical analysis of in vivo patterns of expression of CPP32 (Caspase-3), a cell death protease. Cancer Res. 57, 1605–1613.

Krajewski, S., Gascoyne, R. D., Zapata, J. M., Krajewska, M., Kitada, S., Chhanabhai, M., Horsman, D., Berean, K., Piro, L. D., Fugier-Vivier, I., Liu, Y. J., Wang, H. G., and Reed, J. C. (1997). Immunolocalization of the ICE/Ced-3-family protease, CPP32 (Caspase-3), in non-Hodgkin's lymphomas, chronic lymphocytic leukemias, and reactive lymph nodes. Blood 89, 3817–3825.

Lanzavecchia, A. (1995). How can cryptic epitopes trigger autoimmunity? J.Exp.Med. 181,1945–1948.

Liu, X., Zou, H., Slaughter, C., and Wang, X. (1997). DFF, a heterodimeric protein that functions downstream of caspase-3 to trigger DNA fragmentation during apoptosis. Cell 89, 175–184.

Mamula, M. J. (1993). The inability to process a self-peptide allows autoreactive T cells to escape tolerance. *J.Exp.Med.* 177:567–571.

Martin, S. J., Amarante-Mendes, G. P., Shi, L. F., Chuang, T. H., Casiano, C. A., O'Brien, G. A., Fitzgerald, P., Tan, E. M., Bokoch, G. M., Greenberg, A. H., and Green, D. R. (1996). The cytotoxic cell protease granzyme B initiates apoptosis in a cell-free system by proteolytic processing and activation of the ICE/CED-3 family protease, CPP32, via a novel two-step mechanism. EMBO J. 15, 2407–2416.

Martin, S. J. and Green, D. R. (1995). Protease activation during apoptosis: Death by a thousand cuts? Cell 82, 349–352.

McGahon, A. J., Nishioka, W. K., Martin, S. J., Mahboubi, A., Cotter, T. G. and Green, D. R. (1995). Regulation of the Fas apoptotic cell death pathway by Abl. J. Biol. Chem. 270, 22625–22631.

Muzio, M., Chinnaiyan, A. M., Kischkel, F. C., O'Rourke, K., Shevchenko, A., Ni, J., Scaffidi, C., Bretz, J. D., Zhang, M., Gentz, R., Mann, M., Krammer, P. H., Peter, M. E., and Dixit, V. M. (1996). FLICE, a novel FADD-homologous ICE/CED-3-like protease, is recruited to the CD95 (Fas/APO-1) death-inducing signaling complex. Cell 85, 817–827.

Nicholson, D. W., Ali, A., Thornberry, N. A., Vaillancourt, J. P., Ding, C. K., Gallant, M., Gareau, Y., Griffin, P. R., Labelle, M., Lazebnik, Y. A., Munday, N. A., Raju, S. M., Smulson, M. E., Yamin, T., Yu, V. L., and Miller, D. K (1995). Identification and inhibition of the ICE/CED-3 protease necessary for mammalian apoptosis. Nature 376, 3743.

Nicholson, D. W. and Thornberry, N. A. (1997). Caspases: Killer proteases. TIBS 22, 299–306.

Odake, S., Kam, C. M., Narasimhan, L., Poe, M., Blake, J. T., Krahenbuhl, O., Tschopp, J., and Powers, J. C. (1991). Human and murine cytotoxic T lymphocyte serine proteases: Subsite mapping with peptide thioester substrates and inhibition of enzyme activity and cytolysis by isocoumarins. Biochemistry 30, 2217–2227.

Pinkoski, M. J., Winkler, U., Hudig, D., and Bleackley, R. C. (1996). Binding of granzyme B in the nucelus of target cells. Recognition of an 80 kDa protein. J.Biol.Chem. 271, 10225–10229.

Podack, E. and Konigsberg, P. J. (1984). Cytolytic T cell granules. Isolation, structural, biochemical and functional characterization. J.Exp.Med. 160, 695–710.

Poe, M., Blake, J. T., Boulton, D. A., Gammon, M., Sigal, N. H., Wu, J. K., and Zweerink, H. J. (1991). Human cytotoxic lymphocyte granzyme B: Its purification from granules and the characterization of substrate and inhibitor specificity. J.Biol.Chem. 266, 98–103.

Quan, L. T., Tewari, M., O'Rourke, K., Dixit, V., Snipas, S. J., Poirier, G. G., Ray, C., Pickup, D. J., and Salveson, G. S. (1996). Proteolytic activation of the cell death protease Yama/CPP32 by granzyme B. Proc.Natl.Acad.Sci.USA. 93, 1972–1976.

Radic, M. Z. and M. Weigert. (1994). Genetic and structural evidence for antigen selection of anti-DNA antibodies. Ann.Rev.Immunol. 12:487–520.

Ramage, P., Cheneval, D., Chvei, M., Graff, P., Hemmig, R., Heng, R., Kocher, H. P., Mackenzie, A., Memmert, K., Revesz, L., and Wishart, W. (1995). Expression, refolding, and autocatalytic proteolytic processing of the interleukin-1b-converting enzyme precursor. J.Biol.Chem. 270, 9378–9383.

Salemi, S., A. P. Caporossi, L. Boffa, M. G. Longobardi, and V. Barnaba. (1995). HIVgp120 activates autoreactive CD4-specific T cell responses by unveiling of hidden CD4 peptides during processing. J.Exp.Med. 181:2253–2257.

Sarin, A., Williams, M. S., Alexander-Miller, M. A., Berzofsky, J. A., Zacharchuk, C. M., and Henkart, P. A. (1997). Target cell lysis by CTL granule exocytosis is independent of ICE/Ced-3 family proteases. Immunity 6:209–215.

Sercarz, E. E., P. V. Lehmann, A. Ametani, G. Benichou, A. Miller, and K. Moudgil. (1993). Dominance and crypticity of T cell antigenic determinants. Ann.Rev.Immunol. 11:729–766.

Sercarz, E. E. and S. K Datta. (1994). Mechanisms of autoimmunization: perspective from the mid-90s. Curr.Opin.Immunol. 6:875–881.

Shi, L. F., Mai, S., Israel, S., Browne, K., Trapani, J. A., and Greenberg, A. H. (1997). Granzyme B (GraB) autonomously crosses the cell membrane and perforin initiates apoptosis and GraB nuclear localization. J.Exp.Med. 185, 855–866.

Shresta, S., MacIvor, D. M., Heusel, J. W., Russell, J. H., and Ley, T. J. (1995). Natural killer and lymphokine-activated killer cells require granzyme B for the rapid induction of apoptosis in susceptible target cells. Proc.Natl.Acad.Sci.USA 92, 5679–5683.

Simitsek, P. D., D. G. Campbell, A. Lanzavecchia, N. Fairweather, and C. Watts. (1995). Modulation of antigen processing by bound antibodies can boost or suppress class II major histocompatibility complex presentation of different T cell determinants. J.Exp.Med. 181:1957–1963.

Song, Q. Z., Burrows, S. R., Smith, G., Lees-Miller, S. P., Kumar, S., Chan, D. W., Trapani, J. A., Alnemri, E., Litwack, G., Lu, H., Moss, D. J., Jackson, S., and Lavin, M. F. (1996a). Interleukin-1b-converting enzyme-like protease cleaves DNA- dependent protein kinase in cytotoxic T cell killing. J.Exp.Med. 184, 619–626.

Song, Q. Z., Lees-Miller, S. P., Kumar, S., Zhang, N., Chan, D. W., Smith, G. C. M., Jackson, S. P., Alnemri, E. S., Litwack, G., Khanna, K. K., and Lavin, M. F. (1996b). DNA-dependent protein kinase catalytic subunit: A target for an ICE-like protease in apoptosis. EMBO J. 15, 3238–3246.

Srinivasula, S. M., Fernandes-Alnemri, T., Zangrilli, J., Robertson, N., Armstrong, R. C., Wang, L. J., Trapani, J. A., Tomaselli, K. J., Litwack, G., and Alnemri, E. S. (1996). The Ced-3/interleukin 1b converting enzyme-like homolog Mch6 and the lamin-cleaving enzyme Mch2a are substrates for the apoptotic mediator CPP32. J.Biol.Chem. 271, 27099–27106.

Srinivasula, S. M., Ahmad, M., Ottilie, S., Bullrich, F., Banks, S., Wang, Y., Fernandes-Alnemri, T., Croce, C. M., Litwack, G., Tomaseli, K. J., Armstrong, R. C and Alnemri, E. S. (1997). FLAME-1, a novel FADD-like anti-apoptotic molecule that regulates Fas/TNFR1-induced apoptosis. J.Biol.Chem. 272,18542–18545.

Talanian, R. V., Yang, X., Turbov, J., Seth, P., Ghayur, T., Casiano, C. A., Orth, K., and Froelich, C. J. (1997). Granule-mediated killing: Pathways for granzyme B-initiated apoptosis. J.Exp.Med. 186, 1323–1331.

Thome, M., Schneider, P., Hofmann, K., Fickenscher, H., Meinl, E., Neipel, F., Mattmann, C., Burns, K, Bodmer, J. L., Schröter, M., Scaffidi, C., Krammer, P. H., Peter, M. E., and Tschopp, J. (1997). Viral FLICE-inhibitory proteins (FLIPs) prevent apoptosis induced by death receptors. Nature 386, 517–521.

Thompson, C. B. (1995). Apoptosis in the pathogenesis and treatment of disease. Science 267, 1456–1462.

Thornberry, N. A. and Molineaux, S. M. (1995). Interleukin-1 β converting enzyme: a novel cysteine protease required for IL-1 β production and implicated in programmed cell death. Protein Science 4, 3–12.

Thornberry, N. A., Ranon, T. A., Pieterson, E. P., Rasper, D. M., Timkey, T., Garcia-Calvo, M., Houtzager, V. M., Nordstrom, P. A., Roy, S., Vaillancourt, J. P., Chapman, K. T., and Nicholson, D. W. (1997). A combinatorial approach defines specificities of members of the caspase family and granzyme B—Functional, relationships established for key mediators of apoptosis. J.Biol.Chem272, 17907–17911.

Topalian, S. L., Solomon, D. and Rosenberg, S. A. (1989). Tumor-specific cytolysis by lymphocytes infiltrating human melanomas. J. Immunol. 142, 3714–3725.

Trapani, J. A., Browne, K. A., Smyth, M. J., and Jans, D. A. (1996). Localization of granzyme B in the nucleus—A putative role in the mechanism of cytotoxic lymphocyte-mediated apoptosis. J.Biol.Chem. 271, 4127–4133.

Tschopp, J. (1994). Granzyme B. Methods Enzymol. 244, 80–87.

Wang, S. Y., Miura, M., Jung, Y. K., Zhu, H., Gagliardini, V., Shi, L. F., Greenberg, A. H., and Yuan, J. Y. (1996). Identification and characterization of Ich-3, a member of the interleukin-1b converting enzyme (ICE)/Ced-3 family and an upstream regulator of ICE. J.Biol.Chem. 271, 20580–20587.

Watts, C. and A. Lanzavecchia. (1993). Suppressive effect of an antibody on processing of T cell epitopes. *J.Exp.Med.* 178:1459–1463.

White, E. (1996). Life, death, and the pursuit of apoptosis. Genes Dev. 10, 1–15.

Xue, D. and Horvitz, H. R. (1995). Inhibition of the *Caenorhabditis elegans* cell-death protease CED-3 by a CED-3 cleavage site in baculovirus p35 protein. Nature 377, 248–251.

Yamin, T. T., Ayala, J. M., and Miller, D. K (1996). Activation of the native 45-kDa precursor form of interleukin-1β-converting enzyme. J.Biol.Chem. 271, 13273–13282.

Young J. D.-E., Hengartner, H., Podack, E., and Cohn, Z. A. (1986). Purification and characterization of a cytolytic pore-forming protein from granules of cloned lymphocytes with natural killer activity. Cell 44, 849–859.

TABLE I

Comparison of $k_{cat}/K_m$ (catalytic constant) values for the cleavage of different substrates by granzyme B and caspase-3.
The data obtained in time-course experiments were densitometrically scanned and used to calculate the % cleavage of each substrate. These values were fitted to the first order rate equation [% substrate cleaved = $100*(1 - e_{-((kat*[E]/Km)*(time))})$] to calculate $K_{cat}/K_m$. Measurements for each protease-substrate combination were performed at 3 different protease concentrations, enabling experimental variations in $k_{cat}/K_m$ to be assessed.

| | | $k_{cat}/K_m$ (M$^{-1}$s$^{-1}$) | |
|---|---|---|---|
| Substrate | Method of Detection | Cleavage by granzyme B | Cleavage by caspase-3 |
| DNA-PK$_{CS}$ | Immunoblotting | $2.5 \pm 0.8 \times 10^6$ | $7.5 \pm 0.8 \times 10^6$ |
| NuMA | Fluorography | $5.4 \pm 1.5 \times 10^5$ | $5.0 \pm 1.0 \times 10^5$ |
| Caspase-7[1] | Fluorography | $1.8 \pm 0.6 \times 10^5$ | — |
| Caspase-7[1] | Immunoblotting | $1.9 \pm 0.6 \times 10^5$ | — |
| Caspase-3 | Fluorography | $3.6 \pm 1.0 \times 10^4$ | — |
| Caspase-3 | Immunoblotting | $2.3 \pm 0.4 \times 10^4$ | — |
| PARP | Fluorography | $2.3 \pm 1.8 \times 10^4$ | $5.0 \pm 0.2 \times 10^6$ |

[1]The source of caspase 3 and 7 precursors used in immunoblotting was THP$^{-1}$ cytosol. Blotting antibodies were specific for either caspase 3 or 7, respectively.

TABLE II

Different fragments are detected after in vitro cleavage of autoantigens with granzyme B versus caspase-3.
The data obtained in FIG. 2, using purified DNA-PK$_{CS}$, [$^{35}$S]methionine labeled PARP, endogenous DNA-PK$_{CS}$ and NuMA, and purified proteases, were used for the tabulation below.

| | Fragmented induced after cleavage with | | Likely granzyme B | Of SEQ |
|---|---|---|---|---|
| Substrate | Granzyme B | Caspase-3 | Cleavage sites | ID No. |
| DNA-PK$_{CS}$[2] | 100 kDa | 150 kDa | VDQD$^{3210}$-G$^{3211}$ | 29 |
| DNA-PK$_{CS}$[3] | 250 kDa | 250 kDa | VGPD$^{2698}$-F$^{2699}$; | 24 |
| | | | DEVD$^{2712}$-N$^{2713}$ | 25 |
| NuMA | 175 kDa | 185 kDa | VLGD$^{411}$-V$^{412}$ | 30 |
| PARP | 62 kDa | 89 kDa | VGPD$^{537}$-S$^{538}$ | 27 |
| | | | (Froelich et al., 1996a) | |

[2]DNA-PK$_{CS}$ fragments were detected by immunoblotting with monoclonal antibody 25-4 or patient sera A.G. and G.A. (which all recognize the C-terminuis).

[3]DNA-PK$_{CS}$ fragments were detected by monoclonal antibody 18-2 (which recognizes the N-terminus).

TABLE III

AUTOANTIGENS ARE EFFICIENTLY CLEAVED BY GRANZYME

| SEQ ID NO | Autoantigen | Cleavage Site | $k_{cat}/K_m$ (M$^{-1.s-1}$) | Fragments (kDa) |
|---|---|---|---|---|
| 24 | DNA-PK$_{CS}$ | VGPD$^{2698}$-F | $2.5 \pm 0.8 \times 10^6$ | 160, 100 |
| 2 | Topoisomerase I | I EDA$^{15}$-f | $1.6 \pm 0.6 \times 10^6$ | 97, 72 |
| 3 | NuMA | VATD$^{1705}$-A | $5.4 \pm 1.4 \times 10^5$ | 175 |
| 4 | Mi-2 | V DPD$^{1312}$-Y | $8.5 \pm 1.9 \times 10^4$ | 75, 72, 48 |
| 5 | La | LEED$^{220}$-A | $6.1 \pm 1.7 \times 10^4$ | 21, 28 |
| 6 | PMS1 | LTPD$^{313}$-K | $6.9 \pm 0.9 \times 10^4$ | 48 |
| 37 | | ISA D$^{496}$-E | | |
| 7 | Fibrilliarin | VGPD$^{184}$-G | $3.3 \pm 1.9 \times 10^4$ | 20, 17 |
| 8 | PARP | VDPD$^{536}$-S | $2.3 \pm 1.8 \times 10^4$ | 72, 62, 55 |
| 9 | U1-70 kDa | LGND$^{409}$-S | $1.3 \pm 0.4 \times 10^4$ | 60 |
| 10 | PMS2 | VEKD$^{493}$-S | $1.4 \pm 0.6 \times 10^4$ | 60, 45, 35 |
| 11 | Isoleucyl tRNA synthetase (O.J.) | VTPD982-Q | $7.8 \pm 1.8 \times 10^4$ | |
| 12 | Histidyl tRNA synthetase (Jo-1) | LGPD$^{48}$-E | $2.3 \pm 0.7 \times 10^4$ | 40 |
| 13 | Alanyl tRNA synthetase (PL-12) | VAPD$^{632}$-R | $1.8 \times 10^4$ | 63, 40 |
| 14 | RNA polymerase I | ICPD$^{448}$-M | $1.3 \pm 0.5 \times 10^4$ | 140 |
| 15 | KI-67 | VCTD$^{1481}$-K | $8.1 \pm 2.6 \times 10^3$ | 168, 148 |
| 16 | PmScl | VEQD$^{252}$-M | $7.5 \pm 1.4 \times 10^3$ | 85, 74, 60 |
| 17 | CENP B | VDSD$^{457}$-E | $5.9 \pm 0.2 \times 10^3$ | 58, 40 |
| 18 | RNA polymerase II | I TPD$^{370}$-P | ND | 200 |
| 19 | SRP 72 | VTPD$^{573}$-P | ND | 62 |
| 20 | Ku 70 | I SSD$^{79}$-R | ND | 65 |
| 21 | Tyrosinase | ICTD$^{249}$ | | |
| 22 | E4 | VDVD$^{123}$ | | |
| 23 | Golgin 160 | SEVD$^{311}$ | | |
| 36 | Golgin 160 | VGPD$^{92}$ | | |
| 2 | Golgin 160 | IEAD$^{648}$ | | |
| | Myosin | | | |

What is claimed:

1. A method of making at least one human autoantigenic fragment from at least one human autoantigen selected from the group consisting of human DNA-$PK_{CS}$ and human NuMA, comprising the steps of
   (a) isolating cells containing at least one human autoantigen, and
   (b) contacting the cells with a lymphocyte granule enzyme to produce a mixture containing at least one human autoantigen fragment.

2. The method of claim 1 further comprising the step of (c) isolating said at least one human autoantigenic fragment.

3. The method of claim 1 wherein step (a) further comprises purifying at least one human autoantigen from the cells and step (b) comprises contacting said purified human autoantigen with granzyme B.

4. The method of claim 1 wherein said lymphocyte granule enzyme is isolated from the granules of at least one lymphocyte selected from the group consisting of cytotoxic T lymphocytes (CTL), natural killer cells (NK), lymphokine activated killer cells (LAK) and cells of the YT cell line.

5. The method of claim 1 wherein step (b) further comprises contacting the cells with a caspase inhibitor.

* * * * *

SEQUENCE LISTING

<160> NUMBER OF SEQ ID NOS: 37

<210> SEQ ID NO 1
<211> LENGTH: 4
<212> TYPE: PRT
<213> ORGANISM: Human

<400> SEQUENCE: 1

Asp Glu Val Asp
 1

<210> SEQ ID NO 2
<211> LENGTH: 4
<212> TYPE: PRT
<213> ORGANISM: Human

<400> SEQUENCE: 2

Ile Glu Ala Asp
 1

<210> SEQ ID NO 3
<211> LENGTH: 5
<212> TYPE: PRT
<213> ORGANISM: Human

<400> SEQUENCE: 3

Val Ala Thr Asp Ala
 1               5

<210> SEQ ID NO 4
<211> LENGTH: 5
<212> TYPE: PRT
<213> ORGANISM: Human

<400> SEQUENCE: 4

Val Asp Pro Asp Tyr
 1               5

<210> SEQ ID NO 5
<211> LENGTH: 5
<212> TYPE: PRT
<213> ORGANISM: Human

<400> SEQUENCE: 5

Leu Glu Glu Asp Ala
 1               5

<210> SEQ ID NO 6
<211> LENGTH: 5
<212> TYPE: PRT
<213> ORGANISM: Human

<400> SEQUENCE: 6

Leu Thr Pro Asp Lys
 1               5

<210> SEQ ID NO 7
<211> LENGTH: 5
<212> TYPE: PRT
<213> ORGANISM: Human

<400> SEQUENCE: 7

Val Gly Pro Asp Gly

```
                 1               5

<210> SEQ ID NO 8
<211> LENGTH: 5
<212> TYPE: PRT
<213> ORGANISM: Human

<400> SEQUENCE: 8

Val Asp Pro Asp Ser
 1               5

<210> SEQ ID NO 9
<211> LENGTH: 5
<212> TYPE: PRT
<213> ORGANISM: Human

<400> SEQUENCE: 9

Leu Gly Asn Asp Ser
 1               5

<210> SEQ ID NO 10
<211> LENGTH: 5
<212> TYPE: PRT
<213> ORGANISM: Human

<400> SEQUENCE: 10

Val Glu Lys Asp Ser
 1               5

<210> SEQ ID NO 11
<211> LENGTH: 5
<212> TYPE: PRT
<213> ORGANISM: Human

<400> SEQUENCE: 11

Val Thr Pro Asp Gln
 1               5

<210> SEQ ID NO 12
<211> LENGTH: 5
<212> TYPE: PRT
<213> ORGANISM: Human

<400> SEQUENCE: 12

Leu Gly Pro Asp Glu
 1               5

<210> SEQ ID NO 13
<211> LENGTH: 5
<212> TYPE: PRT
<213> ORGANISM: Human

<400> SEQUENCE: 13

Val Ala Pro Asp Arg
 1               5

<210> SEQ ID NO 14
<211> LENGTH: 5
<212> TYPE: PRT
<213> ORGANISM: Human

<400> SEQUENCE: 14

Ile Cys Pro Asp Met
 1               5
```

```
<210> SEQ ID NO 15
<211> LENGTH: 5
<212> TYPE: PRT
<213> ORGANISM: Human

<400> SEQUENCE: 15

Val Cys Thr Asp Lys
1               5

<210> SEQ ID NO 16
<211> LENGTH: 5
<212> TYPE: PRT
<213> ORGANISM: Human

<400> SEQUENCE: 16

Val Glu Gln Asp Met
1               5

<210> SEQ ID NO 17
<211> LENGTH: 5
<212> TYPE: PRT
<213> ORGANISM: Human

<400> SEQUENCE: 17

Val Asp Ser Asp Glu
1               5

<210> SEQ ID NO 18
<211> LENGTH: 5
<212> TYPE: PRT
<213> ORGANISM: Human

<400> SEQUENCE: 18

Ile Thr Pro Asp Pro
1               5

<210> SEQ ID NO 19
<211> LENGTH: 5
<212> TYPE: PRT
<213> ORGANISM: Human

<400> SEQUENCE: 19

Val Thr Pro Asp Pro
1               5

<210> SEQ ID NO 20
<211> LENGTH: 5
<212> TYPE: PRT
<213> ORGANISM: Human

<400> SEQUENCE: 20

Ile Ser Ser Asp Arg
1               5

<210> SEQ ID NO 21
<211> LENGTH: 4
<212> TYPE: PRT
<213> ORGANISM: Human

<400> SEQUENCE: 21

Ile Cys Thr Asp
1

<210> SEQ ID NO 22
```

```
<211> LENGTH: 4
<212> TYPE: PRT
<213> ORGANISM: Human

<400> SEQUENCE: 22

Val Asp Val Asp
 1

<210> SEQ ID NO 23
<211> LENGTH: 4
<212> TYPE: PRT
<213> ORGANISM: Human

<400> SEQUENCE: 23

Ser Glu Val Asp
 1

<210> SEQ ID NO 24
<211> LENGTH: 5
<212> TYPE: PRT
<213> ORGANISM: Human

<400> SEQUENCE: 24

Val Gly Pro Asp Phe
 1               5

<210> SEQ ID NO 25
<211> LENGTH: 5
<212> TYPE: PRT
<213> ORGANISM: Human

<400> SEQUENCE: 25

Asp Glu Val Asp Asn
 1               5

<210> SEQ ID NO 26
<211> LENGTH: 4
<212> TYPE: PRT
<213> ORGANISM: Human

<400> SEQUENCE: 26

Tyr Val Ala Asp
 1

<210> SEQ ID NO 27
<211> LENGTH: 5
<212> TYPE: PRT
<213> ORGANISM: Human

<400> SEQUENCE: 27

Val Gly Pro Asp Ser
 1               5

<210> SEQ ID NO 28
<211> LENGTH: 4
<212> TYPE: PRT
<213> ORGANISM: Human

<400> SEQUENCE: 28

Ile Glu Thr Asp
 1

<210> SEQ ID NO 29
<211> LENGTH: 5
<212> TYPE: PRT
```

```
<213> ORGANISM: Human

<400> SEQUENCE: 29

Val Asp Gln Asp Gly
 1               5

<210> SEQ ID NO 30
<211> LENGTH: 5
<212> TYPE: PRT
<213> ORGANISM: Human

<400> SEQUENCE: 30

Val Leu Gly Asp Val
 1               5

<210> SEQ ID NO 31
<211> LENGTH: 5
<212> TYPE: PRT
<213> ORGANISM: Human

<400> SEQUENCE: 31

Asp Trp Val Asp Gly
 1               5

<210> SEQ ID NO 32
<211> LENGTH: 2101
<212> TYPE: PRT
<213> ORGANISM: Human

<400> SEQUENCE: 32

Met Thr Leu His Ala Thr Arg Gly Ala Ala Leu Leu Ser Trp Val Asn
 1               5                  10                  15

Ser Leu His Val Ala Asp Pro Val Glu Ala Val Leu Gln Leu Gln Asp
                20                  25                  30

Cys Ser Ile Phe Ile Lys Ile Ile Asp Arg Ile His Gly Thr Glu Glu
            35                  40                  45

Gly Gln Gln Ile Leu Lys Gln Pro Val Ser Glu Arg Leu Asp Phe Val
        50                  55                  60

Cys Ser Phe Leu Gln Lys Asn Arg Lys His Pro Ser Ser Pro Glu Cys
 65                  70                  75                  80

Leu Val Ser Ala Gln Lys Val Leu Glu Gly Ser Glu Leu Glu Leu Ala
                85                  90                  95

Lys Met Thr Met Leu Leu Leu Tyr His Ser Thr Met Ser Ser Lys Ser
                100                 105                 110

Pro Arg Asp Trp Glu Gln Phe Glu Tyr Lys Ile Gln Ala Glu Leu Ala
            115                 120                 125

Val Ile Leu Lys Phe Val Leu Asp His Glu Asp Gly Leu Asn Leu Asn
        130                 135                 140

Glu Asp Leu Glu Asn Phe Leu Gln Lys Ala Pro Val Pro Ser Thr Cys
145                 150                 155                 160

Ser Ser Thr Phe Pro Glu Glu Leu Ser Pro Pro Ser His Gln Ala Lys
                165                 170                 175

Arg Glu Ile Arg Phe Leu Glu Leu Gln Lys Val Ala Ser Ser Ser Ser
            180                 185                 190

Gly Asn Asn Phe Leu Ser Ser Pro Ala Ser Pro Met Gly Asp Ile
        195                 200                 205

Leu Gln Thr Pro Gln Phe Gln Met Arg Arg Leu Lys Lys Gln Leu Ala
        210                 215                 220
```

-continued

```
Asp Glu Arg Ser Asn Arg Asp Glu Leu Glu Leu Glu Leu Ala Glu Asn
225                 230                 235                 240
Arg Lys Leu Leu Thr Glu Lys Asp Ala Gln Ile Ala Met Met Gln Gln
            245                 250                 255
Arg Ile Asp Arg Leu Ala Leu Leu Asn Glu Lys Gln Ala Ala Ser Pro
        260                 265                 270
Leu Glu Pro Lys Glu Leu Glu Glu Leu Arg Asp Lys Asn Glu Ser Leu
    275                 280                 285
Thr Met Arg Leu His Glu Thr Leu Lys Gln Cys Gln Asp Leu Lys Thr
290                 295                 300
Glu Lys Ser Gln Met Asp Arg Lys Ile Asn Gln Leu Ser Glu Glu Asn
305                 310                 315                 320
Gly Asp Leu Ser Phe Lys Leu Arg Glu Phe Ala Ser His Leu Gln Gln
            325                 330                 335
Leu Gln Asp Ala Leu Asn Glu Leu Thr Glu Glu His Ser Lys Ala Thr
        340                 345                 350
Gln Glu Trp Leu Glu Lys Gln Ala Gln Leu Glu Lys Glu Leu Ser Ala
    355                 360                 365
Ala Leu Gln Asp Lys Lys Cys Leu Glu Glu Lys Asn Glu Ile Leu Gln
370                 375                 380
Gly Lys Leu Ser Gln Leu Glu Glu His Leu Ser Gln Leu Gln Asp Asn
385                 390                 395                 400
Pro Pro Gln Glu Lys Gly Glu Val Leu Gly Asp Val Leu Gln Leu Glu
            405                 410                 415
Thr Leu Lys Gln Glu Ala Ala Thr Leu Ala Ala Asn Asn Thr Gln Leu
        420                 425                 430
Gln Ala Arg Val Glu Met Leu Glu Thr Glu Arg Gly Gln Gln Glu Ala
    435                 440                 445
Lys Leu Leu Ala Glu Arg Gly His Phe Glu Glu Lys Gln Gln Leu
450                 455                 460
Ser Ser Leu Ile Thr Asp Leu Gln Ser Ser Ile Ser Asn Leu Ser Gln
465                 470                 475                 480
Ala Lys Glu Glu Leu Glu Gln Ala Ser Gln Ala His Gly Ala Arg Leu
            485                 490                 495
Thr Ala Gln Val Ala Ser Leu Thr Ser Glu Leu Thr Thr Leu Asn Ala
        500                 505                 510
Thr Ile Gln Gln Gln Asp Gln Glu Leu Ala Gly Leu Lys Gln Gln Ala
    515                 520                 525
Lys Glu Lys Gln Ala Gln Leu Ala Gln Thr Leu Gln Gln Gln Glu Gln
530                 535                 540
Ala Ser Gln Gly Leu Arg His Gln Val Glu Gln Leu Ser Ser Ser Leu
545                 550                 555                 560
Lys Gln Lys Glu Gln Gln Leu Lys Glu Val Ala Glu Lys Gln Glu Ala
            565                 570                 575
Thr Arg Gln Asp His Ala Gln Gln Leu Ala Thr Ala Ala Glu Glu Arg
        580                 585                 590
Glu Ala Ser Leu Arg Glu Arg Asp Ala Ala Leu Lys Gln Leu Glu Ala
    595                 600                 605
Leu Glu Lys Glu Lys Ala Ala Lys Leu Glu Ile Leu Gln Gln Gln Leu
610                 615                 620
Gln Val Ala Asn Glu Ala Arg Asp Ser Ala Gln Thr Ser Val Thr Gln
625                 630                 635                 640
Ala Gln Arg Glu Lys Ala Glu Leu Ser Arg Lys Val Glu Glu Leu Gln
```

-continued

```
                645                 650                 655
Ala Cys Val Glu Thr Ala Arg Gln Glu Gln His Glu Ala Gln Ala Gln
                660                 665                 670
Val Ala Glu Leu Glu Leu Gln Leu Arg Ser Glu Gln Gln Lys Ala Thr
                675                 680                 685
Glu Lys Glu Arg Val Ala Gln Glu Lys Asp Gln Leu Gln Glu Gln Leu
                690                 695                 700
Gln Ala Leu Lys Glu Ser Leu Lys Val Thr Lys Gly Ser Leu Glu Glu
705                 710                 715                 720
Glu Lys Arg Arg Ala Ala Asp Ala Leu Glu Glu Gln Gln Arg Cys Ile
                725                 730                 735
Ser Glu Leu Lys Ala Glu Thr Arg Ser Leu Val Glu Gln His Lys Arg
                740                 745                 750
Glu Arg Lys Glu Leu Glu Glu Arg Ala Gly Arg Lys Gly Leu Glu
                755                 760                 765
Ala Arg Leu Leu Gln Leu Gly Glu Ala His Gln Ala Glu Thr Glu Val
                770                 775                 780
Leu Arg Arg Glu Leu Ala Glu Ala Met Ala Ala Gln His Thr Ala Glu
785                 790                 795                 800
Ser Glu Cys Glu Gln Leu Val Lys Glu Val Ala Ala Trp Arg Asp Gly
                805                 810                 815
Tyr Glu Asp Ser Gln Gln Glu Ala Gln Tyr Gly Ala Met Phe Gln
                820                 825                 830
Glu Gln Leu Met Thr Leu Lys Glu Glu Cys Glu Lys Ala Arg Gln Glu
                835                 840                 845
Leu Gln Glu Ala Lys Glu Lys Val Ala Gly Ile Glu Ser His Ser Glu
                850                 855                 860
Leu Gln Ile Ser Arg Gln Gln Asn Lys Leu Ala Glu Leu His Ala Asn
865                 870                 875                 880
Leu Ala Arg Ala Leu Gln Val Gln Glu Lys Glu Val Arg Ala Gln
                885                 890                 895
Lys Leu Ala Asp Asp Leu Ser Thr Leu Gln Glu Lys Met Ala Ala Thr
                900                 905                 910
Ser Lys Glu Val Ala Arg Leu Glu Thr Leu Val Arg Lys Ala Gly Glu
                915                 920                 925
Gln Gln Glu Thr Ala Ser Arg Glu Leu Val Lys Glu Pro Ala Arg Ala
                930                 935                 940
Gly Asp Arg Gln Pro Glu Trp Leu Glu Glu Gln Gln Gly Arg Gln Phe
945                 950                 955                 960
Cys Ser Thr Gln Ala Ala Leu Gln Ala Met Glu Arg Glu Ala Glu Gln
                965                 970                 975
Met Gly Asn Glu Leu Glu Arg Leu Arg Ala Ala Leu Met Glu Ser Gln
                980                 985                 990
Gly Gln Gln Gln Glu Glu Arg Gly Gln Gln Glu Arg Glu Val Ala Arg
                995                 1000                1005
Leu Thr Gln Glu Arg Gly Arg Ala Gln Ala Asp Leu Ala Leu Glu Lys
                1010                1015                1020
Ala Ala Arg Ala Glu Leu Glu Met Arg Leu Gln Asn Ala Leu Asn Glu
1025                1030                1035                1040
Gln Arg Val Glu Phe Ala Thr Leu Gln Glu Ala Leu Ala His Ala Leu
                1045                1050                1055
Thr Glu Lys Glu Gly Lys Asp Gln Glu Leu Ala Lys Leu Arg Gly Leu
                1060                1065                1070
```

-continued

```
Glu Ala Ala Gln Ile Lys Glu Leu Glu Leu Arg Gln Thr Val Lys
        1075                1080                1085
Gln Leu Lys Glu Gln Leu Ala Lys Lys Glu Lys Glu His Ala Ser Gly
    1090                1095                1100
Ser Gly Ala Gln Ser Glu Ala Ala Gly Arg Thr Glu Pro Thr Gly Pro
1105                1110                1115                1120
Lys Leu Glu Ala Leu Arg Ala Glu Val Ser Lys Leu Glu Gln Gln Cys
            1125                1130                1135
Gln Lys Gln Gln Glu Gln Ala Asp Ser Leu Glu Arg Ser Leu Glu Ala
        1140                1145                1150
Glu Arg Ala Ser Arg Ala Glu Arg Asp Ser Ala Leu Glu Thr Leu Gln
        1155                1160                1165
Gly Gln Leu Glu Glu Lys Ala Gln Glu Leu Gly His Ser Gln Ser Ala
    1170                1175                1180
Leu Ala Ser Ala Gln Arg Glu Leu Ala Ala Phe Arg Thr Lys Val Gln
1185                1190                1195                1200
Asp His Ser Lys Ala Glu Asp Glu Trp Lys Ala Gln Val Ala Arg Gly
            1205                1210                1215
Arg Gln Glu Ala Glu Arg Lys Asn Ser Leu Ile Ser Ser Leu Glu Glu
        1220                1225                1230
Glu Val Ser Ile Leu Asn Arg Gln Val Leu Glu Lys Glu Gly Glu Ser
        1235                1240                1245
Lys Glu Leu Lys Arg Leu Val Met Ala Glu Ser Glu Lys Ser Gln Lys
    1250                1255                1260
Leu Glu Glu Ser Cys Ala Cys Cys Arg Gln Arg Gln Pro Ala Thr Val
1265                1270                1275                1280
Pro Glu Leu Gln Asn Ala Ala Leu Leu Cys Gly Arg Arg Cys Arg Ala
            1285                1290                1295
Ser Gly Arg Glu Ala Glu Lys Gln Arg Val Ala Ser Glu Asn Leu Arg
        1300                1305                1310
Gln Glu Leu Thr Ser Gln Ala Glu Arg Ala Glu Glu Leu Gly Gln Glu
        1315                1320                1325
Leu Lys Ala Trp Gln Glu Lys Phe Phe Gln Lys Glu Gln Ala Leu Ser
    1330                1335                1340
Thr Leu Gln Leu Glu His Thr Ser Thr Gln Ala Leu Val Ser Glu Leu
1345                1350                1355                1360
Leu Pro Ala Lys His Leu Cys Gln Gln Leu Gln Ala Glu Gln Ala Ala
            1365                1370                1375
Ala Glu Lys Arg His Arg Glu Glu Leu Glu Gln Ser Lys Gln Ala Ala
        1380                1385                1390
Gly Gly Leu Arg Ala Glu Leu Leu Arg Ala Gln Arg Glu Leu Gly Glu
    1395                1400                1405
Leu Ile Pro Leu Arg Gln Lys Val Ala Glu Gln Glu Arg Thr Ala Gln
        1410                1415                1420
Gln Leu Arg Ala Glu Lys Ala Ser Tyr Ala Glu Gln Leu Ser Met Leu
1425                1430                1435                1440
Lys Lys Ala His Gly Leu Leu Ala Glu Glu Asn Arg Gly Leu Gly Glu
            1445                1450                1455
Arg Ala Asn Leu Gly Arg Gln Phe Leu Glu Val Glu Leu Asp Gln Ala
        1460                1465                1470
Arg Glu Lys Tyr Val Gln Glu Leu Ala Ala Val Arg Ala Asp Ala Glu
    1475                1480                1485
```

```
Thr Arg Leu Ala Glu Val Gln Arg Glu Ala Gln Ser Thr Ala Arg Glu
    1490                1495                1500
Leu Glu Val Met Thr Ala Lys Tyr Glu Gly Ala Lys Val Lys Val Leu
1505                1510                1515                1520
Glu Glu Arg Gln Arg Phe Gln Glu Arg Gln Lys Leu Thr Ala Gln
            1525                1530                1535
Val Glu Glu Leu Ser Lys Lys Leu Ala Asp Ser Asp Gln Ala Ser Lys
            1540                1545                1550
Val Gln Gln Gln Lys Leu Lys Ala Val Gln Ala Gln Gly Gly Glu Ser
        1555                1560                1565
Gln Gln Glu Ala Gln Arg Phe Gln Ala Gln Leu Asn Glu Leu Gln Ala
    1570                1575                1580
Gln Leu Ser Gln Lys Glu Gln Ala Ala Glu His Tyr Lys Leu Gln Met
1585                1590                1595                1600
Glu Lys Ala Lys Thr His Tyr Asp Ala Lys Lys Gln Gln Asn Gln Glu
            1605                1610                1615
Leu Gln Glu Gln Leu Arg Ser Leu Glu Gln Leu Gln Lys Glu Asn Lys
        1620                1625                1630
Glu Leu Arg Ala Glu Ala Glu Arg Leu Gly His Glu Leu Gln Gln Ala
    1635                1640                1645
Gly Leu Lys Thr Lys Glu Ala Glu Gln Thr Cys Arg His Leu Thr Ala
1650                1655                1660
Gln Val Arg Ser Leu Glu Ala Gln Val Ala His Ala Asp Gln Gln Leu
1665                1670                1675                1680
Arg Asp Leu Gly Lys Phe Gln Val Ala Thr Asp Ala Leu Lys Ser Arg
            1685                1690                1695
Glu Pro Gln Ala Lys Pro Gln Leu Asp Leu Ser Ile Asp Ser Leu Asp
        1700                1705                1710
Leu Ser Cys Glu Glu Gly Thr Pro Leu Ser Ile Thr Ser Lys Leu Pro
    1715                1720                1725
Arg Thr Gln Pro Asp Gly Thr Ser Val Pro Gly Glu Pro Ala Ser Pro
1730                1735                1740
Ile Ser Gln Arg Leu Pro Pro Lys Val Glu Ser Leu Glu Ser Leu Tyr
1745                1750                1755                1760
Phe Thr Pro Ile Pro Ala Arg Ser Gln Ala Pro Leu Glu Ser Ser Leu
            1765                1770                1775
Asp Ser Leu Gly Asp Val Phe Leu Asp Ser Gly Arg Lys Thr Arg Ser
        1780                1785                1790
Ala Arg Arg Arg Thr Thr Gln Ile Ile Asn Ile Thr Met Thr Lys Lys
    1795                1800                1805
Leu Asp Val Glu Glu Pro Asp Ser Ala Asn Ser Ser Phe Tyr Ser Thr
1810                1815                1820
Arg Ser Ala Pro Ala Ser Gln Ala Ser Leu Arg Ala Thr Ser Ser Thr
1825                1830                1835                1840
Gln Ser Leu Ala Arg Leu Gly Ser Pro Asp Tyr Gly Asn Ser Ala Leu
            1845                1850                1855
Leu Ser Leu Pro Gly Tyr Arg Pro Thr Thr Arg Ser Ser Ala Arg Arg
        1860                1865                1870
Ser Gln Ala Gly Val Ser Ser Gly Ala Pro Pro Gly Arg Asn Ser Phe
    1875                1880                1885
Tyr Met Gly Thr Cys Gln Asp Glu Pro Glu Gln Leu Asp Asp Trp Asn
1890                1895                1900
Arg Ile Ala Glu Leu Gln Gln Arg Asn Arg Val Cys Pro Pro His Leu
```

```
                    1905                1910                1915                1920
Lys Thr Cys Tyr Pro Leu Glu Ser Arg Pro Ser Leu Ser Leu Gly Thr
                1925                1930                1935

Ile Thr Asp Glu Glu Met Lys Thr Gly Asp Pro Gln Glu Thr Leu Arg
            1940                1945                1950

Arg Ala Ser Met Gln Pro Ile Gln Ile Ala Glu Gly Thr Gly Ile Thr
        1955                1960                1965

Thr Arg Gln Gln Arg Lys Arg Val Ser Leu Glu Pro His Gln Gly Pro
    1970                1975                1980

Gly Thr Pro Glu Ser Lys Lys Ala Thr Ser Cys Phe Pro Arg Pro Met
1985                1990                1995                2000

Thr Pro Arg Asp Arg His Glu Gly Arg Lys Gln Ser Thr Thr Glu Ala
                2005                2010                2015

Gln Lys Lys Ala Ala Pro Ala Ser Thr Lys Gln Ala Asp Arg Arg Gln
            2020                2025                2030

Ser Met Ala Phe Ser Ile Leu Asn Thr Pro Lys Lys Leu Gly Asn Ser
        2035                2040                2045

Leu Leu Arg Arg Gly Ala Ser Lys Lys Ala Leu Ser Lys Ala Ser Pro
    2050                2055                2060

Asn Thr Arg Ser Gly Thr Arg Arg Ser Pro Arg Ile Ala Thr Thr Thr
2065                2070                2075                2080

Ala Ser Ala Ala Thr Ala Ala Ile Gly Ala Thr Pro Arg Ala Lys
                2085                2090                2095

Gly Lys Ala Lys His
            2100

<210> SEQ ID NO 33
<211> LENGTH: 2115
<212> TYPE: PRT
<213> ORGANISM: Human

<400> SEQUENCE: 33

Met Thr Leu His Ala Thr Arg Gly Ala Ala Leu Leu Ser Trp Val Asn
1               5                   10                  15

Ser Leu His Val Ala Asp Pro Val Glu Ala Val Leu Gln Leu Gln Asp
            20                  25                  30

Cys Ser Ile Phe Ile Lys Ile Ile Asp Arg Ile His Gly Thr Glu Glu
        35                  40                  45

Gly Gln Gln Ile Leu Lys Gln Pro Val Ser Glu Arg Leu Asp Phe Val
    50                  55                  60

Cys Ser Phe Leu Gln Lys Asn Arg Lys His Pro Ser Ser Pro Glu Cys
65                  70                  75                  80

Leu Val Ser Ala Gln Lys Val Leu Glu Gly Ser Glu Leu Glu Leu Ala
                85                  90                  95

Lys Met Thr Met Leu Leu Leu Tyr His Ser Thr Met Ser Ser Lys Ser
            100                 105                 110

Pro Arg Asp Trp Glu Gln Phe Glu Tyr Lys Ile Gln Ala Glu Leu Ala
        115                 120                 125

Val Ile Leu Lys Phe Val Leu Asp His Glu Asp Gly Leu Asn Leu Asn
    130                 135                 140

Glu Asp Leu Glu Asn Phe Leu Gln Lys Ala Pro Val Pro Ser Thr Cys
145                 150                 155                 160

Ser Ser Thr Phe Pro Glu Glu Leu Ser Pro Pro Ser His Gln Ala Lys
                165                 170                 175
```

-continued

```
Arg Glu Ile Arg Phe Leu Glu Leu Gln Lys Val Ala Ser Ser Ser Ser
            180                 185                 190
Gly Asn Asn Phe Leu Ser Gly Pro Ala Ser Pro Met Gly Asp Ile
        195                 200                 205
Leu Gln Thr Pro Gln Phe Gln Met Arg Arg Leu Lys Lys Gln Leu Ala
        210                 215                 220
Asp Glu Arg Ser Asn Arg Asp Glu Leu Glu Leu Glu Leu Ala Glu Asn
225                 230                 235                 240
Arg Lys Leu Leu Thr Glu Lys Asp Ala Gln Ile Ala Met Met Gln Gln
                245                 250                 255
Arg Ile Asp Arg Leu Ala Leu Leu Asn Glu Lys Gln Ala Ala Ser Pro
                260                 265                 270
Leu Glu Pro Lys Glu Leu Glu Glu Leu Arg Asp Lys Asn Glu Ser Leu
                275                 280                 285
Thr Met Arg Leu His Glu Thr Leu Lys Gln Cys Gln Asp Leu Lys Thr
        290                 295                 300
Glu Lys Ser Gln Met Asp Arg Lys Ile Asn Gln Leu Ser Glu Glu Asn
305                 310                 315                 320
Gly Asp Leu Ser Phe Lys Leu Arg Glu Phe Ala Ser His Leu Gln Gln
                325                 330                 335
Leu Gln Asp Ala Leu Asn Glu Leu Thr Glu Glu His Ser Lys Ala Thr
                340                 345                 350
Gln Glu Trp Leu Glu Lys Gln Ala Gln Leu Glu Lys Glu Leu Ser Ala
            355                 360                 365
Ala Leu Gln Asp Lys Lys Cys Leu Glu Glu Lys Asn Glu Ile Leu Gln
        370                 375                 380
Gly Lys Leu Ser Gln Leu Glu Glu His Leu Ser Gln Leu Gln Asp Asn
385                 390                 395                 400
Pro Pro Gln Glu Lys Gly Glu Val Leu Gly Asp Val Leu Gln Leu Glu
                405                 410                 415
Thr Leu Lys Gln Glu Ala Ala Thr Leu Ala Ala Asn Asn Thr Gln Leu
                420                 425                 430
Gln Ala Arg Val Glu Met Leu Glu Thr Glu Arg Gly Gln Gln Glu Ala
            435                 440                 445
Lys Leu Leu Ala Glu Arg Gly His Phe Glu Glu Lys Gln Gln Leu
450                 455                 460
Ser Ser Leu Ile Thr Asp Leu Gln Ser Ser Ile Ser Asn Leu Ser Gln
465                 470                 475                 480
Ala Lys Glu Glu Leu Glu Gln Ala Ser Gln Ala His Gly Ala Arg Leu
                485                 490                 495
Thr Ala Gln Val Ala Ser Leu Thr Ser Glu Leu Thr Thr Leu Asn Ala
            500                 505                 510
Thr Ile Gln Gln Gln Asp Gln Glu Leu Ala Gly Leu Lys Gln Gln Ala
        515                 520                 525
Lys Glu Lys Gln Ala Gln Leu Ala Gln Thr Leu Gln Gln Gln Glu Gln
        530                 535                 540
Ala Ser Gln Gly Leu Arg His Gln Val Glu Gln Leu Ser Ser Ser Leu
545                 550                 555                 560
Lys Gln Lys Glu Gln Gln Leu Lys Glu Val Ala Glu Lys Gln Glu Ala
                565                 570                 575
Thr Arg Gln Asp His Ala Gln Gln Leu Ala Thr Ala Ala Glu Glu Arg
            580                 585                 590
Glu Ala Ser Leu Arg Glu Arg Asp Ala Ala Leu Lys Gln Leu Glu Ala
```

```
                595                 600                 605
Leu Glu Lys Glu Lys Ala Ala Lys Leu Glu Ile Leu Gln Gln Gln Leu
    610                 615                 620
Gln Val Ala Asn Glu Ala Arg Asp Ser Ala Gln Thr Ser Val Thr Gln
625                 630                 635                 640
Ala Gln Arg Glu Lys Ala Glu Leu Ser Arg Lys Val Glu Glu Leu Gln
                645                 650                 655
Ala Cys Val Glu Thr Ala Arg Gln Glu Gln His Glu Ala Gln Ala Gln
                660                 665                 670
Val Ala Glu Leu Glu Leu Gln Leu Arg Ser Glu Gln Gln Lys Ala Thr
                675                 680                 685
Glu Lys Glu Arg Val Ala Gln Glu Lys Asp Gln Leu Gln Glu Gln Leu
    690                 695                 700
Gln Ala Leu Lys Glu Ser Leu Lys Val Thr Lys Gly Ser Leu Glu Glu
705                 710                 715                 720
Glu Lys Arg Arg Ala Ala Asp Ala Leu Glu Gln Gln Arg Cys Ile
                725                 730                 735
Ser Glu Leu Lys Ala Glu Thr Arg Ser Leu Val Glu Gln His Lys Arg
    740                 745                 750
Glu Arg Lys Glu Leu Glu Glu Arg Ala Gly Arg Lys Gly Leu Glu
    755                 760                 765
Ala Arg Leu Gln Gln Leu Gly Glu Ala His Gln Ala Glu Thr Glu Val
    770                 775                 780
Leu Arg Arg Glu Leu Ala Glu Ala Met Ala Ala Gln His Thr Ala Glu
785                 790                 795                 800
Ser Glu Cys Glu Gln Leu Val Lys Glu Val Ala Ala Trp Arg Glu Arg
                805                 810                 815
Tyr Glu Asp Ser Gln Gln Glu Ala Gln Tyr Gly Ala Met Phe Gln
                820                 825                 830
Glu Gln Leu Met Thr Leu Lys Glu Cys Glu Lys Ala Arg Gln Glu
    835                 840                 845
Leu Gln Glu Ala Lys Glu Lys Val Ala Gly Ile Glu Ser His Ser Glu
    850                 855                 860
Leu Gln Ile Ser Arg Gln Gln Asn Glu Leu Ala Glu Leu His Ala Asn
865                 870                 875                 880
Leu Ala Arg Ala Leu Gln Gln Val Gln Glu Lys Glu Val Arg Ala Gln
                885                 890                 895
Lys Leu Ala Asp Asp Leu Ser Thr Leu Gln Glu Lys Met Ala Ala Thr
                900                 905                 910
Ser Lys Glu Val Ala Arg Leu Glu Thr Leu Val Arg Lys Ala Gly Glu
    915                 920                 925
Gln Gln Glu Thr Ala Ser Arg Glu Leu Val Lys Glu Pro Ala Arg Ala
    930                 935                 940
Gly Asp Arg Gln Pro Glu Trp Leu Glu Glu Gln Gly Arg Gln Phe
945                 950                 955                 960
Cys Ser Thr Gln Ala Ala Leu Gln Ala Met Glu Arg Glu Ala Glu Gln
                965                 970                 975
Met Gly Asn Glu Leu Glu Arg Leu Arg Ala Ala Leu Met Glu Ser Gln
                980                 985                 990
Gly Gln Gln Gln Glu Glu Arg Gly Gln Gln Glu Arg Glu Val Ala Arg
    995                1000                1005
Leu Thr Gln Glu Arg Gly Arg Ala Gln Ala Asp Leu Ala Leu Glu Lys
    1010                1015                1020
```

-continued

Ala Ala Arg Ala Glu Leu Glu Met Arg Leu Gln Asn Ala Leu Asn Glu
1025                1030                1035                1040

Gln Arg Val Glu Phe Ala Thr Leu Gln Glu Ala Leu Ala His Ala Leu
            1045                1050                1055

Thr Glu Lys Glu Gly Lys Asp Gln Glu Leu Ala Lys Leu Arg Gly Leu
        1060                1065                1070

Glu Ala Ala Gln Ile Lys Glu Leu Glu Leu Arg Gln Thr Val Lys
    1075                1080                1085

Gln Leu Lys Glu Gln Leu Ala Lys Lys Glu Lys Glu His Ala Ser Gly
1090                1095                1100

Ser Gly Ala Gln Ser Glu Ala Ala Gly Arg Thr Glu Pro Thr Gly Pro
1105                1110                1115                1120

Lys Leu Glu Ala Leu Arg Ala Glu Val Ser Lys Leu Glu Gln Gln Cys
            1125                1130                1135

Gln Lys Gln Gln Glu Gln Ala Asp Ser Leu Glu Arg Ser Leu Glu Ala
            1140                1145                1150

Glu Arg Ala Ser Arg Ala Glu Arg Asp Ser Ala Leu Glu Thr Leu Gln
    1155                1160                1165

Gly Gln Leu Glu Glu Lys Ala Gln Glu Leu Gly His Ser Gln Ser Ala
1170                1175                1180

Leu Ala Ser Ala Gln Arg Glu Leu Ala Ala Phe Arg Thr Lys Val Gln
1185                1190                1195                1200

Asp His Ser Lys Ala Glu Asp Glu Trp Lys Ala Gln Val Ala Arg Gly
            1205                1210                1215

Arg Gln Glu Ala Glu Arg Lys Asn Ser Leu Ile Ser Ser Leu Glu Glu
    1220                1225                1230

Glu Val Ser Ile Leu Asn Arg Gln Val Leu Glu Lys Glu Gly Glu Ser
        1235                1240                1245

Lys Glu Leu Lys Arg Leu Val Met Ala Glu Ser Glu Lys Ser Gln Lys
1250                1255                1260

Leu Glu Glu Arg Leu Arg Leu Leu Gln Ala Glu Thr Ala Ser Asn Ser
1265                1270                1275                1280

Ala Arg Ala Ala Glu Arg Ser Ser Ala Leu Arg Glu Val Gln Ser
            1285                1290                1295

Leu Arg Glu Glu Ala Glu Lys Gln Arg Val Ala Ser Glu Asn Leu Arg
    1300                1305                1310

Gln Glu Leu Thr Ser Gln Ala Glu Arg Ala Glu Glu Leu Gly Gln Glu
        1315                1320                1325

Leu Lys Ala Trp Gln Glu Lys Phe Phe Gln Lys Glu Gln Ala Leu Ser
    1330                1335                1340

Thr Leu Gln Leu Glu His Thr Ser Thr Gln Ala Leu Val Ser Glu Leu
1345                1350                1355                1360

Leu Pro Ala Lys His Leu Cys Gln Gln Leu Gln Ala Glu Gln Ala Ala
            1365                1370                1375

Ala Glu Lys Arg His Arg Glu Glu Leu Glu Gln Ser Lys Gln Ala Ala
            1380                1385                1390

Gly Gly Leu Arg Ala Glu Leu Leu Arg Ala Gln Arg Glu Leu Gly Glu
        1395                1400                1405

Leu Ile Pro Leu Arg Gln Lys Val Ala Glu Gln Glu Arg Thr Ala Gln
        1410                1415                1420

Gln Leu Arg Ala Glu Lys Ala Ser Tyr Ala Glu Gln Leu Ser Met Leu
1425                1430                1435                1440

-continued

Lys Lys Ala His Gly Leu Leu Ala Glu Glu Asn Arg Gly Leu Gly Glu
            1445                1450                1455

Arg Ala Asn Leu Gly Arg Gln Phe Leu Glu Val Glu Leu Asp Gln Ala
            1460                1465                1470

Arg Glu Lys Tyr Val Gln Glu Leu Ala Ala Val Arg Ala Asp Ala Glu
            1475                1480                1485

Thr Arg Leu Ala Glu Val Gln Arg Glu Ala Gln Ser Thr Ala Arg Glu
            1490                1495                1500

Leu Glu Val Met Thr Ala Lys Tyr Glu Gly Ala Lys Val Lys Val Leu
1505                1510                1515                1520

Glu Glu Arg Gln Arg Phe Gln Glu Glu Arg Gln Lys Leu Thr Ala Gln
            1525                1530                1535

Val Glu Gln Leu Glu Val Phe Gln Arg Glu Gln Thr Lys Gln Val Glu
            1540                1545                1550

Glu Leu Ser Lys Lys Leu Ala Asp Ser Asp Gln Ala Ser Lys Val Gln
            1555                1560                1565

Gln Gln Lys Leu Lys Ala Val Gln Ala Gln Gly Gly Glu Ser Gln Gln
            1570                1575                1580

Glu Ala Gln Arg Leu Gln Ala Gln Leu Asn Glu Leu Gln Ala Gln Leu
1585                1590                1595                1600

Ser Gln Lys Glu Gln Ala Ala Glu His Tyr Lys Leu Gln Met Glu Lys
            1605                1610                1615

Ala Lys Thr His Tyr Asp Ala Lys Lys Gln Gln Asn Gln Glu Leu Gln
            1620                1625                1630

Glu Gln Leu Arg Ser Leu Glu Gln Leu Gln Lys Glu Asn Lys Glu Leu
            1635                1640                1645

Arg Ala Glu Ala Glu Arg Leu Gly His Glu Leu Gln Gln Ala Gly Leu
            1650                1655                1660

Lys Thr Lys Glu Ala Glu Gln Thr Cys Arg His Leu Thr Ala Gln Val
1665                1670                1675                1680

Arg Ser Leu Glu Ala Gln Val Ala His Ala Asp Gln Gln Leu Arg Asp
            1685                1690                1695

Leu Gly Lys Phe Gln Val Ala Thr Asp Ala Leu Lys Ser Arg Glu Pro
            1700                1705                1710

Gln Ala Lys Pro Gln Leu Asp Leu Ser Ile Asp Ser Leu Asp Leu Ser
            1715                1720                1725

Cys Glu Glu Gly Thr Pro Leu Ser Ile Thr Ser Lys Leu Pro Arg Thr
1730                1735                1740

Gln Pro Asp Gly Thr Ser Val Pro Gly Glu Pro Ala Ser Pro Ile Ser
1745                1750                1755                1760

Gln Arg Leu Pro Pro Lys Val Glu Ser Leu Glu Ser Leu Tyr Phe Thr
            1765                1770                1775

Pro Ile Pro Ala Arg Ser Gln Ala Pro Leu Glu Ser Ser Leu Asp Ser
            1780                1785                1790

Leu Gly Asp Val Phe Gln Asp Ser Gly Arg Lys Thr Arg Ser Ala Arg
            1795                1800                1805

Arg Arg Thr Thr Gln Ile Ile Asn Ile Thr Met Thr Lys Lys Leu Asp
            1810                1815                1820

Val Glu Glu Pro Asp Ser Ala Asn Ser Ser Phe Tyr Ser Thr Arg Ser
1825                1830                1835                1840

Ala Pro Ala Ser Gln Ala Ser Leu Arg Ala Thr Ser Ser Thr Gln Ser
            1845                1850                1855

Leu Ala Arg Leu Gly Ser Pro Asp Tyr Gly Asn Ser Ala Leu Leu Ser 1860                1865                1870
Leu Pro Gly Tyr Arg Pro Thr Thr Arg Ser Ser Ala Arg Arg Ser Gln
            1875                1880                1885

Ala Gly Val Ser Ser Gly Ala Pro Pro Gly Arg Asn Ser Phe Tyr Met
            1890                1895                1900

Gly Thr Cys Gln Asp Glu Pro Glu Gln Leu Asp Asp Trp Asn Arg Ile
1905                1910                1915                1920

Ala Glu Leu Gln Gln Arg Asn Arg Val Cys Pro Pro His Leu Lys Thr
            1925                1930                1935

Cys Tyr Pro Leu Glu Ser Arg Pro Ser Leu Ser Leu Gly Thr Ile Thr
            1940                1945                1950

Asp Glu Glu Met Lys Thr Gly Asp Pro Gln Glu Thr Leu Arg Arg Ala
            1955                1960                1965

Ser Met Gln Pro Ile Gln Ile Ala Glu Gly Thr Gly Ile Thr Thr Arg
            1970                1975                1980

Gln Gln Arg Lys Arg Val Ser Leu Glu Pro His Gln Gly Pro Gly Thr
1985                1990                1995                2000

Pro Glu Ser Lys Lys Ala Thr Ser Cys Phe Pro Arg Pro Met Thr Pro
            2005                2010                2015

Arg Asp Arg His Glu Gly Arg Lys Gln Ser Thr Thr Glu Ala Gln Lys
            2020                2025                2030

Lys Ala Ala Pro Ala Ser Thr Lys Gln Ala Asp Arg Arg Gln Ser Met
            2035                2040                2045

Ala Phe Ser Ile Leu Asn Thr Pro Lys Lys Leu Gly Asn Ser Leu Leu
            2050                2055                2060

Arg Arg Gly Ala Ser Lys Lys Ala Leu Ser Lys Ala Ser Pro Asn Thr
2065                2070                2075                2080

Arg Ser Gly Thr Arg Arg Ser Pro Arg Ile Ala Thr Thr Ala Ser
            2085                2090                2095

Ala Ala Thr Ala Ala Ala Ile Gly Ala Thr Pro Arg Ala Lys Gly Lys
            2100                2105                2110

Ala Lys His
       2115

<210> SEQ ID NO 34
<211> LENGTH: 4096
<212> TYPE: PRT
<213> ORGANISM: Human
<220> FEATURE:
<221> NAME/KEY: VARIANT
<222> LOCATION: (1)...(4096)
<223> OTHER INFORMATION: Xaa = Any Amino Acid

<400> SEQUENCE: 34

Met Ala Gly Ser Gly Ala Gly Val Arg Cys Ser Leu Leu Arg Leu Gln
 1               5                  10                  15

Glu Thr Leu Ser Ala Ala Asp Arg Cys Gly Ala Ala Leu Ala Gly His
            20                  25                  30

Gln Leu Ile Arg Gly Leu Gly Gln Glu Cys Val Leu Ser Ser Ser Pro
         35                  40                  45

Ala Val Leu Ala Leu Gln Thr Ser Leu Val Phe Ser Arg Asp Phe Gly
    50                  55                  60

Leu Leu Val Phe Val Arg Lys Ser Leu Asn Ser Ile Glu Phe Arg Glu
65                  70                  75                  80

Cys Arg Glu Glu Ile Leu Lys Phe Leu Cys Ile Phe Leu Glu Lys Met
                85                  90                  95

```
Gly Gln Lys Ile Ala Pro Tyr Ser Val Glu Ile Lys Asn Thr Cys Thr
            100                 105                 110
Ser Val Tyr Thr Lys Asp Arg Ala Ala Lys Cys Lys Ile Pro Ala Leu
            115                 120                 125
Asp Leu Leu Ile Lys Leu Leu Gln Thr Phe Arg Ser Ser Arg Leu Met
            130                 135                 140
Asp Glu Phe Lys Ile Gly Glu Leu Phe Ser Lys Phe Tyr Gly Glu Leu
145                 150                 155                 160
Ala Leu Lys Lys Lys Ile Pro Asp Thr Val Leu Glu Lys Val Tyr Glu
                165                 170                 175
Leu Leu Gly Leu Leu Gly Glu Val His Pro Ser Glu Met Ile Asn Asn
            180                 185                 190
Ala Glu Asn Leu Phe Arg Ala Phe Leu Gly Glu Leu Lys Thr Gln Met
            195                 200                 205
Thr Ser Ala Val Arg Glu Pro Lys Leu Pro Val Leu Ala Gly Cys Leu
            210                 215                 220
Lys Gly Leu Ser Ser Leu Leu Cys Asn Phe Thr Lys Ser Met Glu Glu
225                 230                 235                 240
Asp Pro Gln Thr Ser Arg Glu Ile Phe Asn Phe Val Leu Lys Ala Ile
                245                 250                 255
Arg Pro Gln Ile Asp Leu Lys Arg Tyr Ala Val Pro Ser Ala Gly Leu
            260                 265                 270
Arg Leu Phe Ala Leu His Ala Ser Gln Phe Ser Thr Cys Leu Leu Asp
            275                 280                 285
Asn Tyr Val Ser Leu Phe Glu Val Leu Ile Lys Trp Cys Ala His Thr
            290                 295                 300
Asn Val Glu Leu Lys Lys Ala Ala Leu Ser Ala Leu Glu Ser Phe Leu
305                 310                 315                 320
Lys Gln Val Ser Asn Met Val Ala Lys Asn Ala Glu Met His Lys Asn
                325                 330                 335
Lys Leu Gln Tyr Glu Met Glu Gln Phe Tyr Gly Ile Ile Arg Asn Val
            340                 345                 350
Asp Ser Asn Asn Lys Glu Leu Ser Ile Ala Ile Arg Gly Tyr Gly Leu
            355                 360                 365
Phe Ala Gly Pro Cys Lys Val Ile Asn Ala Lys Asp Val Asp Phe Met
            370                 375                 380
Tyr Val Glu Leu Ile Gln Arg Cys Lys Gln Met Phe Leu Thr Gln Thr
385                 390                 395                 400
Asp Thr Gly Asp Tyr Arg Val Tyr Gln Met Pro Ser Phe Leu Gln Ser
                405                 410                 415
Val Ala Ser Val Leu Leu Tyr Leu Asp Thr Val Pro Glu Val Tyr Thr
            420                 425                 430
Pro Val Leu Glu His Leu Val Val Met Gln Ile Asp Ser Phe Pro Gln
            435                 440                 445
Tyr Ser Pro Lys Met Gln Leu Val Cys Cys Arg Ala Ile Val Lys Val
            450                 455                 460
Phe Leu Ala Leu Ala Ala Lys Gly Pro Val Leu Arg Asn Cys Ile Ser
465                 470                 475                 480
Thr Val Val His Gln Gly Leu Ile Arg Ile Cys Ser Lys Pro Val Val
                485                 490                 495
Leu Pro Lys Gly Pro Glu Ser Glu Ser Glu Asp His Arg Ala Ser Gly
            500                 505                 510
```

-continued

```
Glu Val Arg Thr Gly Lys Trp Lys Val Pro Thr Tyr Lys Asp Tyr Val
            515                 520                 525

Asp Leu Phe Arg His Leu Leu Ser Ser Asp Gln Met Met Asp Ser Ile
            530                 535                 540

Leu Ala Asp Glu Ala Phe Phe Ser Val Asn Ser Ser Glu Ser Leu
545                 550                 555                 560

Asn His Leu Leu Tyr Asp Glu Phe Val Lys Ser Val Leu Lys Ile Val
                565                 570                 575

Glu Lys Leu Asp Leu Thr Leu Glu Ile Gln Thr Val Gly Glu Gln Glu
            580                 585                 590

Asn Gly Asp Glu Ala Pro Gly Val Trp Met Ile Pro Thr Ser Asp Pro
            595                 600                 605

Ala Ala Asn Leu His Pro Ala Lys Pro Lys Asp Phe Ser Ala Phe Ile
610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
                645                 650                 655

Ser Thr Arg Leu Pro Leu Ile Ser Gly Phe Tyr Lys Leu Leu Ser Ile
            660                 665                 670

Thr Val Arg Asn Ala Lys Lys Ile Lys Tyr Phe Glu Gly Val Ser Pro
            675                 680                 685

Lys Ser Leu Lys His Ser Pro Glu Asp Pro Glu Lys Tyr Ser Cys Phe
690                 695                 700

Ala Leu Phe Val Lys Phe Gly Lys Glu Val Ala Val Lys Met Lys Gln
705                 710                 715                 720

Tyr Lys Asp Glu Leu Leu Ala Ser Cys Leu Thr Phe Leu Leu Ser Leu
                725                 730                 735

Pro His Asn Ile Ile Glu Leu Asp Val Arg Ala Tyr Val Pro Ala Leu
            740                 745                 750

Gln Met Ala Phe Lys Leu Gly Leu Ser Tyr Thr Pro Leu Ala Glu Val
            755                 760                 765

Gly Leu Asn Ala Leu Glu Glu Trp Ser Ile Tyr Ile Asp Arg His Val
            770                 775                 780

Met Gln Pro Tyr Tyr Lys Asp Ile Leu Pro Cys Leu Asp Gly Tyr Leu
785                 790                 795                 800

Lys Thr Ser Ala Leu Ser Asp Glu Thr Lys Asn Asn Trp Glu Val Ser
                805                 810                 815

Ala Leu Ser Arg Ala Ala Gln Lys Gly Phe Asn Lys Val Val Leu Lys
            820                 825                 830

His Leu Lys Lys Thr Lys Asn Leu Ser Ser Asn Glu Ala Ile Ser Leu
            835                 840                 845

Glu Glu Ile Arg Ile Arg Val Val Gln Met Leu Gly Ser Leu Gly Gly
850                 855                 860

Gln Ile Asn Lys Asn Leu Leu Thr Val Thr Ser Ser Asp Glu Met Met
865                 870                 875                 880

Lys Ser Tyr Val Ala Trp Asp Arg Glu Lys Arg Leu Ser Phe Ala Val
                885                 890                 895

Pro Phe Arg Glu Met Lys Pro Val Ile Phe Leu Asp Val Phe Leu Pro
            900                 905                 910

Arg Val Thr Glu Leu Ala Leu Thr Ala Ser Asp Arg Gln Thr Lys Val
            915                 920                 925

Ala Ala Cys Glu Leu Leu His Ser Met Val Met Phe Met Leu Gly Lys
```

-continued

```
            930             935             940
Ala Thr Gln Met Pro Glu Gly Gly Gln Gly Ala Pro Pro Met Tyr Gln
945             950             955             960

Leu Tyr Lys Arg Thr Phe Pro Val Leu Leu Arg Leu Ala Cys Asp Val
            965             970             975

Asp Gln Val Thr Arg Gln Leu Tyr Glu Pro Leu Val Met Gln Leu Ile
            980             985             990

His Trp Phe Thr Asn Asn Lys Lys Phe Glu Ser Gln Asp Thr Val Ser
            995             1000            1005

Leu Leu Glu Ala Ile Leu Asp Gly Ile Val Asp Pro Val Asp Ser Thr
            1010            1015            1020

Leu Arg Asp Phe Cys Gly Arg Cys Ile Arg Glu Phe Leu Lys Trp Ser
1025            1030            1035            1040

Ile Lys Gln Ile Thr Pro Gln Gln Glu Lys Ser Pro Val Asn Thr
            1045            1050            1055

Lys Ser Leu Phe Lys Arg Leu Tyr Ser Leu Ala Leu His Pro Asn Ala
            1060            1065            1070

Phe Lys Arg Leu Gly Ala Ser Leu Ala Phe Asn Asn Ile Tyr Arg Glu
            1075            1080            1085

Phe Arg Glu Glu Glu Ser Leu Val Glu Gln Phe Val Phe Glu Ala Leu
            1090            1095            1100

Val Ile Tyr Met Glu Ser Leu Ala Leu Ala His Ala Asp Glu Lys Ser
1105            1110            1115            1120

Leu Gly Thr Ile Gln Gln Cys Cys Asp Ala Ile Asp His Leu Cys Arg
            1125            1130            1135

Ile Ile Glu Lys Lys His Val Ser Leu Asn Lys Ala Lys Lys Arg Arg
            1140            1145            1150

Leu Pro Arg Gly Phe Pro Pro Ser Ala Ser Leu Cys Leu Leu Asp Leu
            1155            1160            1165

Val Lys Trp Leu Leu Ala His Cys Gly Arg Pro Gln Thr Glu Cys Arg
            1170            1175            1180

His Lys Ser Ile Glu Leu Phe Tyr Lys Phe Val Pro Leu Leu Pro Gly
1185            1190            1195            1200

Asn Arg Ser Pro Asn Leu Trp Leu Lys Asp Val Leu Lys Glu Glu Gly
            1205            1210            1215

Val Ser Phe Leu Ile Asn Thr Phe Glu Gly Gly Gly Cys Gly Gln Pro
            1220            1225            1230

Ser Gly Ile Leu Ala Gln Pro Thr Leu Leu Tyr Leu Arg Gly Pro Phe
            1235            1240            1245

Ser Leu Gln Ala Thr Leu Cys Trp Leu Asp Leu Leu Leu Ala Ala Leu
            1250            1255            1260

Glu Cys Tyr Asn Thr Phe Ile Gly Glu Arg Thr Val Gly Ala Leu Gln
1265            1270            1275            1280

Val Leu Gly Thr Glu Ala Gln Ser Ser Leu Leu Lys Ala Val Ala Phe
            1285            1290            1295

Phe Leu Glu Ser Ile Ala Met His Asp Ile Ala Ala Glu Lys Cys
            1300            1305            1310

Phe Gly Thr Gly Ala Ala Gly Asn Arg Thr Ser Pro Gln Glu Gly Glu
            1315            1320            1325

Arg Tyr Asn Tyr Ser Lys Cys Thr Val Val Arg Ile Met Glu Phe
            1330            1335            1340

Thr Thr Thr Leu Leu Asn Thr Ser Pro Glu Gly Trp Lys Leu Leu Lys
1345            1350            1355            1360
```

```
Lys Asp Leu Cys Asn Thr His Leu Met Arg Val Leu Val Gln Thr Leu
            1365                1370                1375
Cys Glu Pro Ala Ser Ile Gly Phe Asn Ile Gly Asp Val Gln Val Met
        1380                1385                1390
Ala His Leu Pro Asp Val Cys Val Asn Leu Met Lys Ala Leu Lys Met
    1395                1400                1405
Ser Pro Tyr Lys Asp Ile Leu Glu Thr His Leu Arg Glu Lys Ile Thr
1410                1415                1420
Ala Gln Ser Ile Glu Glu Leu Cys Ala Val Asn Leu Tyr Gly Pro Asp
1425                1430                1435                1440
Ala Gln Val Asp Arg Ser Arg Leu Ala Ala Val Val Ser Ala Cys Lys
            1445                1450                1455
Gln Leu His Arg Ala Gly Leu Leu His Asn Ile Leu Pro Ser Gln Ser
        1460                1465                1470
Thr Asp Leu His His Ser Val Gly Thr Glu Leu Leu Ser Leu Val Tyr
    1475                1480                1485
Lys Gly Ile Ala Pro Gly Asp Glu Arg Gln Cys Leu Pro Ser Leu Asp
1490                1495                1500
Leu Ser Cys Lys Gln Leu Ala Ser Gly Leu Leu Glu Leu Ala Phe Ala
1505                1510                1515                1520
Phe Gly Gly Leu Cys Glu Arg Leu Val Ser Leu Leu Asn Pro Ala
            1525                1530                1535
Val Leu Ser Thr Ala Ser Leu Gly Ser Ser Gln Gly Ser Val Ile His
        1540                1545                1550
Phe Ser His Gly Glu Tyr Phe Tyr Ser Leu Phe Ser Glu Thr Ile Asn
    1555                1560                1565
Thr Glu Leu Leu Lys Asn Leu Asp Leu Ala Val Leu Glu Leu Met Gln
    1570                1575                1580
Ser Ser Val Asp Asn Thr Lys Met Val Ser Ala Val Leu Asn Gly Met
1585                1590                1595                1600
Leu Asp Gln Ser Phe Arg Glu Arg Ala Asn Gln Lys His Gln Gly Leu
            1605                1610                1615
Lys Leu Ala Thr Thr Ile Leu Gln His Trp Lys Lys Cys Asp Ser Trp
        1620                1625                1630
Trp Ala Lys Asp Ser Pro Leu Glu Thr Lys Met Ala Val Leu Ala Leu
    1635                1640                1645
Leu Ala Lys Ile Leu Gln Ile Asp Ser Ser Val Ser Phe Asn Thr Ser
    1650                1655                1660
His Gly Ser Phe Pro Glu Val Phe Thr Thr Tyr Ile Ser Leu Leu Ala
1665                1670                1675                1680
Asp Thr Lys Leu Asp Leu His Leu Lys Gly Gln Ala Val Thr Leu Leu
            1685                1690                1695
Pro Phe Phe Thr Ser Leu Thr Gly Gly Ser Leu Glu Glu Leu Arg Arg
        1700                1705                1710
Val Leu Glu Gln Leu Ile Val Ala His Phe Pro Met Gln Ser Arg Glu
    1715                1720                1725
Phe Pro Pro Gly Thr Pro Arg Phe Asn Asn Tyr Val Asp Cys Met Lys
    1730                1735                1740
Lys Phe Leu Asp Ala Leu Glu Leu Ser Gln Ser Pro Met Leu Leu Glu
1745                1750                1755                1760
Leu Met Thr Glu Val Leu Cys Arg Glu Gln Gln His Val Met Glu Glu
            1765                1770                1775
```

-continued

```
Leu Phe Gln Ser Ser Phe Arg Arg Ile Ala Arg Arg Gly Ser Cys Val
            1780                1785                1790

Thr Gln Val Gly Leu Leu Glu Ser Val Tyr Glu Met Phe Arg Lys Asp
        1795                1800                1805

Asp Pro Arg Leu Ser Phe Thr Arg Gln Ser Phe Val Asp Arg Ser Leu
        1810                1815                1820

Leu Thr Leu Leu Trp His Cys Ser Leu Asp Ala Leu Arg Glu Phe Phe
1825                1830                1835                1840

Ser Thr Ile Val Val Asp Ala Ile Asp Val Leu Lys Ser Arg Phe Thr
                1845                1850                1855

Lys Leu Asn Glu Ser Thr Phe Asp Thr Gln Ile Thr Lys Lys Met Gly
            1860                1865                1870

Tyr Tyr Lys Ile Leu Asp Val Met Tyr Ser Arg Leu Pro Lys Asp Asp
        1875                1880                1885

Val His Ala Lys Glu Ser Lys Ile Asn Gln Val Phe His Gly Ser Cys
    1890                1895                1900

Ile Thr Glu Gly Asn Glu Leu Thr Lys Thr Leu Ile Lys Leu Cys Tyr
1905                1910                1915                1920

Asp Ala Phe Thr Glu Asn Met Ala Gly Glu Asn Gln Leu Leu Glu Arg
                1925                1930                1935

Arg Arg Leu Tyr His Cys Ala Ala Tyr Asn Cys Ala Ile Ser Val Ile
            1940                1945                1950

Cys Cys Val Phe Asn Glu Leu Lys Phe Tyr Gln Gly Phe Leu Phe Ser
        1955                1960                1965

Glu Lys Pro Glu Lys Asn Leu Leu Ile Phe Glu Asn Leu Ile Asp Leu
    1970                1975                1980

Lys Arg Arg Tyr Asn Phe Pro Val Glu Val Glu Val Pro Met Glu Arg
1985                1990                1995                2000

Lys Lys Lys Tyr Ile Glu Ile Arg Lys Glu Ala Arg Glu Ala Ala Asn
                2005                2010                2015

Gly Asp Ser Asp Gly Pro Ser Tyr Met Ser Ser Leu Ser Tyr Leu Ala
            2020                2025                2030

Asp Ser Thr Leu Ser Glu Glu Met Ser Gln Phe Asp Phe Ser Thr Gly
        2035                2040                2045

Val Gln Ser Tyr Ser Tyr Ser Ser Gln Asp Pro Arg Pro Ala Thr Gly
    2050                2055                2060

Arg Phe Arg Arg Arg Glu Gln Arg Asp Pro Thr Val His Asp Asp Val
2065                2070                2075                2080

Leu Glu Leu Glu Met Asp Glu Leu Asn Arg His Glu Cys Met Ala Pro
                2085                2090                2095

Leu Thr Ala Leu Val Lys His Met His Arg Ser Leu Gly Pro Pro Gln
            2100                2105                2110

Gly Glu Glu Asp Ser Val Pro Arg Asp Leu Pro Ser Trp Met Lys Phe
        2115                2120                2125

Leu His Gly Lys Leu Gly Asn Pro Ile Val Pro Leu Asn Ile Arg Leu
    2130                2135                2140

Phe Leu Ala Lys Leu Val Ile Asn Thr Glu Val Phe Arg Pro Tyr
2145                2150                2155                2160

Ala Lys His Trp Leu Ser Pro Leu Leu Gln Leu Ala Ala Ser Glu Asn
                2165                2170                2175

Asn Gly Gly Glu Gly Ile His Tyr Met Val Val Glu Ile Val Ala Thr
            2180                2185                2190

Ile Leu Ser Trp Thr Gly Leu Ala Thr Pro Thr Gly Val Pro Lys Asp
```

-continued

```
                2195                2200                2205
Glu Val Leu Ala Asn Arg Leu Leu Asn Phe Leu Met Lys His Val Phe
                2210                2215                2220
His Pro Lys Arg Ala Val Phe Arg His Asn Leu Glu Ile Ile Lys Thr
2225                2230                2235                2240
Leu Val Glu Cys Trp Lys Asp Cys Leu Ser Ile Pro Tyr Arg Leu Ile
                2245                2250                2255
Phe Glu Lys Phe Ser Gly Lys Asp Pro Asn Ser Lys Asp Asn Ser Val
                2260                2265                2270
Gly Ile Gln Leu Leu Gly Ile Val Met Ala Asn Asp Leu Pro Pro Tyr
                2275                2280                2285
Asp Pro Gln Cys Gly Ile Gln Ser Ser Glu Tyr Phe Gln Ala Leu Val
                2290                2295                2300
Asn Asn Met Ser Phe Val Arg Tyr Lys Glu Val Tyr Ala Ala Ala Ala
2305                2310                2315                2320
Glu Val Leu Gly Leu Ile Leu Arg Tyr Val Met Glu Arg Lys Asn Ile
                2325                2330                2335
Leu Glu Glu Ser Leu Cys Glu Leu Val Ala Lys Gln Leu Lys Gln His
                2340                2345                2350
Gln Asn Thr Met Glu Asp Lys Phe Ile Val Cys Leu Asn Lys Val Thr
                2355                2360                2365
Lys Ser Phe Pro Pro Leu Ala Asp Arg Phe Met Asn Ala Val Phe Phe
2370                2375                2380
Leu Leu Pro Lys Phe His Gly Val Leu Lys Thr Leu Cys Leu Glu Val
2385                2390                2395                2400
Val Leu Cys Arg Val Glu Gly Met Thr Glu Leu Tyr Phe Gln Leu Lys
                2405                2410                2415
Ser Lys Asp Phe Val Gln Val Met Arg His Arg Asp Glu Arg Gln Lys
                2420                2425                2430
Val Cys Leu Asp Ile Ile Tyr Lys Met Met Pro Lys Leu Lys Pro Val
                2435                2440                2445
Glu Leu Arg Glu Leu Leu Asn Pro Val Val Glu Phe Val Ser His Pro
                2450                2455                2460
Ser Thr Thr Cys Arg Glu Gln Met Tyr Asn Ile Leu Met Trp Ile His
2465                2470                2475                2480
Asp Asn Tyr Arg Asp Pro Glu Ser Glu Thr Asp Asn Asp Ser Gln Glu
                2485                2490                2495
Ile Phe Lys Leu Ala Lys Asp Val Leu Ile Gln Gly Leu Ile Asp Glu
                2500                2505                2510
Asn Pro Gly Leu Gln Leu Ile Ile Arg Asn Phe Trp Ser His Glu Thr
                2515                2520                2525
Arg Leu Pro Ser Asn Thr Leu Asp Arg Leu Leu Ala Leu Asn Ser Leu
                2530                2535                2540
Tyr Ser Pro Lys Ile Glu Val His Phe Leu Ser Leu Ala Thr Asn Phe
2545                2550                2555                2560
Leu Leu Glu Met Thr Ser Met Ser Pro Asp Tyr Pro Asn Pro Met Phe
                2565                2570                2575
Glu His Pro Leu Ser Glu Cys Glu Phe Gln Glu Tyr Thr Ile Asp Ser
                2580                2585                2590
Asp Trp Arg Phe Arg Ser Thr Val Leu Thr Pro Met Phe Val Glu Thr
                2595                2600                2605
Gln Ala Ser Gln Gly Thr Leu Gln Thr Arg Thr Gln Glu Gly Ser Leu
                2610                2615                2620
```

```
Ser Ala Arg Trp Pro Val Ala Gly Gln Ile Arg Ala Thr Gln Gln Gln
2625                2630                2635                2640

His Asp Phe Thr Leu Thr Gln Thr Ala Asp Gly Arg Ser Ser Phe Asp
            2645                2650                2655

Trp Leu Thr Gly Ser Ser Thr Asp Pro Leu Val Asp His Thr Ser Pro
            2660                2665                2670

Ser Ser Asp Ser Leu Leu Phe Ala His Lys Arg Ser Glu Arg Leu Gln
        2675                2680                2685

Arg Ala Pro Leu Lys Ser Val Gly Pro Asp Phe Gly Lys Lys Arg Leu
    2690                2695                2700

Gly Leu Pro Gly Asp Glu Val Asp Asn Lys Val Lys Gly Ala Ala Gly
2705                2710                2715                2720

Arg Thr Asp Leu Leu Arg Leu Arg Arg Phe Met Arg Asp Gln Glu
            2725                2730                2735

Lys Leu Ser Leu Met Tyr Ala Arg Lys Gly Val Ala Glu Gln Lys Arg
            2740                2745                2750

Glu Lys Glu Ile Lys Ser Glu Leu Lys Met Lys Gln Asp Ala Gln Val
        2755                2760                2765

Val Leu Tyr Arg Ser Tyr Arg His Gly Asp Leu Pro Asp Ile Gln Ile
    2770                2775                2780

Lys His Ser Ser Leu Ile Thr Pro Leu Gln Ala Val Ala Gln Arg Asp
2785                2790                2795                2800

Pro Ile Ile Ala Lys Gln Leu Phe Ser Ser Leu Phe Ser Gly Ile Leu
            2805                2810                2815

Lys Glu Met Asp Lys Phe Lys Thr Leu Ser Glu Lys Asn Asn Ile Thr
            2820                2825                2830

Gln Lys Leu Leu Gln Asp Phe Asn Arg Phe Leu Asn Thr Thr Phe Ser
        2835                2840                2845

Phe Phe Pro Pro Phe Val Ser Cys Ile Gln Asp Ile Ser Cys Gln His
    2850                2855                2860

Ala Ala Leu Leu Ser Leu Asp Pro Ala Ala Val Ser Ala Gly Cys Leu
2865                2870                2875                2880

Ala Ser Leu Gln Gln Pro Val Gly Ile Arg Leu Leu Glu Glu Ala Leu
            2885                2890                2895

Leu Arg Leu Leu Pro Ala Glu Leu Pro Ala Lys Arg Val Arg Gly Lys
            2900                2905                2910

Ala Arg Leu Pro Pro Asp Val Leu Arg Trp Val Glu Leu Ala Lys Leu
        2915                2920                2925

Tyr Arg Ser Ile Gly Glu Tyr Asp Val Leu Arg Gly Ile Phe Thr Ser
    2930                2935                2940

Glu Ile Gly Thr Lys Gln Ile Thr Gln Ser Ala Leu Leu Ala Glu Ala
2945                2950                2955                2960

Arg Ser Asp Tyr Ser Glu Ala Ala Lys Gln Tyr Asp Glu Ala Leu Asn
            2965                2970                2975

Lys Gln Asp Trp Val Asp Gly Glu Pro Thr Glu Ala Glu Lys Asp Phe
            2980                2985                2990

Trp Glu Leu Ala Ser Leu Asp Cys Tyr Asn His Leu Ala Glu Trp Lys
        2995                3000                3005

Ser Leu Glu Tyr Cys Ser Thr Ala Ser Ile Asp Ser Glu Asn Pro Pro
    3010                3015                3020

Asp Leu Asn Lys Ile Trp Ser Glu Pro Phe Tyr Gln Glu Thr Tyr Leu
3025                3030                3035                3040
```

```
Pro Tyr Met Ile Arg Ser Lys Leu Lys Leu Leu Gln Gly Glu Ala
            3045                3050                3055

Asp Gln Ser Leu Leu Thr Phe Ile Asp Lys Ala Met His Gly Glu Leu
            3060                3065            3070

Gln Lys Ala Ile Leu Glu Leu His Tyr Ser Gln Glu Leu Ser Leu Leu
        3075                3080                3085

Tyr Leu Leu Gln Asp Asp Val Asp Arg Ala Lys Tyr Tyr Ile Gln Asn
        3090                3095            3100

Gly Ile Gln Ser Phe Met Gln Asn Tyr Ser Ser Ile Asp Val Leu Leu
3105            3110                3115                3120

His Gln Ser Arg Leu Thr Lys Leu Gln Ser Val Gln Ala Leu Thr Glu
            3125                3130            3135

Ile Gln Glu Phe Ile Ser Phe Ile Ser Lys Gln Gly Asn Leu Ser Ser
            3140                3145                3150

Gln Val Pro Leu Lys Arg Leu Leu Asn Thr Trp Thr Asn Arg Tyr Pro
            3155                3160            3165

Asp Ala Lys Met Asp Pro Met Asn Ile Trp Asp Asp Ile Ile Thr Asn
        3170                3175            3180

Arg Cys Phe Phe Leu Ser Lys Ile Glu Glu Lys Leu Thr Pro Leu Pro
3185            3190                3195                3200

Glu Asp Asn Ser Met Asn Val Asp Gln Asp Gly Asp Pro Ser Asp Arg
            3205                3210            3215

Met Glu Val Gln Glu Gln Glu Glu Asp Ile Ser Ser Leu Ile Arg Ser
            3220                3225            3230

Cys Lys Phe Ser Met Lys Met Lys Met Ile Asp Ser Ala Arg Lys Gln
        3235                3240                3245

Asn Asn Phe Ser Leu Ala Met Lys Leu Leu Lys Glu Leu His Lys Glu
            3250                3255            3260

Ser Lys Thr Arg Asp Asp Trp Leu Val Ser Trp Val Gln Ser Tyr Cys
3265            3270                3275                3280

Arg Leu Ser His Cys Arg Ser Arg Ser Gln Gly Cys Ser Glu Gln Val
            3285                3290            3295

Leu Thr Val Leu Lys Thr Val Ser Leu Leu Asp Glu Asn Asn Val Ser
            3300                3305            3310

Ser Tyr Leu Xaa Lys Asn Ile Leu Ala Phe Arg Asp Gln Asn Ile Leu
            3315                3320            3325

Leu Gly Thr Thr Tyr Arg Ile Ile Ala Asn Ala Leu Ser Ser Glu Pro
        3330                3335            3340

Ala Cys Leu Ala Glu Ile Glu Glu Asp Lys Ala Arg Arg Ile Leu Glu
3345            3350                3355                3360

Leu Ser Gly Ser Ser Glu Asp Ser Glu Lys Val Ile Ala Gly Leu
            3365                3370                3375

Tyr Gln Arg Ala Phe Gln His Leu Ser Glu Ala Val Gln Ala Ala Glu
            3380                3385                3390

Glu Glu Ala Gln Pro Pro Ser Trp Ser Cys Gly Pro Ala Ala Gly Val
            3395                3400            3405

Ile Asp Ala Tyr Met Thr Leu Ala Asp Phe Cys Asp Gln Gln Leu Arg
        3410                3415            3420

Lys Glu Glu Glu Asn Ala Ser Val Thr Asp Ser Ala Glu Leu Gln Ala
3425            3430                3435                3440

Tyr Pro Ala Leu Val Val Glu Lys Met Leu Ala Leu Lys Leu Asn
            3445                3450            3455

Ser Asn Glu Ala Arg Leu Lys Phe Pro Arg Leu Leu Gln Ile Ile Glu
```

-continued

```
                 3460                3465                3470
Arg Tyr Pro Glu Glu Thr Leu Ser Leu Met Thr Lys Glu Ile Ser Ser
             3475                3480                3485
Val Pro Cys Trp Gln Phe Ile Ser Trp Ile Ser His Met Val Ala Leu
         3490                3495                3500
Leu Asp Lys Asp Gln Ala Val Ala Val Gln His Ser Val Glu Glu Ile
3505                3510                3515                3520
Thr Asp Asn Tyr Pro Gln Ala Ile Val Tyr Pro Phe Ile Ile Ser Ser
                 3525                3530                3535
Glu Ser Tyr Ser Phe Lys Asp Thr Ser Thr Gly His Lys Asn Lys Glu
             3540                3545                3550
Phe Val Ala Arg Ile Lys Ser Lys Leu Asp Gln Gly Gly Val Ile Gln
         3555                3560                3565
Asp Phe Ile Asn Ala Leu Asp Gln Leu Ser Asn Pro Glu Leu Leu Phe
     3570                3575                3580
Lys Asp Trp Ser Asn Asp Val Arg Ala Glu Leu Ala Lys Thr Pro Val
3585                3590                3595                3600
Asn Lys Lys Asn Ile Glu Lys Met Tyr Glu Arg Met Tyr Ala Ala Leu
                 3605                3610                3615
Gly Asp Pro Lys Ala Pro Gly Leu Gly Ala Phe Arg Arg Lys Phe Ile
             3620                3625                3630
Gln Thr Phe Gly Lys Glu Phe Asp Lys His Phe Gly Lys Gly Gly Ser
         3635                3640                3645
Lys Leu Leu Arg Met Lys Leu Ser Asp Phe Asn Asp Ile Thr Asn Met
     3650                3655                3660
Leu Leu Leu Lys Met Asn Lys Asp Ser Lys Pro Pro Gly Asn Leu Lys
3665                3670                3675                3680
Glu Cys Ser Pro Trp Met Ser Asp Phe Lys Val Glu Phe Leu Arg Asn
                 3685                3690                3695
Glu Leu Glu Ile Pro Gly Gln Tyr Asp Gly Arg Gly Lys Pro Leu Pro
             3700                3705                3710
Glu Tyr His Val Arg Ile Ala Gly Phe Asp Glu Arg Val Thr Val Met
         3715                3720                3725
Ala Ser Leu Arg Arg Pro Lys Arg Ile Ile Ile Arg Gly His Asp Glu
     3730                3735                3740
Arg Glu His Pro Phe Leu Val Lys Gly Gly Glu Asp Leu Arg Gln Asp
3745                3750                3755                3760
Gln Arg Val Glu Gln Leu Phe Gln Val Met Asn Gly Ile Leu Ala Gln
                 3765                3770                3775
Asp Ser Ala Cys Ser Gln Arg Ala Leu Gln Leu Arg Thr Tyr Ser Val
             3780                3785                3790
Val Pro Met Thr Ser Ser Asp Pro Arg Ala Pro Pro Cys Glu Tyr Lys
         3795                3800                3805
Asp Trp Leu Thr Lys Met Ser Gly Lys His Asp Val Gly Ala Tyr Met
     3810                3815                3820
Leu Met Tyr Lys Gly Ala Asn Arg Thr Glu Thr Val Thr Ser Glu Arg
3825                3830                3835                3840
Lys Arg Glu Ser Lys Val Pro Ala Asp Leu Leu Lys Arg Ala Phe Val
                 3845                3850                3855
Arg Met Ser Thr Ser Pro Glu Ala Phe Leu Ala Leu Arg Ser His Phe
             3860                3865                3870
Ala Ser Ser His Ala Leu Ile Cys Ile Ser His Trp Ile Leu Gly Ile
         3875                3880                3885
```

```
Gly Asp Arg His Leu Asn Asn Phe Met Val Ala Met Glu Thr Gly Gly
    3890                3895                3900
Val Ile Gly Ile Asp Phe Gly His Ala Phe Gly Ser Ala Thr Gln Phe
3905            3910                3915                3920
Leu Pro Val Pro Glu Leu Met Pro Phe Arg Leu Thr Arg Gln Phe Ile
                3925                3930                3935
Asn Leu Met Leu Pro Met Lys Glu Thr Gly Leu Met Tyr Ser Ile Met
            3940                3945                3950
Val His Ala Leu Arg Ala Phe Arg Ser Asp Pro Gly Leu Leu Thr Asn
        3955                3960                3965
Thr Met Asp Val Phe Val Lys Glu Pro Ser Phe Asp Trp Lys Asn Phe
    3970                3975                3980
Glu Gln Lys Met Leu Lys Lys Gly Gly Ser Trp Ile Gln Glu Ile Asn
3985                3990                3995                4000
Val Ala Glu Lys Asn Trp Tyr Pro Arg Gln Lys Ile Cys Tyr Ala Lys
                4005                4010                4015
Arg Lys Leu Ala Gly Ala Asn Pro Ala Val Ile Thr Cys Asp Glu Leu
            4020                4025                4030
Leu Leu Gly His Glu Lys Ala Pro Ala Phe Arg Asp Tyr Val Ala Val
        4035                4040                4045
Ala Arg Gly Ser Lys Asp His Asn Ile Arg Ala Gln Glu Pro Glu Ser
    4050                4055                4060
Gly Leu Ser Glu Glu Thr Gln Val Lys Cys Ile Met Asp Gln Ala Thr
4065                4070                4075                4080
Asp Pro Asn Ile Leu Gly Arg Thr Trp Glu Gly Trp Glu Pro Trp Met
                4085                4090                4095

<210> SEQ ID NO 35
<211> LENGTH: 1014
<212> TYPE: PRT
<213> ORGANISM: Human

<400> SEQUENCE: 35

Met Ala Glu Ser Ser Asp Lys Leu Tyr Arg Val Glu Tyr Ala Lys Ser
 1               5                  10                  15
Gly Arg Ala Ser Cys Lys Lys Cys Ser Glu Ser Ile Pro Lys Asp Ser
            20                  25                  30
Leu Arg Met Ala Ile Met Val Gln Ser Pro Met Phe Asp Gly Lys Val
        35                  40                  45
Pro His Trp Tyr His Phe Ser Cys Phe Trp Lys Val Gly His Ser Ile
    50                  55                  60
Arg His Pro Asp Val Glu Val Asp Gly Phe Ser Glu Leu Arg Trp Asp
65                  70                  75                  80
Asp Gln Gln Lys Val Lys Lys Thr Ala Glu Ala Gly Gly Val Thr Gly
                85                  90                  95
Lys Gly Gln Asp Gly Ile Gly Ser Lys Ala Glu Lys Thr Leu Gly Asp
            100                 105                 110
Phe Ala Ala Glu Tyr Ala Lys Ser Asn Arg Ser Thr Cys Lys Gly Cys
        115                 120                 125
Met Glu Lys Ile Glu Lys Gly Gln Val Arg Leu Ser Lys Lys Met Val
    130                 135                 140
Asp Pro Glu Lys Pro Gln Leu Gly Met Ile Asp Arg Trp Tyr His Pro
145                 150                 155                 160
Gly Cys Phe Val Lys Asn Arg Glu Glu Leu Gly Phe Arg Pro Glu Tyr
```

```
                    165                 170                 175
Ser Ala Ser Gln Leu Lys Gly Phe Ser Leu Leu Ala Thr Glu Asp Lys
                180                 185                 190

Glu Ala Leu Lys Lys Gln Leu Pro Gly Val Lys Ser Glu Gly Lys Arg
            195                 200                 205

Lys Gly Asp Glu Val Asp Gly Val Asp Glu Val Ala Lys Lys Lys Ser
        210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
                260                 265                 270

Pro Ser Gly Glu Ser Ala Ile Leu Asp Arg Val Ala Asp Gly Met Val
            275                 280                 285

Phe Gly Ala Leu Leu Pro Cys Glu Glu Cys Ser Gly Gln Leu Val Phe
        290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
                340                 345                 350

Gln Asp Arg Ile Phe Pro Pro Glu Thr Ser Ala Ser Val Ala Ala Thr
            355                 360                 365

Pro Pro Pro Ser Thr Ala Ser Ala Pro Ala Ala Val Asn Ser Ser Ala
        370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Met Glu Glu Val Lys Glu
        435                 440                 445

Ala Asn Ile Arg Val Val Ser Glu Asp Phe Leu Gln Asp Val Ser Ala
        450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
        515                 520                 525

Gly Gly Ala Ala Val Asp Pro Asp Ser Gly Leu Glu His Ser Ala His
        530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
                580                 585                 590
```

```
Gly Thr Val Ile Gly Ser Asn Lys Leu Glu Gln Met Pro Ser Lys Glu
        595                 600                 605
Asp Ala Ile Glu His Phe Met Lys Leu Tyr Glu Glu Lys Thr Gly Asn
        610                 615                 620
Ala Trp His Ser Lys Asn Phe Thr Lys Tyr Pro Lys Lys Phe Tyr Pro
625                 630                 635                 640
Leu Glu Ile Asp Tyr Gly Gln Asp Glu Ala Val Lys Lys Leu Thr
        645                 650                 655
Val Asn Pro Gly Thr Lys Ser Lys Leu Pro Lys Pro Val Gln Asp Leu
        660                 665                 670
Ile Lys Met Ile Phe Asp Val Glu Ser Met Lys Lys Ala Met Val Glu
        675                 680                 685
Tyr Glu Ile Asp Leu Gln Lys Met Pro Leu Gly Lys Leu Ser Lys Arg
        690                 695                 700
Gln Ile Gln Ala Ala Tyr Ser Ile Leu Ser Glu Val Gln Gln Ala Val
705                 710                 715                 720
Ser Gln Gly Ser Ser Asp Ser Gln Ile Leu Asp Leu Ser Asn Arg Phe
        725                 730                 735
Tyr Thr Leu Ile Pro His Asp Phe Gly Met Lys Lys Pro Pro Leu Leu
        740                 745                 750
Asn Asn Ala Asp Ser Val Gln Ala Lys Val Glu Met Leu Asp Asn Leu
        755                 760                 765
Leu Asp Ile Glu Val Ala Tyr Ser Leu Leu Arg Gly Gly Ser Asp Asp
        770                 775                 780
Ser Ser Lys Asp Pro Ile Asp Val Asn Tyr Glu Lys Leu Lys Thr Asp
785                 790                 795                 800
Ile Lys Val Val Asp Arg Asp Ser Glu Glu Ala Glu Ile Ile Arg Lys
                805                 810                 815
Tyr Val Lys Asn Thr His Ala Thr Thr His Asn Ala Tyr Asp Leu Glu
                820                 825                 830
Val Ile Asp Ile Phe Lys Ile Glu Arg Glu Gly Glu Cys Gln Arg Tyr
        835                 840                 845
Lys Pro Phe Lys Gln Leu His Asn Arg Arg Leu Leu Trp His Gly Ser
850                 855                 860
Arg Thr Thr Asn Phe Ala Gly Ile Leu Ser Gln Gly Leu Arg Ile Ala
865                 870                 875                 880
Pro Pro Glu Ala Pro Val Thr Gly Tyr Met Phe Gly Lys Gly Ile Tyr
                885                 890                 895
Phe Ala Asp Met Val Ser Lys Ser Ala Asn Tyr Cys His Thr Ser Gln
                900                 905                 910
Gly Asp Pro Ile Gly Leu Ile Leu Leu Gly Glu Val Ala Leu Gly Asn
        915                 920                 925
Met Tyr Glu Leu Lys His Ala Ser His Ile Ser Lys Leu Pro Lys Gly
        930                 935                 940
Lys His Ser Val Lys Gly Leu Gly Lys Thr Thr Pro Asp Pro Ser Ala
945                 950                 955                 960
Asn Ile Ser Leu Asp Gly Val Asp Val Pro Leu Gly Thr Gly Ile Ser
                965                 970                 975
Ser Gly Val Asn Asp Thr Ser Leu Leu Tyr Asn Glu Tyr Ile Val Tyr
                980                 985                 990
Asp Ile Ala Gln Val Asn Leu Lys Tyr Leu Leu Lys Leu Lys Phe Asn
        995                 1000                1005
```

```
Phe Lys Thr Ser Leu Trp
    1010

<210> SEQ ID NO 36
<211> LENGTH: 4
<212> TYPE: PRT
<213> ORGANISM: Human

<400> SEQUENCE: 36

Val Gly Pro Asp
  1

<210> SEQ ID NO 37
<211> LENGTH: 5
<212> TYPE: PRT
<213> ORGANISM: Human

<400> SEQUENCE: 37

Ile Ser Ala Asp Glu
  1               5
```